(12) United States Patent
Ohri et al.

(10) Patent No.: US 9,919,063 B2
(45) Date of Patent: Mar. 20, 2018

(54) MULTI-ENCAPSULATED FORMULATIONS MADE WITH OXIDIZED CELLULOSE

(71) Applicant: Covidien LP, Mansfield, MA (US)

(72) Inventors: Rachit Ohri, Framingham, MA (US); Phillip D. Blaskovich, Salem, MA (US); Olga Cherniavsky, Brookline, MA (US)

(73) Assignee: Covidien LP, Mansfield, MA (US)

( * ) Notice: Subject to any disclaimer, the term of this patent is extended or adjusted under 35 U.S.C. 154(b) by 19 days.

(21) Appl. No.: 14/424,464

(22) PCT Filed: Sep. 17, 2013

(86) PCT No.: PCT/US2013/060123
§ 371 (c)(1),
(2) Date: Feb. 27, 2015

(87) PCT Pub. No.: WO2014/043686
PCT Pub. Date: Mar. 20, 2014

(65) Prior Publication Data
US 2015/0202326 A1     Jul. 23, 2015

Related U.S. Application Data

(63) Continuation of application No. 14/025,002, filed on Sep. 12, 2013, now Pat. No. 9,138,489, and a continuation of application No. 13/903,297, filed on May 28, 2013, now Pat. No. 9,271,937.

(60) Provisional application No. 61/701,828, filed on Sep. 17, 2012, provisional application No. 61/701,826, filed on Sep. 17, 2012, provisional application No. 61/653,620, filed on May 31, 2012.

(51) Int. Cl.
| | |
|---|---|
| *A61K 51/00* | (2006.01) |
| *A61M 36/14* | (2006.01) |
| *A01N 43/04* | (2006.01) |
| *A61K 49/00* | (2006.01) |
| *A61K 49/22* | (2006.01) |
| *A61K 49/04* | (2006.01) |
| *A61K 49/18* | (2006.01) |
| *A61K 51/12* | (2006.01) |
| *A61K 9/50* | (2006.01) |
| *A61K 31/282* | (2006.01) |
| *A61K 31/445* | (2006.01) |
| *A61K 31/714* | (2006.01) |
| *A61L 31/04* | (2006.01) |
| *A61L 31/18* | (2006.01) |
| *B82Y 5/00* | (2011.01) |
| *B82Y 30/00* | (2011.01) |

(52) U.S. Cl.
CPC ............ *A61K 49/00* (2013.01); *A61K 9/5031* (2013.01); *A61K 9/5042* (2013.01); *A61K 9/5073* (2013.01); *A61K 9/5084* (2013.01); *A61K 31/282* (2013.01); *A61K 31/445* (2013.01); *A61K 31/714* (2013.01); *A61K 49/0017* (2013.01); *A61K 49/0091* (2013.01); *A61K 49/04* (2013.01); *A61K 49/1818* (2013.01); *A61K 49/225* (2013.01); *A61K 51/1251* (2013.01); *A61L 31/042* (2013.01); *A61L 31/18* (2013.01); *B82Y 5/00* (2013.01); *B82Y 30/00* (2013.01)

(58) Field of Classification Search
CPC ...... A61L 31/042; A61L 31/18; A61K 31/282
USPC .......................................... 424/9.1, 9.3, 9.4
See application file for complete search history.

(56) References Cited

U.S. PATENT DOCUMENTS

| | | | |
|---|---|---|---|
| 4,166,800 A | 9/1979 | Fong | |
| 6,309,569 B1 | 10/2001 | Farrar et al. | |
| 6,627,749 B1 | 9/2003 | Kumar | |
| 2005/0131225 A1 | 6/2005 | Kumar et al. | |
| 2006/0051408 A1* | 3/2006 | Parente Duena | ..... A23L 1/0029 424/451 |
| 2008/0214695 A1 | 12/2008 | Pathak et al. | |
| 2009/0162407 A1* | 6/2009 | Biggs | ..... A01N 25/12 424/401 |
| 2009/0263441 A1 | 10/2009 | McKay | |
| 2010/0008870 A1* | 1/2010 | Dihora | ..... A61K 8/11 424/59 |
| 2010/0203151 A1 | 8/2010 | Hiraoka | |
| 2011/0082427 A1* | 4/2011 | Golzarian | ..... A61L 24/0015 604/187 |
| 2011/0089375 A1 | 4/2011 | Chan et al. | |
| 2011/0293690 A1 | 12/2011 | Griffin et al. | |
| 2012/0156289 A1 | 6/2012 | Blaskovich et al. | |

FOREIGN PATENT DOCUMENTS

| | | |
|---|---|---|
| WO | WO2012/034049 A2 | 3/2012 |
| WO | WO2012/045094 A1 | 4/2012 |

OTHER PUBLICATIONS

International Search Report for PCT/US13/60123 dated Mar. 22, 2014 (4 pages).
Extended European Search Report for application No. 13836837.8 dated May 20, 2016.
Sanghvi et al., A Method to Control Particle Size of Cellulose Acetate Trimellitate Microspheres, Journal of Microencapsulation, vol. 10, No. 2, 181-194, Apr. 1993, XP000303737.
Australian Examination Report issued in Appl. No. AU 2013314997 dated Jul. 20, 2017.

* cited by examiner

*Primary Examiner* — Johann R Richter
*Assistant Examiner* — Courtney Brown

(57) ABSTRACT

A microsphere and method for forming the same are disclosed. The microsphere includes modified cellulose and at least one of a visualization agent, a magnetic material, or a radioactive material.

20 Claims, 22 Drawing Sheets

MULTI-ENCAPSULATED FORMULATIONS MADE WITH OXIDIZED CELLULOSE

CROSS-REFERENCE TO RELATED APPLICATIONS

This application is a National Stage Application of PCT/US13/60123 under 35USC § 371 (a), which claims priority of U.S. patent application Ser. No. 14/025,002 filed Sep. 12, 2013, which claims priority of U.S. Provisional Patent Application Ser. No. 61/701,828 filed Sep. 17, 2012, and also claims priority of U.S. patent application Ser. No. 13/903,297 filed May 28, 2013, which claims priority of U.S. Provisional Patent Application Ser. No. 61/653,620 filed May 31, 2012, and also claims priority of U.S. Provisional Patent Application Ser. No. 61/701,826 filed Sep. 17, 2012, the disclosures of each of the above-identified applications are hereby incorporated by reference in their entirety.

BACKGROUND

Technical Field

The present disclosure relates to systems and methods for dissolving cellulose. In particular, the present disclosure provides processes for dissolving modified cellulose.

Background of Related Art

Cellulose is the most abundant biorenewable material, and cellulose-derived products have been used in multiple industries, including manufacturing of textiles and medical devices. Apart from the use of unmodified cellulose-containing materials (for example wood, cotton), modern cellulose technology requires extraction and processing of cellulose from primary sources using techniques that have changed very little since the inception of the modern chemical industry.

The full potential of cellulose and cellulose products has not been fully exploited, partially due to the historical shift towards petroleum-based polymers, and also by the limited number of common solvents in which cellulose is readily soluble. Traditional cellulose dissolution processes, including the cuprammonium and xanthate processes, are often cumbersome or expensive and require the use of unusual solvents, typically with a high ionic strength, under relatively harsh conditions.

Various processes for dissolving cellulose have been previously disclosed. See, for example, McCormick, et al. "Solution Studies of Cellulose in Lithium Chloride and N,N-Dimethylacetamide," Macromolecules, 1985, Vol. 18, No. 12, 1985, pp. 2394-2401; Timpa, "Application of Universal Calibration in Gel Permeation Chromatography for Molecular Weight Determination of Plant Cell Wall Polymers: Cotton Fiber," J. Agric. Food Chem., 1991, 39, 270-275; and Strli et al., "Size Exclusion Chromatography of Cellulose in LiCl/N,N-Dimethylacetamide," J. Biochem. Biophys. Methods, 2003, 56, pp. 265-279.

Improved processes for dissolving cellulose, that overcome the need for high thermal treatment, excessive physical manipulation (e.g., stirring), and/or lengthy treatment periods, all of which contribute to the degradation of the cellulose and removal of oxidized groups from oxidized cellulose, remain desirable.

SUMMARY

In one embodiment, the present disclosure provides a process including: forming a mixture by contacting a modified cellulose with a solvent under an inert atmosphere to form a swelled modified cellulose; adjusting the mixture to a first temperature from about 115° C. to about 145° C.; contacting the swelled modified cellulose with a salt under the inert atmosphere to form a modified cellulose solution; and adjusting the modified cellulose solution to a second temperature from about 90° C. to about 120° C.

According to an aspect of the above embodiment, the first temperature is from about 120° C. to about 140° C.

According to an aspect of the above embodiment, the first temperature is from about 130° C. to about 135° C.

According to an aspect of the above embodiment, the second temperature is from about 100° C. to about 110° C.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the modified cellulose is an oxidized cellulose.

According to an aspect of the above embodiment, the modified cellulose solution includes dissolved oxidized cellulose having a degree of oxidation from about 80% to about 120% of a degree of oxidation of predissolved oxidized cellulose.

According to an aspect of the above embodiment, the modified cellulose solution includes dissolved oxidized cellulose having a molecular weight from about 80% to about 120% of the molecular weight of predissolved oxidized cellulose.

According to another embodiment, the present disclosure provides a process including: forming a mixture by contacting an oxidized cellulose with a solvent under an inert atmosphere to form a swelled oxidized cellulose, the oxidized cellulose having a degree of oxidation of from about 0.2 to about 1.0; adjusting the mixture to a first temperature from about 115° C. to about 145° C.; contacting the swelled oxidized cellulose with a salt under the inert atmosphere to form an oxidized cellulose solution; and adjusting the oxidized cellulose solution to a second temperature from about 90° C. to about 120° C., wherein the dissolved oxidized cellulose has a degree of oxidation from about 80% to about 120% of the degree of oxidation of predissolved oxidized cellulose.

According to an aspect of the above embodiment, the first temperature is from about 120° C. to about 140° C.

According to an aspect of the above embodiment, the second temperature from about 100° C. to about 110° C.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the salt is present in an amount of from about 0.1% by weight to 3% by weight of the oxidized cellulose.

In a further embodiment, the present disclosure provides for a process including: forming a mixture by contacting a modified cellulose with a solvent under an inert atmosphere to form a swelled modified cellulose; adjusting the mixture to a first temperature from about 115° C. to about 145° C.; contacting the swelled modified cellulose with a salt under the inert atmosphere to form a modified cellulose solution under the inert atmosphere; and adjusting the modified cellulose solution to a second temperature from about 90° C. to about 120° C., wherein the dissolved modified cellulose has a molecular weight from about 80% to about 100% of the molecular weight of predissolved modified cellulose.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the first temperature is from about 120° C. to about 140° C.

According to an aspect of the above embodiment, the second temperature from about 100° C. to about 110° C.

According to an aspect of the above embodiment, the salt is present in an amount of from about 0.1% by weight to 3% by weight of the modified cellulose.

According to an aspect of the above embodiment, the modified cellulose is an oxidized cellulose.

In one embodiment, the present disclosure provides for a solution of modified cellulose that is formed by contacting a modified cellulose with a solvent under an inert atmosphere to form a swelled modified cellulose; adjusting the mixture to a first temperature; contacting the swelled modified cellulose with a salt under the inert atmosphere to form a modified cellulose solution; adjusting the modified cellulose solution to a second temperature that is lower than the first temperature; and contacting the modified cellulose solution with at least one multivalent cation to form a plurality of modified cellulose particles.

According to an aspect of the above embodiment, the contacting of the swelled modified cellulose is performed after adjusting the first temperature.

The present disclosure also provides a solution of modified cellulose including dissolved modified cellulose having a molecular weight from about 80% to about 100% of the molecular weight of predissolved modified cellulose.

In one embodiment, the present disclosure provides a process including: forming a modified cellulose solution; and contacting the modified cellulose solution with at least one multivalent cation to form a plurality of modified cellulose particles.

According to an aspect of the above embodiment, the forming of the modified cellulose solution includes: contacting a modified cellulose with a solvent under an inert atmosphere to form a swelled modified cellulose; adjusting the swelled modified cellulose mixture to a first temperature; contacting the swelled modified cellulose with a salt under the inert atmosphere to form a modified cellulose solution; and adjusting the modified cellulose solution to a second temperature that is lower than the first temperature.

According to an aspect of the above embodiment, the at least one multivalent cation is selected from the group consisting of cations of calcium, barium, zinc, magnesium, chromium, platinum, and iron.

According to an aspect of the above embodiment, the process further includes shearing the modified solution to form the plurality of modified cellulose particles.

According to an aspect of the above embodiment, the first temperature is from about 115° C. to about 145° C. and the second temperature is from about 90° C. to about 120° C.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the modified cellulose is an oxidized cellulose.

According to an aspect of the above embodiment, the plurality of modified cellulose particles include oxidized cellulose having a degree of oxidation from about 80% to about 120% of a degree of oxidation of predissolved oxidized cellulose.

According to an aspect of the above embodiment, the plurality of modified cellulose particles include oxidized cellulose having a molecular weight from about 80% to about 120% of the molecular weight of predissolved oxidized cellulose.

In one embodiment, the present disclosure provides a process including: forming an oxidized cellulose solution; and contacting the oxidized cellulose solution with at least one multivalent cation to form a plurality of oxidized cellulose particles having a degree of oxidation from about 80% to about 120% of the degree of oxidation of predissolved oxidized cellulose.

According to an aspect of the above embodiment, the forming of the oxidized cellulose solution includes: contacting an oxidized cellulose with a solvent under an inert atmosphere to form a swelled oxidized cellulose having a degree of oxidation of from about 0.2 to about 1.0; adjusting the swelled oxidized cellulose to a first temperature; contacting the swelled oxidized cellulose with a salt under the inert atmosphere to form an oxidized cellulose solution; and adjusting the oxidized cellulose solution to a second temperature that is lower than the first temperature.

According to an aspect of the above embodiment, the first temperature is from about 120° C. to about 140° C. and the second temperature from about 100° C. to about 110° C.

According to an aspect of the above embodiment, including shearing the oxidized solution to form the plurality of oxidized cellulose particles.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the at least one multivalent cation is selected from the group consisting of cations of calcium, barium, zinc, magnesium, chromium, platinum, and iron.

In one embodiment, the present disclosure provides a process including: forming a modified cellulose solution; and contacting the modified cellulose solution with at least one multivalent cation to form a plurality of modified cellulose particles having a molecular weight from about 80% to about 100% of the molecular weight of predissolved modified cellulose.

According to an aspect of the above embodiment, the forming of the modified cellulose solution includes: contacting a modified cellulose with a solvent under an inert atmosphere to form a swelled modified cellulose; adjusting the swelled modified cellulose mixture to a first temperature;

contacting the swelled modified cellulose with a salt under the inert atmosphere to form an modified cellulose solution; and adjusting the modified cellulose solution to a second temperature that is lower than the first temperature.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the first temperature is from about 120° C. to about 140° C. and the second temperature from about 100° C. to about 110° C.

According to an aspect of the above embodiment, the process further includes shearing the modified solution to form the plurality of modified cellulose particles.

According to an aspect of the above embodiment, the at least one multivalent cation is selected from the group consisting of cations of calcium, barium, zinc, magnesium, chromium, platinum, and iron.

According to an aspect of the above embodiment, wherein the modified cellulose is an oxidized cellulose.

In one embodiment, the present disclosure provides a process for forming a composition including: forming a modified cellulose solution; forming a cationic composition cross-linkable with the modified cellulose solution; and contacting the modified cellulose solution and the cationic composition at a treatment site thereby forming an ionically cross-linked gel.

According to an aspect of the above embodiment, the formation of the modified cellulose solution includes: contacting a modified cellulose with a solvent under an inert atmosphere to form a swelled modified cellulose; adjusting the swelled modified cellulose mixture to a first temperature; contacting the swelled modified cellulose with a salt under the inert atmosphere to form a modified cellulose solution; and adjusting the modified cellulose solution to a second temperature that is lower than the first temperature.

According to an aspect of the above embodiment, the modified cellulose solution has a pH from about 8.0 to about 9.5.

According to an aspect of the above embodiment, the cationic composition is an aqueous solution of chitosan having a pH from about 2.0 to about 6.0.

According to an aspect of the above embodiment, the cationic composition is an aqueous solution of at least one multivalent cation.

According to an aspect of the above embodiment, the at least one multivalent cation is selected from the group consisting of cations of calcium, barium, zinc, magnesium, chromium, platinum, and iron.

According to an aspect of the above embodiment, the process further includes convergently applying the modified cellulose solution and the cationic composition onto a treatment site.

According to an aspect of the above embodiment, the modified cellulose is an oxidized cellulose.

In one embodiment, the present disclosure provides a process for forming a composition including: forming a modified cellulose solution; forming a gelation composition; and contacting the modified cellulose solution and the composition at a treatment site thereby forming a gel.

According to an aspect of the above embodiment, the formation of the modified cellulose solution includes: contacting a modified cellulose with a solvent under an inert atmosphere to form a swelled modified cellulose; adjusting the swelled modified cellulose mixture to a first temperature; contacting the swelled modified cellulose with a salt under the inert atmosphere to form a modified cellulose solution; and adjusting the modified cellulose solution to a second temperature that is lower than the first temperature.

According to an aspect of the above embodiment, the gelation composition is an aqueous solution of chitosan having a pH from about 2.0 to about 6.0.

According to an aspect of the above embodiment, the modified cellulose solution has a pH from about 8.0 to about 9.5.

According to an aspect of the above embodiment, the gelation composition is an aqueous solution of at least one multivalent cation.

According to an aspect of the above embodiment, the at least one multivalent cation is selected from the group consisting of cations of calcium, barium, zinc, magnesium, chromium, platinum, and iron.

According to an aspect of the above embodiment, gelation composition is selected from the group consisting of water, saline, phosphate buffered saline, and combinations thereof.

According to an aspect of the above embodiment, the gelation composition is an aqueous solution of carboxymethylcellulose, wherein the carboxymethylcellulose is present from about 0.5% by weight of the solution to about 5% by weight of the solution.

According to an aspect of the above embodiment, the gelation composition is a solution of an acrylic polymer based on at least one of methyl methacrylate, hydroxyethyl acrylate, hydroxyethyl methacrylate, glyceryl acrylate, glyceryl methacrylate, acrylic acid, methacrylic acid, acrylamide, or methacrylamide, and combinations thereof.

According to an aspect of the above embodiment, the solution includes a solvent selected from the group consisting of acetone, ethyl acetate, dimethyl ether, and combinations thereof.

According to an aspect of the above embodiment, the gelation composition includes a Schiff-base compound selected from the group consisting of amoxicillin, cephalexin, and combinations thereof.

According to an aspect of the above embodiment, the gelation composition includes trilysine, albumin, polyethylene glycol amine, and combinations thereof.

According to an aspect of the above embodiment, the process further includes convergently applying the modified cellulose solution and the gelation composition onto a treatment site.

According to an aspect of the above embodiment, wherein the modified cellulose is an oxidized cellulose.

In one embodiment, the present disclosure provides a process including: forming a modified cellulose solution; and contacting the modified cellulose solution with at least one non-solvent to form a plurality of modified cellulose particles.

According to an aspect of the above embodiment, the forming of the modified cellulose solution includes: contacting a modified cellulose with a solvent under an inert atmosphere to form a swelled modified cellulose; adjusting the swelled modified cellulose mixture to a first temperature; contacting the swelled modified cellulose with a salt under the inert atmosphere to form a modified cellulose solution; and adjusting the modified cellulose solution to a second temperature that is lower than the first temperature.

According to an aspect of the above embodiment, the at least one non-solvent is selected from the group consisting of alkanes, oils glycerins, glycols, and combinations thereof.

According to an aspect of the above embodiment, the process further includes shearing the modified solution to form the plurality of modified cellulose particles.

According to an aspect of the above embodiment, the first temperature is from about 115° C. to about 145° C. and the second temperature is from about 90° C. to about 120° C.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the modified cellulose is an oxidized cellulose.

According to an aspect of the above embodiment, the plurality of modified cellulose particles include oxidized cellulose having a degree of oxidation from about 80% to about 120% of a degree of oxidation of predissolved oxidized cellulose.

According to an aspect of the above embodiment, the plurality of modified cellulose particles include oxidized cellulose having a molecular weight from about 80% to about 120% of the molecular weight of predissolved oxidized cellulose.

In one embodiment, the present disclosure provides a process including: forming an oxidized cellulose solution; and contacting the oxidized cellulose solution with at least one non-solvent to form a plurality of oxidized cellulose particles having a degree of oxidation from about 80% to about 120% of the degree of oxidation of predissolved oxidized cellulose.

According to an aspect of the above embodiment, the forming of the oxidized cellulose solution includes: contacting an oxidized cellulose with a solvent under an inert atmosphere to form a swelled oxidized cellulose, the oxidized cellulose having a degree of oxidation of from about 0.2 to about 1.0; adjusting the swelled oxidized cellulose to a first temperature; contacting the swelled oxidized cellulose with a salt under the inert atmosphere to form an oxidized cellulose solution; and adjusting the oxidized cellulose solution to a second temperature that is lower than the first temperature.

According to an aspect of the above embodiment, the first temperature is from about 115° C. to about 145° C. and the second temperature is from about 90° C. to about 120° C.

According to an aspect of the above embodiment, the process further includes shearing the oxidized solution to form the plurality of oxidized cellulose particles.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the at least one non-solvent is selected from the group consisting of alkanes, oils glycerins, glycols, and combinations thereof.

In one embodiment, the present disclosure provides a process including: forming a modified cellulose solution; and contacting the modified cellulose solution with at least one non-solvent to form a plurality of modified cellulose particles having a molecular weight from about 80% to about 100% of the molecular weight of predissolved modified cellulose.

According to an aspect of the above embodiment, the forming of the modified cellulose solution includes: contacting a modified cellulose with a solvent under an inert atmosphere to form a swelled modified cellulose; adjusting the swelled modified cellulose mixture to a first temperature; contacting the swelled modified cellulose with a salt under the inert atmosphere to form a modified cellulose solution; and adjusting the modified cellulose solution to a second temperature that is lower than the first temperature.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the first temperature is from about 115° C. to about 145° C. and the second temperature is from about 90° C. to about 120° C.

According to an aspect of the above embodiment, the process further includes shearing the modified solution to form the plurality of modified cellulose particles.

According to an aspect of the above embodiment, the at least one non-solvent is selected from the group consisting of alkanes, oils glycerins, glycols, and combinations thereof.

In one embodiment, the present disclosure provides a process for forming a composition including: forming a modified cellulose solution; forming a precipitating composition; and contacting the modified cellulose solution and the precipitating composition at a treatment site thereby precipitating modified cellulose from the modified cellulose solution and forming a gel.

According to an aspect of the above embodiment, the formation of the modified cellulose solution includes: contacting a modified cellulose with a solvent under an inert atmosphere to form a swelled modified cellulose; adjusting the swelled modified cellulose mixture to a first temperature; contacting the swelled modified cellulose with a salt under the inert atmosphere to form a modified cellulose solution; and adjusting the modified cellulose solution to a second temperature that is lower than the first temperature.

According to an aspect of the above embodiment, the first temperature is from about 115° C. to about 145° C. and the second temperature is from about 90° C. to about 120° C.

According to an aspect of the above embodiment, the precipitating composition is selected from the group consisting of water, saline, phosphate buffered saline, and combinations thereof.

According to an aspect of the above embodiment, the precipitating composition is an aqueous solution of carboxymethylcellulose, wherein the carboxymethylcellulose is present from about 0.5% by weight of the solution to about 5% by weight of the solution.

According to an aspect of the above embodiment, the precipitating composition is a solution of an acrylic polymer based on at least one of methyl methacrylate, hydroxyethyl acrylate, hydroxyethyl methacrylate, glyceryl acrylate, glyceryl methacrylate, acrylic acid, methacrylic acid, acrylamide, or methacrylamide, and combinations thereof.

According to an aspect of the above embodiment, the precipitation composition solution includes a solvent selected from the group consisting of acetone, ethyl acetate, dimethyl ether, and combinations thereof.

According to an aspect of the above embodiment, the process further includes convergently applying the modified cellulose solution and the precipitating composition onto a treatment site.

In one embodiment, the present disclosure provides a process for forming a composition including: forming a modified cellulose solution; forming a cross-linkable composition covalently cross-linkable with the modified cellulose solution; and contacting the modified cellulose solution and the composition at a treatment site thereby forming a cross-linked gel.

According to an aspect of the above embodiment, the cross-linkable composition includes a Schiff-base compound selected from the group consisting of amoxicillin, cephalexin, and combinations thereof.

According to an aspect of the above embodiment, cross-linkable composition includes trilysine, albumin, polyethylene glycol amine, and combinations thereof.

According to an aspect of the above embodiment, the cross-linkable composition is an aqueous solution.

According to an aspect of the above embodiment, the process further includes convergently applying the modified cellulose solution and the cross-linkable composition onto a treatment site.

In one embodiment, the present disclosure provides a process for forming a composition including: forming a modified cellulose solution; forming a gelation composition; and contacting the modified cellulose solution and the composition at a treatment site thereby forming a gel.

According to an aspect of the above embodiment, the formation of the modified cellulose solution includes: contacting a modified cellulose with a solvent under an inert atmosphere to form a swelled modified cellulose; adjusting the swelled modified cellulose mixture to a first temperature; contacting the swelled modified cellulose with a salt under the inert atmosphere to form a modified cellulose solution; and adjusting the modified cellulose solution to a second temperature that is lower than the first temperature.

According to an aspect of the above embodiment, the first temperature is from about 115° C. to about 145° C. and the second temperature is from about 90° C. to about 120° C.

According to an aspect of the above embodiment, the gelation composition is an aqueous solution of chitosan having a pH from about 2.0 to about 6.0.

According to an aspect of the above embodiment, the modified cellulose solution has a pH from about 8.0 to about 9.5.

According to an aspect of the above embodiment, the gelation composition is an aqueous solution of at least one multivalent cation.

According to an aspect of the above embodiment, the at least one multivalent cation is selected from the group consisting of cations of calcium, barium, zinc, magnesium, chromium, platinum, and iron.

According to an aspect of the above embodiment, the gelation composition is selected from the group consisting of water, saline, phosphate buffered saline, and combinations thereof.

According to an aspect of the above embodiment, the gelation composition is an aqueous solution of carboxymethylcellulose, wherein the carboxymethylcellulose is present from about 0.5% by weight of the solution to about 5% by weight of the solution.

According to an aspect of the above embodiment, the gelation composition is a solution of an acrylic polymer based on at least one of methyl methacrylate, hydroxyethyl acrylate, hydroxyethyl methacrylate, glyceryl acrylate, glyceryl methacrylate, acrylic acid, methacrylic acid, acrylamide, or methacrylamide, and combinations thereof.

According to an aspect of the above embodiment, the solution includes a solvent selected from the group consisting of acetone, ethyl acetate, dimethyl ether, and combinations thereof.

According to an aspect of the above embodiment, the gelation composition includes a Schiff-base compound selected from the group consisting of amoxicillin, cephalexin, and combinations thereof.

According to an aspect of the above embodiment, the gelation composition includes trilysine, albumin, polyethylene glycol amine, and combinations thereof.

According to an aspect of the above embodiment, the process further includes convergently applying the modified cellulose solution and the gelation composition onto a treatment site.

In one embodiment, the present disclosure provides a process including: forming a modified cellulose solution; and contacting the dissolved modified cellulose with at least one neutralizing agent to form a plurality of modified cellulose particles.

According to an aspect of the above embodiment, forming of the modified cellulose solution includes: contacting a modified cellulose with a solvent under an inert atmosphere to form a swelled modified cellulose; adjusting the swelled modified cellulose mixture to a first temperature; contacting the swelled modified cellulose with a salt under the inert atmosphere to form a modified cellulose solution; and adjusting the modified cellulose solution to a second temperature that is lower than the first temperature.

According to an aspect of the above embodiment, the at least one neutralizing agent is selected from the group consisting of ammonia, ammonium hydroxide, potassium hydroxide, sodium hydroxide, sodium carbonate, sodium bicarbonate, lithium hydroxide, potassium carbonate, potassium bicarbonate, and combinations thereof.

According to an aspect of the above embodiment, the process further includes shearing the dissolved modified solution to form the plurality of modified cellulose particles.

According to an aspect of the above embodiment, the first temperature is from about 115° C. to about 145° C. and the second temperature is from about 90° C. to about 120° C.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the modified cellulose is an oxidized cellulose and the plurality of modified cellulose particles include oxidized cellulose having a degree of oxidation from about 80% to about 120% of a degree of oxidation of predissolved oxidized cellulose.

According to an aspect of the above embodiment, the plurality of modified cellulose particles include oxidized cellulose having a molecular weight from about 80% to about 120% of the molecular weight of predissolved oxidized cellulose.

In one embodiment, the present disclosure provides a process including: forming an oxidized cellulose solution; and contacting the dissolved oxidized cellulose with at least one neutralizing agent to form a plurality of oxidized cellulose particles having a degree of oxidation from about 80% to about 120% of the degree of oxidation of predissolved oxidized cellulose.

According to an aspect of the above embodiment, the forming of the oxidized cellulose solution includes: contacting an oxidized cellulose with a solvent under an inert atmosphere to form a swelled oxidized cellulose having a degree of oxidation of from about 0.2 to about 1.0; adjusting the swelled oxidized cellulose to a first temperature; contacting the swelled oxidized cellulose with a salt under the inert atmosphere to form an oxidized cellulose solution; and adjusting the oxidized cellulose solution to a second temperature that is lower than the first temperature.

According to an aspect of the above embodiment, the first temperature is from about 115° C. to about 145° C. and the second temperature is from about 90° C. to about 120° C.

According to an aspect of the above embodiment, the process further includes shearing the dissolved oxidized solution to form the plurality of oxidized cellulose particles.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the at least one neutralizing agent is selected from the group consisting of ammonia, ammonium hydroxide, potassium hydroxide, sodium hydroxide, sodium carbonate, sodium bicarbonate, lithium hydroxide, potassium carbonate, potassium bicarbonate, and combinations thereof.

In one embodiment, the present disclosure provides a process including: forming a modified cellulose solution; and contacting the dissolved modified cellulose with at least one neutralizing agent to form a plurality of modified cellulose particles having a molecular weight from about 80% to about 100% of the molecular weight of predissolved modified cellulose.

According to an aspect of the above embodiment, forming of the modified cellulose solution includes: contacting a modified cellulose with a solvent under an inert atmosphere to form a swelled modified cellulose; adjusting the swelled modified cellulose mixture to a first temperature; contacting the swelled modified cellulose with a salt under the inert atmosphere to form a modified cellulose solution; and adjusting the modified cellulose solution to a second temperature that is lower than the first temperature.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the first temperature is from about 115° C. to about 145° C. and the second temperature is from about 90° C. to about 120° C.

According to an aspect of the above embodiment, the process further includes shearing the dissolved modified solution to form the plurality of modified cellulose particles.

According to an aspect of the above embodiment, the at least one neutralizing agent is selected from the group consisting of ammonia, ammonium hydroxide, potassium hydroxide, sodium hydroxide, sodium carbonate, sodium bicarbonate, lithium hydroxide, potassium carbonate, potassium bicarbonate, and combinations thereof.

In one embodiment, the present disclosure provides a process for forming microspheres including: contacting a solvent with a modified cellulose to form a solution; contacting the modified cellulose solution with at least one bioactive agent to form a discontinuous phase liquid; contacting the discontinuous phase liquid with a continuous phase liquid to form an emulsion; and contacting the emulsion with a third phase liquid to extract the solvent from the emulsion, thereby forming a plurality of modified cellulose microspheres.

According to an aspect of the above embodiment, the bioactive agent is selected from the group consisting of a hydrophilic bioactive agent, a protein therapeutic, a biologic, and combinations thereof.

According to an aspect of the above embodiment, the third phase liquid is miscible with the continuous phase liquid and the discontinuous phase liquid.

According to an aspect of the above embodiment, the third phase liquid is selected from the group consisting of isopropyl myristate, hexane, triglycerides and combinations thereof.

According to an aspect of the above embodiment, the third phase liquid is present in an amount from about 300% by volume to about 200% by volume of the continuous phase liquid.

According to an aspect of the above embodiment, the formation of the modified cellulose solution includes: contacting a modified cellulose with the solvent under an inert atmosphere to form a swelled modified cellulose; adjusting the swelled modified cellulose mixture to a first temperature; contacting the swelled modified cellulose after adjusting the first temperature with a salt under the inert atmosphere to form a modified cellulose solution; and adjusting the modified cellulose solution to a second temperature from about 90° C. to about 120° C.

According to an aspect of the above embodiment, the first temperature is from about 115° C. to about 145° C. and the second temperature is from about 90° C. to about 120° C.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the continuous phase is selected from the group consisting of plant-based oils, petroleum-based oils, silicone-based oils, and combinations thereof.

According to an aspect of the above embodiment, the process further includes: contacting the plurality of modified cellulose microspheres with a solution of a biodegradable polymer and an aqueous solution to form an emulsion; and extracting a plurality of biodegradable polymer microspheres encapsulating the plurality of modified cellulose microspheres.

According to an aspect of the above embodiment, the biodegradable polymer is an aliphatic polyester.

According to an aspect of the above embodiment, the aqueous solution includes at least one emulsifier and water.

According to an aspect of the above embodiment, the at least one bioactive agent is hydrophilic.

In one embodiment, the present disclosure provides a microsphere including: modified cellulose; and at least one bioactive agent.

According to an aspect of the above embodiment, the bioactive agent is selected from the group consisting of a hydrophilic bioactive agent, a protein therapeutic, a biologic, and combinations thereof.

According to an aspect of the above embodiment, the microsphere is formed by: contacting a modified cellulose solution including a solvent with the at least one bioactive agent to form a discontinuous phase liquid; contacting the discontinuous phase liquid with a continuous phase liquid to form an emulsion; and contacting the emulsion with a third phase liquid to extract the solvent from the emulsion thereby forming a plurality of microspheres.

According to an aspect of the above embodiment, the third phase liquid is miscible with the continuous composition and the discontinuous composition.

According to an aspect of the above embodiment, the third phase liquid is selected from the group consisting of isopropyl myristate, hexane, triglycerides and combinations thereof.

According to an aspect of the above embodiment, the third phase liquid is present in an amount from about 300% by volume to about 200% by volume of the continuous phase liquid.

According to an aspect of the above embodiment, the formation of the modified cellulose solution includes: contacting a modified cellulose with the solvent under an inert atmosphere to form a swelled modified cellulose; adjusting the swelled modified cellulose mixture to a first temperature; contacting the swelled modified cellulose after adjusting the first temperature with a salt under the inert atmosphere to form a modified cellulose solution; and adjusting the modified cellulose solution to a second temperature from about 90° C. to about 120° C.

According to an aspect of the above embodiment, the first temperature is from about 115° C. to about 145° C. and the second temperature is from about 90° C. to about 120° C.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the continuous phase is selected from the group consisting of plant-based oils, petroleum-based oils, silicone-based oils, and combinations thereof.

In one embodiment, the present disclosure provides a process for forming microspheres including: forming a first plurality microspheres including at least one bioactive agent and modified cellulose; contacting the first plurality of microspheres with a solution of a biodegradable polymer to form a discontinuous phase liquid; contacting the discontinuous phase liquid with a continuous phase liquid to form an emulsion; and extracting a second plurality of microspheres from the emulsion, the second plurality of microspheres including the first plurality of microspheres.

According to an aspect of the above embodiment, the at least one bioactive agent is selected from the group consisting of a hydrophilic bioactive agent, a protein therapeutic, a biologic, and combinations thereof.

According to an aspect of the above embodiment, the biodegradable polymer is an aliphatic polyester.

According to an aspect of the above embodiment, the aliphatic polyester is selected from the group consisting of polylactide, polylactide-co-glycolide, polylactide-polycaprolactone, and combinations thereof.

According to an aspect of the above embodiment, the continuous phase liquid includes at least one emulsifier and water.

In one embodiment, the present disclosure provides a microsphere including a first biodegradable polymer encapsulating at least one additional microsphere, the at least one additional microsphere including a second biodegradable polymer and at least one bioactive agent, wherein the first biodegradable polymer and the second biodegradable polymer are different and at least one of the first biodegradable polymer or the second biodegradable polymer is modified cellulose.

According to an aspect of the above embodiment, at least one of the first biodegradable polymer or the second biodegradable polymer is an aliphatic polyester.

According to an aspect of the above embodiment, aliphatic polyester is selected from the group consisting of polylactide, polylactide-co-glycolide, polylactide-polycaprolactone, and combinations thereof.

According to an aspect of the above embodiment, the microsphere further includes at least one additional bioactive agent.

According to an aspect of the above embodiment, the at least one bioactive agent is selected from the group consisting of a hydrophilic bioactive agent, a protein therapeutic, a biologic, and combinations thereof and the first biodegradable polymer is modified cellulose.

In one embodiment, the present disclosure provides a medical device including at least one of a predictably degrading coating, film, or a fiber formed from a modified cellulose solution.

According to an aspect of the above embodiment, the solution is formed by: contacting a modified cellulose with a solvent under an inert atmosphere to form a swelled modified cellulose; adjusting the swelled modified cellulose mixture to a first temperature; contacting the swelled modified cellulose with a salt under the inert atmosphere to form a modified cellulose solution; and adjusting the modified cellulose solution to a second temperature.

According to an aspect of the above embodiment, the at least one of the fiber, the coating, or the film are formed by evaporating the solvent from the solution.

According to an aspect of the above embodiment, the at least one of the fiber, the coating, or the film are formed by depositing the modified cellulose solution on a substrate and evaporating the solvent from the solution.

According to an aspect of the above embodiment, the first temperature is from about 115° C. to about 145° C. and the second temperature is from about 90° C. to about 120° C.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the modified cellulose is an oxidized cellulose and the at least one of the fiber, the coating, or the film include oxidized cellulose having a degree of oxidation from about 80% to about 120% of the degree of oxidation of predissolved oxidized cellulose.

According to an aspect of the above embodiment, the at least one of the fiber, the coating, or the film include oxidized cellulose having a molecular weight from about 80% to about 120% of the molecular weight of predissolved oxidized cellulose.

According to an aspect of the above embodiment, the modified cellulose solution is contacted with at least one biocompatible plasticizer.

According to an aspect of the above embodiment, the at least one biocompatible plasticizer is selected from the group consisting lecithin, dibutyl sebacate, citric acid, polyethylene glycol, polypropylene glycol, and combinations thereof.

In one embodiment, the present disclosure provides a process including: contacting a modified cellulose with a solvent under an inert atmosphere to form a swelled modified cellulose; adjusting the swelled modified cellulose mixture to a first temperature; contacting the swelled modified cellulose with a salt under the inert atmosphere to form a modified cellulose solution; adjusting the modified cellulose solution to a second temperature that is lower than the first temperature; and forming at least one of a fiber, a coating, or a film from the modified cellulose solution.

According to an aspect of the above embodiment, the at least one of the fiber, the coating, or the film are formed by evaporating the solvent from the solution.

According to an aspect of the above embodiment, the first temperature is from about 115° C. to about 145° C. and the second temperature is from about 90° C. to about 120° C.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

According to an aspect of the above embodiment, the modified cellulose is an oxidized cellulose and the at least one of the fiber, the coating, or the film include oxidized cellulose having a degree of oxidation from about 80% to about 120% of a degree of oxidation of predissolved oxidized cellulose.

According to an aspect of the above embodiment, the at least one of the fiber, the coating, or the film include oxidized cellulose having a molecular weight from about 80% to about 120% of the molecular weight of predissolved oxidized cellulose.

According to an aspect of the above embodiment, the process further includes contacting the modified cellulose solution with at least one biocompatible plasticizer.

According to an aspect of the above embodiment, the at least one biocompatible plasticizer is selected from the group consisting lecithin, dibutyl sebacate, citric acid, polyethylene glycol, polypropylene glycol, and combinations thereof.

In one embodiment, the present disclosure also provides a microsphere including: modified cellulose; and at least one visualization agent.

According to an aspect of the above embodiment, the at least one visualization agent is selected from the group consisting of dyes, fluorescent compounds, x-ray contrast agents, ultrasonic contrast agents, MRI contrast agents, CT scan contrast agents, radionucleotides, and combinations thereof.

In one embodiment, the present disclosure also provides a method including: contacting a modified cellulose solution including a solvent with at least one visualization agent to form a discontinuous phase liquid; contacting the discontinuous phase liquid with a continuous phase liquid to form an emulsion; and contacting the emulsion with a third phase liquid to extract the solvent from the emulsion thereby forming a plurality of microspheres.

According to an aspect of the above embodiment, the third phase liquid is miscible with the continuous composition and the discontinuous composition.

According to an aspect of the above embodiment, the third phase liquid is selected from the group consisting of isopropyl myristate, hexane, triglycerides and combinations thereof.

According to an aspect of the above embodiment, the third phase liquid is present in an amount from about 300% by volume to about 200% by volume of the continuous phase liquid.

According to an aspect of the above embodiment, the formation of the modified cellulose solution includes: contacting a modified cellulose with the solvent under an inert atmosphere to form a swelled modified cellulose; adjusting the swelled modified cellulose mixture to a first temperature; contacting the swelled modified cellulose after adjusting the first temperature with a salt under the inert atmosphere to form a modified cellulose solution; and adjusting the modified cellulose solution to a second temperature.

According to an aspect of the above embodiment, the first temperature is from about 115° C. to about 145° C. and the second temperature is from about 90° C. to about 120° C.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

In one embodiment, the present disclosure also provides a microsphere including: a shell including a first biodegradable polymer encapsulating at least one second microsphere, the at least one second microsphere including a second biodegradable polymer and at least one visualization agent.

According to an aspect of the above embodiment, the first biodegradable polymer and the second biodegradable polymer are different and at least one of the first biodegradable polymer or the second biodegradable polymer is modified cellulose.

According to an aspect of the above embodiment, at least one of the first biodegradable polymer or the second biodegradable polymer is an aliphatic polyester.

According to an aspect of the above embodiment, the aliphatic polyester is selected from the group consisting of polylactide, polylactide-co-glycolide, polylactide-polycaprolactone, and combinations thereof.

According to an aspect of the above embodiment, the microsphere further includes at least one additional visualization agent different from the at least one visualization agent of the at least one second microsphere.

According to an aspect of the above embodiment, the microsphere further includes at least one first bioactive agent, wherein the at least one second microsphere includes at least one second bioactive agent, the at least one first bioactive agent and the at least one second bioactive agent are different.

According to an aspect of the above embodiment, the first biodegradable polymer encapsulates at least one third microsphere, the at least one third microsphere including at least one additional visualization agent different from the at least one visualization agent of the at least one second microsphere.

According to an aspect of the above embodiment, the at least one second microsphere includes at least one first bioactive agent and the at least one third microsphere includes at least one second bioactive agent, the at least one first bioactive agent and the at least one second bioactive agent are different.

According to an aspect of the above embodiment, the microsphere further includes at least one first bioactive agent, wherein the at least one second microsphere includes a second shell encapsulating at least one third microsphere including a third biodegradable polymer and at least one second bioactive agent.

In one embodiment, the present disclosure also provides modified cellulose; at least one first microsphere including at least one first hydrogel precursor; and at least one second microsphere including at least second hydrogel precursor cross-linkable with the at least one first hydrogel precursor.

According to an aspect of the above embodiment, the at least one first hydrogel precursor includes at least one electrophilic functional group.

According to an aspect of the above embodiment, the at least one electrophilic functional group is selected from the group consisting of N-hydroxysuccinimides, sulfosuccinimides, and combinations thereof.

According to an aspect of the above embodiment, the at least one second hydrogel precursor includes at least one nucleophilic functional group.

According to an aspect of the above embodiment, the at least one nucleophilic functional group is selected from the group consisting of amines, thiols, and combinations thereof.

According to an aspect of the above embodiment, the microsphere further includes at least one third microsphere encapsulating the at least one second microsphere.

In one embodiment, the present disclosure also provides a method including: contacting a modified cellulose solution including a solvent with at least one first hydrogel precursor or at least one second hydrogel precursor to form a discontinuous phase liquid; contacting the discontinuous phase liquid with a continuous phase liquid to form an emulsion; and contacting the emulsion with a third phase liquid to extract the solvent from the emulsion thereby forming a plurality of microspheres.

According to an aspect of the above embodiment, the third phase liquid is miscible with the continuous composition and the discontinuous composition.

According to an aspect of the above embodiment, third phase liquid is selected from the group consisting of isopropyl myristate, hexane, triglycerides and combinations thereof.

According to an aspect of the above embodiment, the third phase liquid is present in an amount from about 300% by volume to about 200% by volume of the continuous phase liquid.

According to an aspect of the above embodiment, the formation of the modified cellulose solution includes: contacting a modified cellulose with the solvent under an inert atmosphere to form a swelled modified cellulose; adjusting the swelled modified cellulose mixture to a first temperature; contacting the swelled modified cellulose after adjusting the first temperature with a salt under the inert atmosphere to form a modified cellulose solution; and adjusting the modified cellulose solution to a second temperature.

According to an aspect of the above embodiment, the first temperature is from about 115° C. to about 145° C. and the second temperature is from about 90° C. to about 120° C.

According to an aspect of the above embodiment, solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

In one embodiment, the present disclosure also provides a microsphere including: a shell including a first biodegradable polymer encapsulating at least one second microsphere, the at least one second microsphere including a second biodegradable polymer and at least one first hydrogel precursor and at least one third microsphere including the second biodegradable polymer and at least one second hydrogel precursor.

According to an aspect of the above embodiment, the first biodegradable polymer and the second biodegradable polymer are different and at least one of the first biodegradable polymer or the second biodegradable polymer is modified cellulose.

According to an aspect of the above embodiment, at least one of the first biodegradable polymer or the second biodegradable polymer is an aliphatic polyester.

According to an aspect of the above embodiment, the aliphatic polyester is selected from the group consisting of polylactide, polylactide-co-glycolide, polylactide-polycaprolactone, and combinations thereof.

According to an aspect of the above embodiment, the at least one first hydrogel precursor includes at least one electrophilic functional group.

According to an aspect of the above embodiment, the at least one electrophilic functional group is selected from the group consisting of N-hydroxysuccinimides, sulfosuccinimides, and combinations thereof.

According to an aspect of the above embodiment, the at least one second hydrogel precursor includes at least one nucleophilic functional group.

According to an aspect of the above embodiment, the at least one nucleophilic functional group is selected from the group consisting of amines, thiols, and combinations thereof.

In one embodiment, the present disclosure also provides a microsphere including: modified cellulose; and at least one magnetic material.

According to an aspect of the above embodiment, the at least one magnetic material includes a particle selected from the group consisting of ferrite, strontium ferrous oxide, neodymium, samarium, cobalt, aluminum, nickel, copper, iron, titanium, and combinations thereof.

In one embodiment, the present disclosure also provides a method including: contacting a modified cellulose solution including a solvent with at least one magnetic material to form a discontinuous phase liquid; contacting the discontinuous phase liquid with a continuous phase liquid to form an emulsion; and contacting the emulsion with a third phase liquid to extract the solvent from the emulsion thereby forming a plurality of microspheres.

According to an aspect of the above embodiment, the third phase liquid is miscible with the continuous composition and the discontinuous composition.

According to an aspect of the above embodiment, the third phase liquid is selected from the group consisting of isopropyl myristate, hexane, triglycerides and combinations thereof.

According to an aspect of the above embodiment, the third phase liquid is present in an amount from about 300% by volume to about 200% by volume of the continuous phase liquid.

According to an aspect of the above embodiment, the formation of the modified cellulose solution includes: contacting a modified cellulose with the solvent under an inert atmosphere to form a swelled modified cellulose; adjusting the swelled modified cellulose mixture to a first temperature; contacting the swelled modified cellulose after adjusting the first temperature with a salt under the inert atmosphere to form a modified cellulose solution; and adjusting the modified cellulose solution to a second temperature.

According to an aspect of the above embodiment, the first temperature is from about 115° C. to about 145° C. and the second temperature is from about 90° C. to about 120° C.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

In one embodiment, the present disclosure also provides a microsphere including: a shell including a first biodegradable polymer encapsulating at least one of a bioactive agent or a visualization agent and at least one second microsphere, the at least one second microsphere including a second biodegradable polymer and at least one magnetic material.

According to an aspect of the above embodiment, the first biodegradable polymer and the second biodegradable polymer are different and at least one of the first biodegradable polymer or the second biodegradable polymer is modified cellulose.

According to an aspect of the above embodiment, at least one of the first biodegradable polymer or the second biodegradable polymer is an aliphatic polyester.

According to an aspect of the above embodiment, the aliphatic polyester is selected from the group consisting of polylactide, polylactide-co-glycolide, polylactide-polycaprolactone, and combinations thereof.

According to an aspect of the above embodiment, the at least one magnetic material includes a particle selected from the group consisting of ferrite, strontium ferrous oxide, neodymium, samarium, cobalt, aluminum, nickel, copper, iron, titanium, and combinations thereof.

According to an aspect of the above embodiment, the first biodegradable polymer encapsulates at least one second microsphere, the at least one second microsphere including at least one of the bioactive agent or the visualization agent.

In one embodiment, the present disclosure also provides a microsphere including: modified cellulose; and at least one radioactive material.

According to an aspect of the above embodiment, the at least one radioactive material is a radioactive isotope selected from the group consisting of yttrium, iodine, holmium, and combinations thereof.

In one embodiment, the present disclosure also provides a method including: contacting a modified cellulose solution including a solvent with at least one radioactive material to form a discontinuous phase liquid; contacting the discontinuous phase liquid with a continuous phase liquid to form an emulsion; and contacting the emulsion with a third phase liquid to extract the solvent from the emulsion thereby forming a plurality of microspheres.

According to an aspect of the above embodiment, the third phase liquid is miscible with the continuous composition and the discontinuous composition.

According to an aspect of the above embodiment, the third phase liquid is selected from the group consisting of isopropyl myristate, hexane, triglycerides and combinations thereof.

According to an aspect of the above embodiment, the third phase liquid is present in an amount from about 300% by volume to about 200% by volume of the continuous phase liquid.

According to an aspect of the above embodiment, the formation of the modified cellulose solution includes: contacting a modified cellulose with the solvent under an inert atmosphere to form a swelled modified cellulose; adjusting the swelled modified cellulose mixture to a first temperature; contacting the swelled modified cellulose after adjusting the first temperature with a salt under the inert atmosphere to form a modified cellulose solution; and adjusting the modified cellulose solution to a second temperature.

According to an aspect of the above embodiment, the first temperature is from about 115° C. to about 145° C. and the second temperature is from about 90° C. to about 120° C.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

In one embodiment, the present disclosure also provides a microsphere including: a first biodegradable polymer encapsulating at least one second microsphere, the at least one second microsphere including a second biodegradable polymer and at least one radioactive material.

According to an aspect of the above embodiment, the first biodegradable polymer and the second biodegradable polymer are the same.

According to an aspect of the above embodiment, the first biodegradable polymer and the second biodegradable polymer are modified cellulose.

According to an aspect of the above embodiment, the first biodegradable polymer and the second biodegradable polymer are different and at least one of the first biodegradable polymer or the second biodegradable polymer is modified cellulose.

According to an aspect of the above embodiment, at least one of the first biodegradable polymer or the second biodegradable polymer is an aliphatic polyester.

According to an aspect of the above embodiment, the aliphatic polyester is selected from the group consisting of polylactide, polylactide-co-glycolide, polylactide-polycaprolactone, and combinations thereof.

According to an aspect of the above embodiment, the microsphere further includes at least one magnetic material.

According to an aspect of the above embodiment, wherein the at least one magnetic material includes a particle selected from the group consisting of ferrite, strontium ferrous oxide, neodymium, samarium, cobalt, aluminum, nickel, copper, iron, titanium, and combinations thereof.

In one embodiment, the present disclosure also provides a microsphere including: modified cellulose; at least one second microsphere including at least one first reactant; and at least one third microsphere including at least one second reactant, wherein the at least one second reactant is reactable with the at least one first reactant exothermically or endothermically.

According to an aspect of the above embodiment, the at least one first reactant and the at least one second reactant are exothermic reactants and are selected from the group consisting of an acid, a salt, water, calcium oxide, and combinations thereof.

According to an aspect of the above embodiment, the at least one first reactant and the at least one second reactant are endothermic reactants and are selected from the group consisting of ethanoic acid, sodium carbonate, calcium carbonate, and combinations thereof.

According to an aspect of the above embodiment, the at least one second microsphere and the at least one third microsphere include a first biodegradable polymer other than modified cellulose.

According to an aspect of the above embodiment, the first biodegradable polymer is an aliphatic polyester selected from the group consisting of polylactide, polylactide-co-glycolide, polylactide-polycaprolactone, and combinations thereof.

In one embodiment, the present disclosure also provides a method including: contacting a modified cellulose solution including a solvent with at least one first reactant selected from the group consisting of an exothermic reactant and an endothermic reactant or at least one second reactant selected from the group consisting of an exothermic reactant and an endothermic reactant to form a discontinuous phase liquid; contacting the discontinuous phase liquid with a continuous phase liquid to form an emulsion; and contacting the emulsion with a third phase liquid to extract the solvent from the emulsion thereby forming a plurality of microspheres.

According to an aspect of the above embodiment, the third phase liquid is miscible with the continuous composition and the discontinuous composition.

According to an aspect of the above embodiment, the third phase liquid is selected from the group consisting of isopropyl myristate, hexane, triglycerides and combinations thereof.

According to an aspect of the above embodiment, the third phase liquid is present in an amount from about 130% by volume to about 170% by volume of the continuous phase liquid.

According to an aspect of the above embodiment, the formation of the modified cellulose solution includes: contacting a modified cellulose with the solvent under an inert atmosphere to form a swelled modified cellulose; adjusting the swelled modified cellulose mixture to a first temperature; contacting the swelled modified cellulose after adjusting the first temperature with a salt under the inert atmosphere to form a modified cellulose solution; and adjusting the modified cellulose solution to a second temperature.

According to an aspect of the above embodiment, the first temperature is from about 115° C. to about 145° C. and the second temperature is from about 90° C. to about 120° C.

According to an aspect of the above embodiment, the solvent is selected from the group consisting of N,N-Dimethylacetamide, N-methyl-2-pyrrolidinone, and combinations thereof.

According to an aspect of the above embodiment, the salt is selected from the group consisting of lithium halides, sodium halides, potassium halides, and combinations thereof.

In one embodiment, the present disclosure also provides a microsphere including: a shell including a first biodegradable polymer encapsulating at least one second microsphere, the at least one second microsphere including a second biodegradable polymer and at least one first reactant and at least one third microsphere including the second biodegradable polymer and at least one second reactant reactable with the at least one first reactant exothermically or endothermically.

According to an aspect of the above embodiment, the first biodegradable polymer and the second biodegradable polymer are different and at least one of the first biodegradable polymer or the second biodegradable polymer is modified cellulose.

According to an aspect of the above embodiment, at least one of the first biodegradable polymer or the second biodegradable polymer is an aliphatic polyester.

According to an aspect of the above embodiment, the aliphatic polyester is selected from the group consisting of polylactide, polylactide-co-glycolide, polylactide-polycaprolactone, and combinations thereof.

According to an aspect of the above embodiment, the at least one first reactant and the at least one second reactant are exothermic reactants and are selected from the group consisting of an acid, a salt, water, calcium oxide, and combinations thereof.

According to an aspect of the above embodiment, the at least one first reactant and the at least one second reactant are endothermic reactants and are selected from the group consisting of ethanoic acid, sodium carbonate, calcium carbonate, and combinations thereof.

BRIEF DESCRIPTION OF DRAWINGS

Various embodiments of the present disclosure will be described herein below with reference to the figures wherein.

DETAILED DESCRIPTION OF THE EMBODIMENTS

The present disclosure provides a system and method for dissolving cellulose. In embodiments, the present disclosure provides a process using a polar aprotic solvent and a salt, which is added in a step-wise manner to dissolve oxidized or non-modified cellulose. The dissolution process according to the present disclosure minimizes degradation of the oxidized cellulose, by conducting the process in an inert and dry atmosphere, introducing the salt in a specific sequence, heating the solution at a predetermined temperature and time, and minimizing shearing forces on the solution.

As described herein, cellulose includes natural (e.g., non-modified) or modified (e.g., treated) celluloses including, but not limited to, oxidized cellulose, alkyl celluloses, hydroxyalkyl celluloses, cellulose ethers, cellulose esters, nitrocelluloses, combinations thereof, and the like. Additional examples of suitable modified cellulose derivatives include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt.

As used herein, oxidized cellulose denotes cellulose having at least a portion of hydroxyl groups replaced by carboxyl, aldehyde, and/or ketone groups by oxidation. Oxidized cellulose may be formed using any technique within the purview of those skilled in the art. For example, cellulose may be oxidized by exposing it to an oxidation medium, such as a densified or supercritical fluid including, but not limited to, nitrogen dioxide, carbon dioxide, combinations thereof, and the like. In embodiments, the oxidation medium may include a combination of densified or supercritical fluids, such as nitrogen dioxide dissolved in carbon dioxide. The cellulose material may be exposed to the oxidizing medium for a period of time of from about 20 minutes to about 24 hours, in embodiments from about 1 hour to about 5 hours, at a temperature from about 20° C. to about 60° C., in embodiments from about 30° C. to about 45° C., and at a pressure of from about 20 bars to about 250 bars, in embodiments from about 30 bars to about 90 bars. Methods for oxidizing cellulose materials using densified fluids are disclosed, for example, in U.S. Patent Application Publication No. 2008/0194805, the entire disclosure which is incorporated by reference herein. Other methods for preparing oxidized cellulose materials are also disclosed, for example, in U.S. Pat. Nos. 3,364,200; 4,626,253; 5,484,913; and 6,500,777, the entire disclosures, of each of which are incorporated by reference herein.

Figure 1:
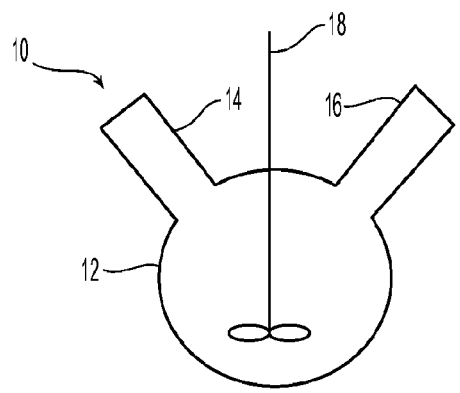
FIG. 1 is a schematic diagram of a system for dissolving cellulose in accordance with the present disclosure.

Turning now to FIG. 1, a system for dissolving cellulose, including oxidized cellulose, in accordance with the present disclosure is provided. System 10 includes a reactor vessel 12, which may be a three-neck round-bottom flask. The reactor vessel 12 includes a gas inlet 14 and a gas outlet 16, both of which are coupled to a source of inert gas (not shown). The reactor vessel 12 may also include any number of inlets, spigots, and other connectors to provide for convenient addition of reactants and/or removal of products to or from the vessel 12, respectively. Dissolution of the oxidized cellulose may be carried out either as a continuous process or a batch process.

The dissolution process is performed in an inert, i.e., oxygen free, and dry atmosphere. In embodiments, the reactor vessel 12 may be purged with an inert gas prior to commencing the dissolution process by circulating an inert gas through the reactor vessel 12 via the inlet 14 and outlet 16. The gas may also be circulated through the reactor vessel 12 during the dissolution process. Suitable inert gases include, but are not limited to, nitrogen and noble gases such as helium, neon, argon, and combinations thereof.

Initially, a solvent is added to the reactor vessel 12 through any suitable inlet. In embodiments, the solvent for dissolving oxidized cellulose may be any polar aprotic organic solvent having a boiling point from about 175° C. to about 205° C., in embodiments from about 180° C. to about 202° C. Suitable solvents include, but are not limited to, N,N-Dimethylacetamide, N-methyl-2-pyrrolidinone (NMP), and combinations thereof.

The solvent may also be sparged (e.g., gas bubbled therethrough) by the inert gas to exclude moisture and dissolved oxygen therefrom. Cellulose is then added to the solvent and may be agitated by a mixer 18 to swell the cellulose. Mixing is performed at a relatively low rate to prevent degradation of the cellulose. The stirring may be from about 100 revolutions per minute (rpm) to about 500 rpm, in embodiments from about 150 rpm to about 250 rpm. As described above, the reactor vessel 12 may be a round-bottomed container, which further minimizes the shearing forces imparted on the cellulose by the mixer 18.

The mixture of the solvent and oxidized cellulose may be heated to a temperature from about 115° C. to about 145° C., in embodiments from about 120° C. to about 140° C. in further embodiments from about 130° C. to about 135° C. In embodiments, the degree of oxidation of oxidized cellulose dissolved using the processes in accordance with the present disclosure may be from about 0.2 to about 1.0, in embodiments from about 0.3 to about 0.9, in further embodiments from about 0.5 to about 0.7. As used herein, the term "degree of oxidation" refers to a ratio of carboxyl groups to hydroxyl groups of the cellulose. The "degree of oxidation" is also used as an average degree of oxidation of the entire cellulose sample. Without being bound by any particular theory, it is believed that the temperature of the mixture of the solvent and oxidized cellulose depends on the degree of oxidation of the oxidized cellulose. As the degree of oxidation increases, the temperature required to swell oxidized cellulose decreases. Conversely, as the degree of oxidation decreases, the temperature required to swell oxidized cellulose increases. Heating of the cellulose during the dissolution process is minimized. Heating of the cellulose may lead to degradation thereof, including destruction of reactive groups of oxidized cellulose and decrease in molecular weight.

The mixture of the solvent and oxidized cellulose having a degree of oxidation of about 0.5 or above may be heated to a temperature from about 115° C. to about 135° C., in embodiments from about 125° C. to about 130° C. The mixture of the solvent and oxidized cellulose having a degree of oxidation of from about 0.25 to about 0.5 may be heated to a temperature from about 130° C. to about 145° C., in embodiments from about 135° C. to about 140° C.

The solvent initially swells the cellulose due to its relatively high polarity. Swelling of oxidized cellulose may continue from about 1 hour to about 4 hours, in embodiments from about 1.5 hours to about 2.5 hours. After the oxidized cellulose has swelled, the temperature of the mixture is reduced. In embodiments, the mixture of oxidized cellulose may be cooled prior to addition of the salt to a temperature from about 90° C. to about 120° C., in embodiments from about 100° C. to about 110° C.

Without being bound by any particular theory, it is believed that introduction of the salt into the mixture provides intercalation of the salt into the cellulose. The swelling of the cellulose with the solvent enhances the introduction of the salt into the cellulose, which in turn, affects final dissolution of the cellulose. In embodiments, the salt may be any alkali halide salt. Suitable salts include, but are not limited to, lithium halides, such as lithium fluoride, lithium chloride, lithium bromide, and lithium iodide; sodium halides, such as sodium fluoride, sodium chloride, sodium bromide, and sodium iodide; potassium halides, such as potassium fluoride, potassium chloride, potassium bromide, and potassium iodide; and any combinations of the foregoing. The salt may be present in an amount of from about 0.1% by weight to 3% by weight of the oxidized cellulose, in embodiments from about 0.25% by weight to about 2% by weight of the oxidized cellulose. Conventional dissolution processes rely on higher salt concentration to dissolve non-modified cellulose, which are unsuitable for dissolving oxidized cellulose. Lower concentration of salt prevents or lessens degradation of oxidized cellulose including destruction of reactive groups of oxidized cellulose and decrease in molecular weight as described above. As used herein, designation of "by weight" may be used interchangeably with "by volume" and denotes "by weight/volume."

Conducting the dissolution process in a step-wise manner, namely, initial swelling of the cellulose in the solvent prior to introduction of the salt, allows for dissolution of the cellulose at lower temperatures than conventional processes, which usually require temperatures above 150° C. The step-wise dissolution process at lower temperatures also prevents or lessens degradation of oxidized cellulose including destruction of reactive groups of oxidized cellulose and decrease in molecular weight as described above. In embodiments, the degree of oxidation of the dissolved oxidized cellulose may be from about 80% to about 120% of the degree of oxidation of the pre-processed, i.e., undissolved, oxidized cellulose, in embodiments from about 90% to about 110%. In embodiments, the molecular weight of the dissolved oxidized cellulose may be from about 80% to about 100% of the molecular weight of the pre-processed, i.e., undissolved, oxidized cellulose, in embodiments from about 90% to about 95%. As used herein, the term "molecular weight" refers to weight average molecular weight (Mw) of the cellulose. This term "molecular weight" is also used as an average molecular mass of the entire cellulose sample. Undissolved (e.g., prior to dissolution) oxidized cellulose may have a molecular weight from about 50,000 Daltons to about 500,000 Daltons, in embodiments from about 100,000 Daltons to about 400,000 Daltons.

If the oxidized cellulose is not fully dissolved, the process may continue with stirring and heating at a lower temperature from about 40° C. to about 80° C., in embodiments from about 50° C. to about 60° C., for a period of time from about 1 hour to about 5 hours, in embodiments from about 2 hours to about 3 hours, until the oxidized cellulose is dissolved. The resulting solution of oxidized cellulose includes oxidized cellulose present at a concentration of from about 5 milligrams per milliliter (mg/mL) to about 25 mg/mL, in embodiments from about 10 mg/mL to about 20 mg/mL.

The system of FIG. 1 may also be used to dissolve non-modified cellulose. The process for dissolving non-modified cellulose may utilize the same solvents as described above for dissolving oxidized cellulose. Initially, the non-modified cellulose is swelled in the solvent. The mixture of the solvent and non-modified cellulose may be heated to a temperature from about 135° C. to about 165° C., in embodiments from about 145° C. to about 155° C. The solvent initially swells the cellulose due to its relatively high polarity. Swelling of non-modified cellulose may continue from about 1 hour to about 4 hours, in embodiments from about 1.5 hours to about 2.5 hours. After the non-modified cellulose has swelled, the temperature of the mixture is reduced. In embodiments, the mixture of non-modified cellulose may be cooled prior to addition of the salt to a temperature from about 140° C. to about 160° C., in embodiments from about 145° C. to about 155° C.

The salt may be present in an amount of from about 0.1% by weight to 10% by weight of the non-modified cellulose, in embodiments from about 0.5% by weight to about 9% by weight of the non-modified cellulose. If the non-modified cellulose is not fully dissolved, the process may continue with stirring and heating at a lower temperature, from about 40° C. to about 80° C., in embodiments from about 50° C. to about 60° C., for a period of time from about 12 hours to about 36 hours, in embodiments from about 16 hours to about 24 hours, until the non-modified cellulose is dissolved.

The dissolved oxidized cellulose may then be used to form macro, micro or nanoparticles. In the present application, the terms "macroparticles," "macrospheres," "macrocapsules," "microparticles," "microspheres," "microcapsules," "nanoparticles," "nanospheres," and "nanocapsules" are used interchangeably and denote any particle having any regular or irregular shape and size from about 0.001 μm to about 2 mm, in embodiments from about 0.01 μm to about 1 mm.

Particle formation may be carried out either in as a continuous process with the dissolution process (e.g., subjecting the solution to high shearing forces, adding neutralizing agents, and/or adding cations) or a batch process. In embodiments, cellulose particles may be formed by subjecting the dissolved cellulose to high shearing forces (e.g., in a high-shear apparatus such as a mixer, extruder, and the like) in the presence of a solvent or non-solvent, a neutralizing agent, an aqueous solution having multivalent cations, and combination thereof.

The term "non-solvent", as used herein, is used in its broadest sense and includes any substance or mixture of substances in which cellulose is not soluble. Suitable solvents and co-solvents include, but are not limited to, NMP, DMAc and aqueous solutions, and combinations thereof. Suitable non-solvents include, but are not limited to, alkanes, oils glycerins, glycols, and combinations thereof. The solvent or non-solvent may be present in an amount of from about 1% by weight to 45% by weight of the cellulose, in embodiments from about 5% by weight to about 30% by weight of the cellulose, in embodiments from about 10% by weight to 20% by weight of the cellulose.

In embodiments, oxidized cellulose particles may be formed by contacting the dissolved cellulose with an aqueous solution having a neutralizing agent. The dissolved cellulose and the aqueous neutralizing solution may also be subjected to high shearing forces. In embodiments, the neutralizing agent may be used to neutralize the pendant carboxyl acid groups in the cellulose to regulate the final particle size and morphology, so a neutralizing agent herein may also be referred to as a "basic neutralization agent." Any suitable basic neutralization reagent may be used in accordance with the present disclosure. In embodiments, suitable basic neutralization agents may include both inorganic basic agents and organic basic agents. Suitable basic agents may include ammonia, ammonium hydroxide, potassium hydroxide, sodium hydroxide, sodium carbonate, sodium bicarbonate, lithium hydroxide, potassium carbonate, potassium bicarbonate, combinations thereof, and the like. Suitable basic agents may also include monocyclic compounds and polycyclic compounds having at least one nitrogen atom, such as, for example, secondary amines, which include aziridines, azetidines, piperazines, piperidines, pyridines, bipyridines, terpyridines, dihydropyridines, morpholines, N-alkylmorpholines, 1,4-diazabicyclo[2.2.2]octanes, 1,8-diazabicycloundecanes, 1,8-diazabicycloundecenes, dimethylated pentylamines, trimethylated pentylamines, pyrimidines, pyrroles, pyrrolidines, pyrrolidinones, indoles, indolines, indanones, benzindazones, imidazoles, benzimidazoles, imidazolones, imidazolines, oxazoles, isoxazoles, oxazolines, oxadiazoles, thiadiazoles, carbazoles, quinolines, isoquinolines, naphthyridines, triazines, triazoles, tetrazoles, pyrazoles, pyrazolines, and combinations thereof. In embodiments, the monocyclic and polycyclic compounds may be unsubstituted or substituted at any carbon position on the ring.

The neutralizing agent may be utilized as a solid such as, for example, sodium hydroxide flakes and may be dissolved in water to form an aqueous solution. The neutralizing agent may be added to the oxidized cellulose such that the pH of the solution is from about 5 to about 9, in embodiments from about 6 to about 8. As noted above, the basic neutralization agent may be added to neutralize the cellulose possessing carboxylic acid groups (e.g., oxidized cellulose). Neutralization of the pendant carboxylic acids in the formation of cellulose particles by minimizing inter-particle repulsion from anionic charges of the carboxylic acid groups. The addition of the basic neutralization agent may thus raise the pH of an emulsion including a cellulose possessing acid groups to a pH of from about 5 to about 12, in embodiments, from about 6 to about 11.

In embodiments, oxidized cellulose particles may be formed by contacting the dissolved cellulose with an aqueous solution having multivalent cations, including divalent and trivalent cations. The dissolved cellulose and the cation solution may also be subjected to high shearing forces. In embodiments, cellulose particles may be formed by a continuous two-phase spray preparation, in which a cation solution is initially sprayed onto a subtracted followed by spraying of a dissolved cellulose solution. In further embodiments, a cationic solution may be combined with an oxidized cellulose solution to form cross-linked gels in situ as described in further detail below.

Suitable cations include, but are not limited to, those of calcium ($Ca^{+2}$), barium ($Ba^{+2}$), zinc ($Zn^{+2}$), magnesium ($Mg^{+2}$), iron ($Fe^{+2}$, $Fe^{+3}$), platinum ($Pe^{+4}$), chromium ($Cr^{+6}$), and combinations thereof. In embodiments, the cation may be introduced by dissolving a suitable salt of the cation, which include, but are not limited to, halides, sulfates, carbonates, phosphates, nitrates, nitrites, oxides, acetates, combinations thereof, and the like. The cations may be present in an amount of from about 0.01% by weight to 25% by weight of the oxidized cellulose, in embodiments from about 1% by weight to about 18% by weight of the cellulose, in embodiments from about 2% by weight to 15% by weight of the oxidized cellulose depending upon end use of the oxidized cellulose solution. Cations act as cross-linking agents by cross-linking pendant carboxylic groups disposed on oxidized cellulose thereby forming cellulose particles. A dual-compartment spraying device (e.g., microfluidizer) may be used which stores the aqueous cation solution and the oxidized cellulose solution, which ejects the solution contemporaneously thereby mixing the particles and forming particles that are deposited on a substrate (e.g., tissue). Applicators for mixing two components are disclosed in commonly-owned U.S. Pat. Nos. 7,611,494, 8,033,483, 8,152,777 and U.S. Patent Application Publication Nos. 2010/0065660 and 2010/0096481, the entire disclosures of all of which are incorporated by reference herein.

In embodiments, the degree of oxidation of the oxidized cellulose particles formed from the dissolved oxidized cellulose of the present disclosure may be from about 80% to about 120% of the degree of oxidation of the pre-processed, i.e., undissolved, oxidized cellulose, in embodiments from about 90% to about 110%. In embodiments, the molecular weight of the oxidized cellulose particles may be from about 80% to about 100% of the molecular weight of the pre-processed, i.e., undissolved, oxidized cellulose, in embodiments from about 90% to about 95%. Undissolved (e.g., prior to dissolution) oxidized cellulose may have a molecular weight from about 50,000 Daltons to about 500,000 Daltons, in embodiments from about 100,000 Daltons to about 400,000 Daltons.

The dissolved cellulose and/or cellulose particles may be used to form various medical devices suitable for a variety of surgical and wound applications. The medical devices according to the present disclosure may be any structure suitable for being attached or implanted into tissue, body organs or lumens, including, but not limited to, micro and nano-particles, woven and non-woven fabrics, coatings, patches, films, foams, slit sheets, pledgets, tissue grafts, stents, scaffolds, buttresses, wound dressings, meshes, and/or tissue reinforcements.

In embodiments, as noted above, one or more bioactive agents may be added to the solvent such that the bioactive agents are incorporated into the oxidized cellulose solution, which may then be used to form various medical devices. A variety of bioactive agents, including polar and non-polar compounds, are soluble in the solvents described-above suitable for forming oxidized cellulose solutions according to the present disclosure. In embodiments, the bioactive agent may also be added after the oxidized cellulose particles have been formed. The terms "bioactive agent" and "active therapeutic agent" (ATA) are used interchangeably and in its broadest sense include any substance or mixture of substances that have clinical use. Consequently, bioactive agents may or may not have pharmacological activity per se, e.g., a dye, or fragrance. Alternatively a bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present medical device in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the implantable medical device and the surrounding tissues opposite the target tissue. In addition, anti-adhesive agents may be used to prevent adhesions from forming between the coated implantable medical device and the packaging material. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins, such as vitamin A, B-12, C, D, combinations thereof, and the like; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents also include biologics and protein therapeutics, such as, viruses, bacteria, lipids, amino acids, cells, peptides, polypeptides and proteins, analogs, muteins, and active fragments thereof, such as immunoglobulins, antibodies, cytokines (e.g., lymphokines, monokines, chemokines), blood clotting factors, hemopoietic factors, interleukins (IL-2, IL-3, IL-4, IL-6), interferons (β-IFN, α-IFN, and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

The present disclosure also provides for compositions and methods of fabricating microspheres encapsulating one or more bioactive agents within the oxidized cellulose. Suitable bioactive agents are described in more detail above. Oxidized cellulose microspheres may have a theoretical bioactive agent loading from about 80% to about 120%, in embodiments from about 90% to about 110%, in further embodiments from about 95% to about 105%, in additional embodiments from about 98% to about 102%. Oxidized cellulose microspheres may have an actual bioactive agent loading from about 0.01% to about 99.99%, in embodiments from about 15% to about 85%, in further embodiments from about 25% to about 55%, in additional embodiments from about 40% to about 60%.

Soluble oxidized cellulose, by virtue of being dissolved in a polar solvent as described above, allows for formation of microspheres including hydrophilic bioactive agents encapsulated in the oxidized cellulose. This may be accomplished by using an oil-in-oil emulsion method followed by a solvent extraction step in extraction media. As used herein the term "emulsion" refers to a mixture of two or more liquids that are immiscible, in which one liquid form a continuous phase and the other liquid forms a discontinuous phase. As used herein the terms "discontinuous" and "disperse" phase are used interchangeably and refer to the compound being dispersed through the continuous phase and may include the bioactive agent, optional encapsulating polymer and/or corresponding solvent or solvating agent. As used herein the term "continuous" phase refers to a liquid, such as, oils, that are used to extract the solvent or solvating agent from the discontinuous phase. These liquids are usually immiscible with the solvent employed in the discontinuous phase. As used herein the terms "thinning agent" and "third" phase are used interchangeably and refer to a liquid that reduces the viscosity of the continuous phase, is miscible with the continuous phase and/or removes residual continuous phase from the surface of the microsphere. In embodiments, the thinning agent may be immiscible with the discontinuous phase. As used herein the term "oil-in-oil" emulsion denotes an emulsion in which both the continuous phase and the discontinuous phase are organic liquids.

In forming microspheres of soluble oxidized cellulose by an oil-in-oil solvent extraction method, one or more hydrophilic bioactive agents may be added to a solution of oxidized cellulose and are mixed sufficiently to ensure a uniform suspension or homogeneous solution. Oxidized cellulose may be present in the solution in an amount from about 0.01% by weight to 45% by weight of the solution, in embodiments, from about 1% by weight to about 30% by weight of the solution, in embodiments from about 5% by weight to 20% by weight of the solution.

The bioactive agent and oxidized cellulose solution forms the discontinuous phase, which is added drop-wise to a vessel including a liquid forming a continuous phase. The continuous phase liquid may be any suitable non-polar compound that is immiscible with the polar solvents used in forming the oxidized cellulose solution. Suitable continuous phase liquids include, but are not limited to, petroleum-based oils, such as light, medium or heavy mineral oils (e.g., mixtures of alkanes having from about 40 carbons to about 60 carbons), plant-based oils, such as cottonseed oil, silicone-based oils, and combinations thereof. In embodiments, the continuous phase may include two or more oils such as, for example, a heavy oil and a light oil, that compete for extraction of the discontinuous phase. In embodiments, the heavy oil and the light oil may be present at a ratio of from about 1:10 to about 10:1, in embodiments from about 1:3 to about 3:1. The discontinuous phase liquid may be present in an amount from about 1% by volume to about 50% by volume of the continuous phase liquid, in embodiments from about 5% to about 20%.

The vessel possessing the continuous phase may be fitted with a baffle. The vessel may include a mixer with an impeller configured to rotate at a rate of from about 25 rpm to about 60,000 rpm, in embodiments, from about 100 rpm to about 15,000 rpm, in further embodiments from about 250 rpm to about 5,000 rpm. The stirring may continue from about 5 seconds to about 4 hours, in embodiments, from about 15 seconds to about 1 hour. The rate of rotation may be adjusted to obtain desired particle size. Size of the microspheres may be tailored by modulating the duration and the speed of homogenization (e.g., stirring of the discontinuous and continuous phases), temperature and/or pressure, altering the ratio of continuous to discontinuous phases, the shear rate, and the molecular weight and concentrations of oxidized cellulose and bioactive agents.

Upon completing the transfer of the discontinuous phase solution into the continuous phase, a third phase liquid may be added to the emulsion to remove the solvent from the discontinuous phase liquid. Suitable third phase liquids include any compound which is miscible with both the continuous and discontinuous phase liquids. The extraction of the solvent occurs due to the solvent being immiscible in the continuous phase liquid but miscible in the third phase liquid. Suitable third phase liquids include isopropyl myristate, hexane, n-heptane, triglycerides and combinations thereof. The third phase liquid may be present in an amount from about 300% by volume to about 200% by volume of the continuous phase liquid, in embodiments from about 140% to about 150%.

Removal of the solvent from the continuous phase facilitates formation of microspheres including the bioactive agent encapsulated by the oxidized cellulose. The emulsion may be stirred from about 0.1 hour to about 24 hours, in embodiments from about 2 hours to about 5 hours, to aid in the extraction of the polar solvent from the microspheres. The microspheres may then be collected via filtration and washed (e.g., with n-heptane) to remove any trace of continuous and discontinuous phase liquids on the surface of the microspheres. The microspheres may then be collected and transferred into a glass scintillation vial under a nitrogen or argon overlay. In embodiments, microspheres may also be formed using spray dry and jet mill techniques.

The oxidized cellulose microspheres are also suitable for encapsulating hydrophilic drugs such as bupivacaine HCl as well as viruses, bacteria, amino acids, peptides, proteins, lipids, vaccines, and combinations thereof since the oil-in-oil emulsion does not react with the water barrier of these bioactive agents.

In other embodiments, the oxidized cellulose solution may also be used to form various types of fibers. In embodiments, fibers may be solid, hollow, porous, and combinations thereof. Fibers may be formed by any suitable method, including electrospinning, solution casting, extruding, and combinations thereof. The fibers formed from the oxidized cellulose solutions may be used to form a variety of medical devices. The medical devices according to the present disclosure may be any structure suitable for being attached or implanted into tissue. Suitable structures formed from the fibers include, for example, films, foams, slit sheets, pledgets, tissue grafts, stents, scaffolds, buttresses, wound dressings, meshes, and/or tissue reinforcements. In embodiments, the fibers may be used to form non-woven meshes or tapes, which may be used as passive hemostats. The non-woven structure of a fibrous mesh formed from an oxidized cellulose solution lends itself to use as a wound dressing, due to its ability to filter liquids and/or gases.

The oxidized cellulose solution may also be used to form films and/or coatings. Coatings or films may be formed by depositing the solution by itself or on a substrate solution-casting, dipping, layering, calendaring, spraying, and combinations thereof. The solvent evaporates, thereby forming the film or coating on a substrate. The films may be incorporated onto other medical devices by applying the solution to the surface of the device, or portion thereof, utilizing any suitable method within the purview of those skilled in the art.

In embodiments, the oxidized cellulose solution may be used to form a sprayable delivery vehicle. In further embodiments, the oxidized cellulose solution may be combined with a second composition that forms a gel or effects precipitation of the oxidized cellulose as described in further detail below.

The viscosity of the solution for forming fibers, films, and other medical devices may be adjusted to achieve a desired viscosity. This may be accomplished by adding one or more plasticizers. Examples of suitable plasticizers include any biocompatible plasticizer, such as lecithin, dibutyl sebacate, citric acid, alcohol esters, polyethylene glycol, polypropylene glycol, and combinations thereof.

Uses for medical devices formed from the dissolved oxidized cellulose include closing and healing visceral wall defects and incisions, including incisions due to the removal of tumors, wounds, anastomoses, and fistulae. The medical devices can improve the healing of a gastrointestinal anastomosis and may provide an effective approach for the management and prevention of fistula. The medical devices may also prevent complications of polypectomy (e.g., bleeding and perforation). In embodiments, the medical devices may be reinforced with a mesh (e.g., formed on a substrate mesh) for the treatment of inguinal hernia and/or incisional hernia.

The rate of in vitro and in vivo biodegradation of medical devices formed from oxidized cellulose may be regulated by controlling the initial degree of oxidation of the resultant (e.g., dissolved and processed) oxidized cellulose. The greater the degree of oxidation of the oxidized cellulose, the faster the rate of biodegradation in vitro and in vivo. The present disclosure provides for processes that minimize the degradation of the oxidized cellulose during the dissolution process, thereby providing for cellulose having a desired degree of oxidation. Further, biodegradability of cellulose may be controlled by adjusting the molecular weight and degree of oxidation during the dissolution to provide for predictably degrading oxidized cellulose having a predictable degradation profile. A predictable degradation profile denotes a known or predetermined rate of degradation that may be used to estimate the degradation duration of the oxidized cellulose. Dissolving and processing without materially affecting the degree of oxidation allows for predictable biodegradability of the final products (e.g., medical devices). Thus, control of the rate of degradation of the oxidized cellulose matrix may be accomplished by varying the degree of oxidation, thereby controlling the rate of bioactive agent elution. The degree of oxidation of the oxidized cellulose may also be adjusted during the dissolution process to achieve a desired degree of oxidation.

Dissolved oxidized cellulose may also be utilized to form in situ gels. Oxidized cellulose solution may be prepared using the methods, e.g., solvents, conditions, etc., outlined above. The oxidized cellulose solution may have a pH from about from about 7.0 to about 10.0, in embodiments from about 8.0 to about 9.5. The oxidized cellulose solution may be combined with a gelation composition that, upon contacting the oxidized cellulose solution, forms a gel. The gel may be used as an adhesive to seal tissue and/or to provide for delivery of bioactive agents as described in further detail below.

In embodiments, the oxidized cellulose solution may be combined with a cationic material, such as a cationic polysaccharide. In embodiments, the cationic polysaccharide may be chitosan, carboxymethyl chitin, guar gum, and combinations, optionally in solution. Chitosan is a natural linear co-polymer of N-acetyl D-glucosamine (acetylated unit) and D-glucosamine (non-acetylated unit). Chitosan may be produced by partial or full deacetylation of chitin. Chitin may be extracted from natural sources, e.g., squid, exoskeletons of crustaceans such as shrimp, or vegetable sources such as mushrooms. Chitosan may also be synthetically produced or synthesized by modified microorganisms such as bacteria.

The adhesion of chitosan with other polysaccharides, such as cellulose, includes different kinds of interactions, such as electrostatic interactions, hydrogen bonds, and hydrophobic interactions, resulting in ionic cross-linking with the oxidized cellulose. Chitosan, under certain circumstances, is a cationic polymer containing $NH_3^+$ groups. The positively charged primary amino groups of chitosan attract anionic groups of other polymers. Thus, chitosan and anionic polymers are able to form polyelectrolyte complexes. Polyelectrolyte complex formation may improve the mechanical properties of the polymers and lead to new structures, such as precipitates, films, fibers, and gels.

Adhesion of chitosan with other polymers may also be promoted by enhancing the mechanical properties of the formulation by creating covalent bonds between both the components of the adhesive formulation. Chitosan has $NH_2$ groups which can react covalently with carboxyl groups. Thus, chitosan may be mixed with functionalized polymers having carboxyl groups, such as oxidized cellulose.

The chitosan may have a molecular weight from about 1,000 g/mol to about 5,000,000 g/mol, in embodiments from about 5,000 g/mol to about 220,000 g/mol. In embodiments, chitosan has a high molecular weight (HMW) of from about 450,000 g/mol to about 550,000 g/mol. In other embodiments, chitosan has a low molecular weight (LMW) of from about 50,000 g/mol to about 150,000 g/mol.

A solution of chitosan may be prepared, in embodiments, by dissolving chitosan in distilled water with a stoichiometric amount of acid, such as HCl or acetic acid, to ensure the complete protonation of all $NH_2$ groups. The final solution may contain from about 0.5% (w/w) to about 5% (w/w) chitosan, in embodiments from about 2% (w/w) to about 4% (w/w) chitosan. The chitosan solution may have a pH from about from about 1.0 to about 7.0, in embodiments from about 2.0 to about 6.0. The lower pH of the chitosan solution allows for suspension of pH sensitive bioactive agents in one of the solutions, either oxidized cellulose or chitosan, without compromising the bioactivity of the pH sensitive bioactive agents.

In embodiments, bioactive agents, whose bioactivity is reduced or destroyed by high pH, such as chemotherapeutic encapsulated polypeptides, may be suspended in a chitosan solution and incorporated into an in-situ forming gel upon contact with an oxidized cellulose solution. This gel can be fixed onto a targeted site, such as organs, tissue, etc. and anchor the encapsulated peptide, which then can be released. The resulting gel may be either neutral pH upon formation, or the pH can be adjusted, using the pH of the chitosan solution or the oxidized cellulose solution, to provide a friendly pH environment for the bioactivity of the peptide to be maintained.

Another suitable composition for gelation with the oxidized cellulose solution includes an aqueous solution of multi-valent cations, which forms a gel by ionic cross-linking of the oxidized cellulose and cations. Suitable cations include, but are not limited to, those of calcium ($Ca^{+2}$), barium ($Ba^{+2}$), zinc ($Zn^{+2}$), magnesium ($Mg^{+2}$), iron ($Fe^{+2}$, $Fe^{+3}$), platinum ($Pt^{+4}$), chromium ($Cr^{+6}$), and combinations thereof. In embodiments, the cations may be introduced by dissolving a suitable salt of the cations, which include, but are not limited to, halides, sulfates, carbonates, phosphates, nitrates, nitrites, oxides, combinations thereof, and the like in a suitable solvent such as water, methanol, ethanol, and combinations thereof. The cations may be present in an amount of from about 0.01% by weight to 25% by weight of the solution, in embodiments from about 1% by weight to about 18% by weight of the solution, in embodiments from about 2% by weight to 15% by weight of the solution, to achieve a desired mix ratio with the oxidized cellulose solution. The oxidized cellulose solution and the cationic solution form a reversible, ionically cross-linked gel. In embodiments, the gel can be made reversible by the addition of anionic solutions including aqueous solutions having a pH of greater than 7.0, such as solutions of urea, ammonia, amino acids such as, lysine and glycine, anionic polysaccharides such as, alginate, dextran, carboxymethyl cellulose, and combinations thereof.

A solution of oxidized cellulose may also be contacted with a precipitation and/or gelation composition that forms a gel by dilution and/or precipitation of the oxidized cellulose. Precipitation may be accomplished by contacting the oxidized cellulose solution with a composition including a solvent or a non-solvent. Suitable gelation compositions include, but are not limited to, water, saline, phosphate buffered saline, and combinations thereof. In embodiments, an aqueous solution of carboxymethyl cellulose may also be used. Carboxymethyl cellulose ("CMC") may be present in the solution from about 0.5% by weight or volume to about 5% by weight or volume, in embodiments, from about 1% by weight or volume to about 2% by weight or volume.

In embodiments, an aqueous solution of any cross-linker having one or more primary amines including, but not limited to, trilysine, albumin, polyethylene glycol amine, and combinations thereof may be used as a precipitating gelation composition. In further embodiments, an aqueous solution of any suitable Schiff-base compound may also be used as a precipitating gelation composition. As used herein, the term "Schiff-base" compound denotes any compound having a functional group including a carbon-nitrogen double bond with the nitrogen atom connected to an aryl or an alkyl group having a general formula $R_1R_2C{=}NR_3$, where $R_3$ and at least one of $R_1$ or $R_2$ is an aryl or an alkyl group. Suitable Schiff-base compounds include, but are not limited to, amoxicillin, cephalexin, 2,2-dimethyl benzimidazoline, 2-methyl-2-ethyl benzimidazoline, 2-methyl-2-propyl benzimidazoline, 2-methyl-2-butyl benzimidazoline, 2-methyl-2-hexyl benzimidazoline, 2-methyl-2-decyl benzimidazoline, 2,2-dimethyl-5-methylbenzimidazoline, 2-methyl-2-butyl-6-methyl benzimidazoline, 2,2-diethyl benzimidazoline, 2,2-diethyl benzimidazoline, 2-ethyl-2-hexyl benzimidazoline, 2-methyl-2-isoamyl-5-methyl benzimidazoline, 2,2-dioctyl benzimidazoline, 2,2-didecyl benzimidazoline, 2-propyl-2-pentyl benzimidazoline, 2,2-diethyl-6-ethylbenzimidazoline, 2,2-dipropyl-5-isopropylbenzimidazoline, 2,2-dipropyl-5-methylbenzimidazoline, 2,2-dibutyl-6-methylbenzimidazoline, 2,2-dibutyl-6-dodecylbenzimidazoline, 2-methyl-2-propenyl benzimidazoline, 2-ethyl-2-propenyl-5-methylbenzimidazoline, 2-methyl-2-butenyl benzimidazoline, 2-ethyl-2-butenyl-6-methylbenzimidazoline, 2,2-dihexyl benzimidazoline, 2,2-dihexyl-5-methylbenzimidazoline, and combinations thereof. Contacting of Schiff-base compound and/or small molecule cross-linker solutions with the oxidized cellulose solution results in covalent cross-linking of the oxidized cellulose, which, in turn, produces the gel. In embodiments, the aqueous solution may include CMC as well as the Schiff-base compounds.

In embodiments, a solution of one or more acrylic polymers may also be used to precipitate oxidized cellulose to form gels according to the present disclosure. Suitable acrylic polymers include, but are not limited to, those based on methyl methacrylate, hydroxyethyl acrylate, hydroxyethyl methacrylate, glyceryl acrylate, glyceryl methacrylate, acrylic acid, methacrylic acid, acrylamide, methacrylamide, and combinations thereof. Suitable solvents include acetone, ethyl acetate, dimethyl ether, and combinations thereof.

Upon contact of the oxidized cellulose solution with the precipitating composition, the gel is formed in situ by the dilution of the solvent used to form the oxidized cellulose solution and the subsequent precipitation of the oxidized cellulose. Since the polar solvent of the oxidized cellulose solution is miscible with water and/or organic solvents described above, oxidized cellulose precipitates out in the form of a gel due to the dilution of the solvent.

In embodiments, the precipitating composition may include a bioactive agent, which may be suspended in the precipitating composition. In embodiments, the bioactive agent may be initially suspended in the precipitating composition as a plurality of microspheres as described above. The microspheres may then be re-suspended in either the oxidized cellulose composition and/or the gelation composition. The resulting oxidized cellulose gel prevents the migration of the microspheres from the target site.

As noted above, the gels formed by the solutions of oxidized cellulose and gelation compositions can be used to deliver bioactive agents to tissue or the gels may be used to form articles or coatings thereon containing bioactive agents. The gels anchor the bioactive agents, microspheres, microparticles, and combinations thereof, to target sites, e.g., organs, tissues, etc. Microspheres and microparticles containing bioactive agents may be formed using the methods described above by suspending desired bioactive agents in the oxidized cellulose solution prior to microsphere or microparticle formation. The resulting particles may be suspended in the oxidized cellulose solution, which then may be combined with the cationic and/or chitosan solutions. This may be utilized to secure bioactive agents at the desired sites, including chemotherapeutic agents (e.g., cis-diamminedichloroplatinum(II)) at tumor excision sites, to provide for sustained release of chemotherapeutic agents from the gel and/or the microparticles secured thereby.

The gelation compositions and/or oxidized cellulose solution may be in a liquid form and placed in a syringe or any other suitable delivery vehicle, such as a sprayer, for immediate or later use. The solutions may be placed in delivery vehicles of different volumes so as to reach a specific ratio of each component.

The solutions may be applied convergently to a desired tissue site to form a gel thereon. As used herein, the term "convergently" denotes at least partial overlap of the compositions being applied to the substrate (e.g., tissue, medical device, etc.) either during the application process (e.g., mid-stream) or on a surface of the substrate.

The solutions used to form the gel may also be directly coated on a substrate, such as a mesh. The substrate may be prepared by soaking it in the desired solutions and drying (e.g., in an oven or in a laminar flow hood). In embodiments, the process may be repeated several times to ensure a proper coating displaying the required adhesive properties for the selected indication of use, e.g., fixation of extraperitoneal or retroperitoneal meshes, skin flap closure, etc.

The ratio of each component may be adjusted to provide a desired formulation. Each formulation is characterized by its mix ratio (MR). As used herein, the term "mix ratio" means the amount of the compound and/or reactive groups responsible for gelation (e.g., free amine groups of chitosan and/or amount of cations) versus the amount of free carboxyl groups present on the oxidized cellulose. The mix ratio may be at least about 1, in embodiments from about 1 to about 40, in further embodiments from about 10 to about 30. In embodiments, each component of the gel may be diluted with a buffer prior to use for pH adjustment.

Figure 2:
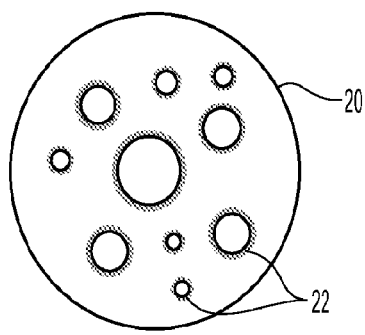
FIG. 2 is a schematic diagram of a doubly-encapsulated microsphere in accordance with the present disclosure.

The present disclosure also provides for compositions and methods of fabricating microspheres having additional microspheres therein encapsulating one or more APIs or bioactive agents. FIG. 2 shows a microsphere 20 having one or more microspheres 22 encapsulated therein. As used herein, "multi-encapsulated microspheres" denote the encapsulation of one or more smaller microspheres 22, e.g., particles, spheres, capsules, and combinations thereof in a single larger microsphere 20. In embodiments, multi-encapsulated microspheres may encapsulate one or more bioactive agents at same or different loading levels.

In a so-called "primary encapsulation," soluble oxidized cellulose may be used to encapsulate a bioactive agent, a water-soluble compound, a water-sensitive chemotherapeutic agent and/or active pharmaceutical ingredient, thereby forming oxidized cellulose microspheres, e.g., microspheres 22, as described above. Primary encapsulation with soluble oxidized cellulose may be carried out using emulsion-based solvent evaporation and/or extraction methods including, but not limited to, single-emulsion methods such as oil-in-water (o/w) and water-in-oil (w/o), double-emulsion methods such as water-in-oil-in-water (w/o/w) and solid-in-oil-in-water (s/o/w), and non-emulsion based methods, such as fluidized-bed, spray-drying, and casting/grinding methods. The primary oxidized cellulose microspheres may then be further encapsulated in a second layer of oxidized cellulose encapsulation, or in another biodegradable polymer, other than oxidized cellulose, in a so-called "secondary encapsulation" forming the microsphere 20 encapsulating the microspheres 22.

As used herein, the term "biodegradable" in reference to a material shall refer to the property of the material being able to be absorbed by the body. In the present application, the terms "biodegradable," "bioresorbable," "bioerodable," and "bioabsorbable" are used interchangeably and are intended to mean the characteristic according to which a material decomposes, or loses structural integrity under body conditions (e.g., enzymatic degradation or hydrolysis) or are broken down (physically or chemically) under physiologic conditions in the body, such that the degradation products are excretable or absorbable by the body after a given period of time. The time period may vary, from about one hour to about several months or more, depending on the chemical nature of the material. In embodiments, the material may not be completely absorbed, provided the non-absorbed material is acceptable for medical use.

Oxidized cellulose microspheres may be formed using oil-in-oil emulsification processes described above. The oxidized cellulose microspheres may then be further microencapsulated by using emulsion-based solvent evaporation methods, in which the oxidized cellulose microspheres are suspended in a solution of a biodegradable polymer or cross-linked and further encapsulated in another oxidized cellulose microencapsulation process. The solution may include any suitable biodegradable polymer, a solvent, and an optional emulsifier and/or a surfactant. In embodiments, additional bioactive agents may be added to the biodegradable polymer solution, which may be the same or different from the bioactive agent included in the oxidized cellulose microspheres. In further embodiments, some rounds of encapsulation may include no bioactive agents based on the desired use and/or performance characteristics of multi-encapsulated microspheres (e.g., altered release rate).

Suitable biodegradable polymers used to form microspheres according to the present disclosure include, but are not limited to, aliphatic polyesters, polyamides, polyamines, polyalkylene oxalates, poly(anhydrides), polyamidoesters, copoly(ether-esters), poly(carbonates) including tyrosine derived carbonates, poly(hydroxyalkanoates) such as poly (hydroxybutyric acid), poly(hydroxyvaleric acid), and poly (hydroxybutyrate), polyimide carbonates, poly(imino carbonates) such as such as poly(bisphenol A-iminocarbonate and the like), polyorthoesters, polyoxaesters including those containing amine groups, polyphosphazenes, poly(propylene fumarates), polyurethanes, polymer drugs such as polydiflunisol, polyaspirin, and protein therapeutics, biologically modified (e.g., protein, peptide) bioabsorbable polymers, and copolymers, block copolymers, homopolymers, blends, and combinations thereof.

More specifically, aliphatic polyesters include, but are not limited to, polylactide, polylactide-co-glycolide, polylactide-polycaprolactone, homopolymers and copolymers of lactide (including lactic acid, D-, L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, Δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, α,α diethylpropiolactone, ethylene carbonate, ethylene oxalate, 3-methyl-1,4-dioxane-2,5-dione, 3,3-diethyl-1,4-dioxan-2, 5-dione, 6,8-dioxabicycloctane-7-one, and polymer blends and copolymers thereof.

Suitable solvents for forming the biodegradable polymer solution of the discontinuous phase for secondary encapsulation include, but are not limited to, ethyl acetate, methylene chloride, perchloroethane, trichloroethylene, hexafluoroisopropanol (HFIP), chloroform, tetrahydrofuran, dimethyl formamide, as well as those pharmaceutical solvents listed in the ICH Q3C (International Conference on Harmonization—residual solvents used in pharmaceutical processing) and combinations thereof.

The emulsifier may be present in an amount from about 0.01% by weight and/or volume to about 25% by weight and/or volume of the solvent, in embodiments from about 0.1% by weight and/or volume to about 10% by weight and/or volume of the solvent, in further embodiments from about 0.5% by weight and/or volume to about 5% by weight and/or volume of the solvent. For oil-in-oil processes, the use of an emulsifier is optional. Suitable emulsifiers include, but are not limited to, water-soluble polymers, such as polyvinyl alcohol ("PVA"), polyvinyl pyrrolidone (PVP), polyethylene glycol (PEG), polypropylene glycol (PPG), PLURONICS™, TWEENS™, polysaccharides, phospholipids, and combinations thereof.

The continuous phase for the secondary encapsulation may also include a surfactant to stabilize the microspheres and adjust the bioactive agent loading efficiency. One, two, or more surfactants may be utilized. Examples surfactants that can be utilized include, for example, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy) ethanol, polyoxamers, combinations thereof, and the like.

Secondary encapsulation of oxidized cellulose microspheres may include cross-linking the microspheres to stabilize subsequent encapsulation and then forming a suspension of the microspheres in the biodegradable polymer solution described above. Oxidized cellulose microspheres may be cross-linked using any of the cationic species described above. The suspension may then be vortexed or intimately stirred to form an emulsion. In embodiments, the oxidized cellulose microspheres may be immediately suspended in the biodegradable polymer solution without cross-linking.

Emulsion-based solvent evaporation may be accomplished by stirring the suspension or emulsion at a rate from about 25 rpm to about 60,000 rpm, in embodiments, from about 100 rpm to about 15,000 rpm, in further embodiments from about 250 rpm to about 5,000 rpm. The emulsion may be stirred for a period of time from about 5 seconds to about 4 hours, in embodiments, from about 15 seconds to about 1 hour. Stirring may also be used to remove the discontinuous phase solvent from the emulsion, retaining the doubly-encased microspheres, or the multi-encased microspheres, i.e., the multi-encapsulated formulation.

For the second round of encapsulation, the solvent may be evaporated and/or extracted. After the solvent is evaporated and/or extracted, the emulsion retains the microspheres formed from the biodegradable polymer encapsulating the oxidized cellulose microspheres. The emulsion also includes free unencapsulated oxidized cellulose microspheres that are suspended in the emulsion. The size of the doubly-encased or multi-encased microspheres may be from about 0.001 µm to about 2 mm, in embodiments the size of the microspheres may be from about 0.01 µm to about 1 mm, in further embodiments the size of the microspheres may be from about 0.1 µm to about 500 µm. Size of the microspheres may be tailored by modulating the duration and the speed of stirring, temperature and/or pressure, altering the ratio of continuous to discontinuous phases, the shear rate created during stirring, and the molecular weight and concentrations of biodegradable polymers, emulsifiers, and surfactants, and other variables within purview of a person skilled in the art.

The primary encapsulation by the oxidized cellulose protects the bioactive agent from organic solvents and/or other conditions used in any subsequent rounds of encapsulation. Oxidized cellulosed may be used to encapsulate both hydrophilic and hydrophobic bioactive agents. While hydrophobic bioactive agents can also be encapsulated using emulsion methods including other biodegradable polymers, encapsulation of hydrophilic bioactive agents is particularly facilitated by dissolved oxidized cellulose.

Soluble oxidized cellulose, by virtue of being dissolved in a polar solvent as described above, allows for formation of microspheres including hydrophilic and/or hydrophobic bioactive agents encapsulated in the oxidized cellulose whereas other biodegradable polymers are better suited to encapsulate hydrophobic bioactive agents. Using oxidized cellulose for the first round of microencapsulation is beneficial since it does not dissolve in most polar or non-polar solvents, with the exception of solvents listed above with respect to dissolution of oxidized cellulose, thus eliminating the risk of microsphere dissolution during the second round of encapsulation. This allows for microencapsulation of both hydrophobic and hydrophilic bioactive agents, which can then be encapsulated into another microsphere.

In embodiments, the first layer of any microspheres may be formed using a biodegradable polymer other than oxidized cellulose using above-described encapsulation methods, which can then be further encapsulated in oxidized cellulose microspheres. Primary encapsulation of bioactive agents using biodegradable polymers may be carried out using emulsion-based solvent evaporation methods including, but not limited to, single-emulsion methods such as oil-in-water (o/w) and water-in-oil (w/o), double-emulsion methods such as water-in-oil-in-water (w/o/w) and solid-in-oil-in-water (s/o/w), and non-emulsion based methods, such as fluidized-bed, spray-drying, and casting/grinding methods.

Where a bioactive agent is first encapsulated in a biodegradable polymer, the bioactive agent may be dissolved in a solution to form a discontinuous phase. Suitable solvents for dissolving bioactive agents could be aqueous and/or organic and include water, saline, methylene chloride, chloroform, and alcohols, examples of which include methanol, ethanol, combinations thereof, and the like. Biodegradable polymer may also be dissolved to form a discontinuous phase using the solvents described above. Homogenization may be used for discontinuous phases if particle size reduction in the loading of the microsphere is desired. Homogenization may be carried by any suitable methods within the purview of one skilled in the art including, but not limited to, stirring, grinding, thermal energy, ultrasound energy, combinations thereof, and the like.

Emulsion-based solvent evaporation may be accomplished by stirring the suspension or emulsion at a rate from about 25 rpm to about 60,000 rpm, in embodiments, from about 100 rpm to about 15,000 rpm, in further embodiments from about 250 rpm to about 5,000 rpm. The emulsion may be stirred for a period of time from about 5 seconds to about 4 hours, in embodiments, from about 15 seconds to about 1 hour. Stirring may also be used to remove the discontinuous phase solvent from the emulsion, retaining the doubly-encased microspheres.

After the solvent is evaporated, the emulsion retains the microspheres formed from the biodegradable polymer encapsulating the bioactive agent. The emulsion also includes free unencapsulated portion of the bioactive agent that is suspended in the emulsion. The size of the microspheres may be from about 0.001 µm to about 2 mm, in embodiments the size of the microspheres may be from about 0.01 µm to about 1 mm, in further embodiments the size of the microspheres may be from about 0.1 µm to about 500 μm. Size of the microspheres may be tailored by modulating the duration and the speed of stirring, temperature and/or pressure, altering the ratio of continuous to discontinuous phases, the shear rate created during stirring, and the molecular weight and concentrations of biodegradable polymers, emulsifiers, and surfactants, and other variables within purview of a person skilled in the art.

The microspheres formed from the biodegradable polymers other than oxidized cellulose may then be suspended in a solution of oxidized cellulose, which is formed according to the processes described above. In forming microspheres of soluble oxidized cellulose by a solid-in-oil-in-oil solvent extraction method, the biodegradable polymer microspheres may be added to a solution of oxidized cellulose and are mixed sufficiently to ensure a uniform suspension. Oxidized cellulose may be present in the solution in an amount from about 0.01% by weight to 45% by weight of the solution, in embodiments, from about 1% by weight to about 30% by weight of the solution, in embodiments from about 5% by weight to 20% by weight of the solution. In embodiments, additional bioactive agents may be added to the oxidized cellulose solution which may be the same or different from the bioactive agents of the biodegradable polymer microspheres (e.g., hydrophilic vs hydrophobic bioactive agents).

The microspheres, the oxidized cellulose solution, and additional bioactive agents, if any, form the discontinuous phase, which is added drop-wise to a vessel including a liquid forming a continuous phase. The continuous phase liquid may be any suitable non-polar compound that is immiscible with the polar solvents used in forming the oxidized cellulose solution. Suitable continuous phase liquids include, but are not limited to, light, medium or heavy mineral oil (e.g., mixtures of alkanes having from about 40 carbons to about 60 carbons), cottonseed oil, and combinations thereof. Additional continuous phase may be added during emulsification. The discontinuous phase liquid may be present in an amount from about 2% by volume to about 40% by volume of the continuous phase liquid, in embodiments from about 5% to about 20%.

Emulsion-based solvent evaporation may be accomplished by stirring the suspension or emulsion at a rate from about 25 rpm to about 60,000 rpm, in embodiments, from about 100 rpm to about 15,000 rpm, in further embodiments from about 250 rpm to about 5,000 rpm. The emulsion may be stirred for a period of time from about 5 seconds to about 4 hours, in embodiments, from about 15 seconds to about 1 hour. Stirring may also be used to remove the discontinuous phase solvent from the emulsion, retaining the doubly-encased microspheres.

Upon completing the transfer of the discontinuous phase solution into the continuous phase, a third phase liquid may be added to the emulsion to remove or extract the solvent from the discontinuous phase liquid. Suitable third phase liquids include any compound which is miscible with the continuous and may be miscible with discontinuous phase solvent. The extraction of the solvent occurs due to the solvent being immiscible in the continuous phase liquid but miscible in the third phase liquid. Suitable third phase liquids include isopropyl myristate, hexane, triglycerides and combinations thereof. The third phase liquid may be present in an amount from about 300% by volume to about 200% by volume of the continuous phase liquid, in embodiments from about 140% to about 150%.

Extraction of the solvent from the discontinuous phase facilitates formation of doubly-encased microspheres including the bioactive agent encapsulated by a biodegradable polymer, other than oxidized cellulose and then further encapsulated by the oxidized cellulose. The emulsion may be stirred from about 0.1 hour to about 24 hours, in embodiments from about 2 hours to about 5 hours, to aid in the extraction of the polar solvent from the microspheres. The microspheres may then be collected via filtration and washed (e.g., with n-heptane) to remove any trace of continuous and discontinuous phase liquids on the surface of the microspheres. The microspheres may then be collected and transferred into a glass scintillation vial under a nitrogen or argon overlay. In embodiments, the microspheres may be cross-linked with a cationic solution and then dried.

Figure 3:
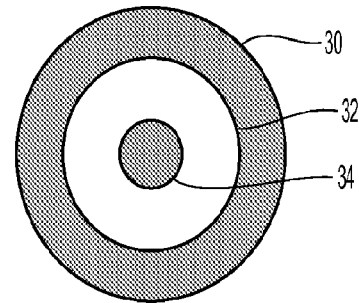
FIG. 3 is a schematic diagram of a multi-encapsulated microsphere in accordance with the present disclosure.

In further embodiments, as shown in FIG. 3, doubly-encapsulated microspheres 32, such as those encapsulating microspheres 34, may then be further encapsulated in either additional microspheres 30 formed from biodegradable polymer or the oxidized cellulose, depending on the material utilized in the second layer encapsulation. In other words, oxidized cellulose is utilized for every other (e.g., alternate) round of encapsulation (e.g., microspheres 30 and 34) with adjacent rounds (e.g., microsphere 32) being formed using biodegradable polymers other than oxidized cellulose. Thus, in embodiments where dissolved oxidized cellulose was used in the initial round of encapsulation (e.g., to form the microsphere 34), biodegradable polymers may be used for the second, (e.g., to form the microsphere 32) fourth, sixth, etc. rounds, and with oxidized cellulose being used in third (e.g., to form the microsphere 30), fifth, seventh, etc. rounds. Conversely, in embodiments where biodegradable polymers are used in the initial round of encapsulation (e.g., to form the microsphere 34), dissolved oxidized cellulose may be used for the second (e.g., to form the microsphere 32), fourth, sixth, etc. rounds, and with the biodegradable polymers being used in third (e.g., to form the microsphere 30), fifth, seventh, etc. rounds. Subsequent encapsulation using dissolved oxidized cellulose and/or biodegradable polymers may be carried out in the manner described above with respect corresponding encapsulation steps. In further embodiments, every multi-encapsulated layer may be formed from oxidized cellulose.

Figure 4:
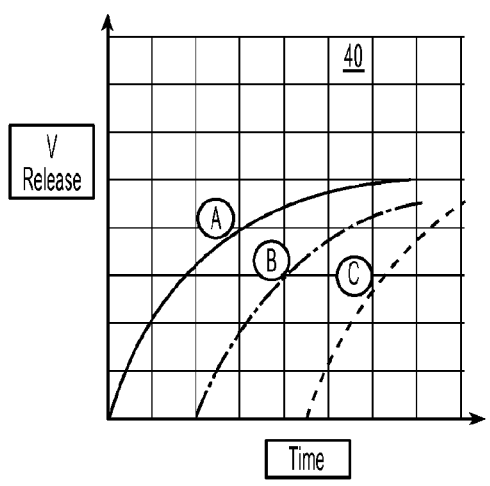
FIG. 4 is a plot of a release profile of a multi-encapsulated microsphere including a plurality of bioactive agents in accordance with the present disclosure.
Figure 5:
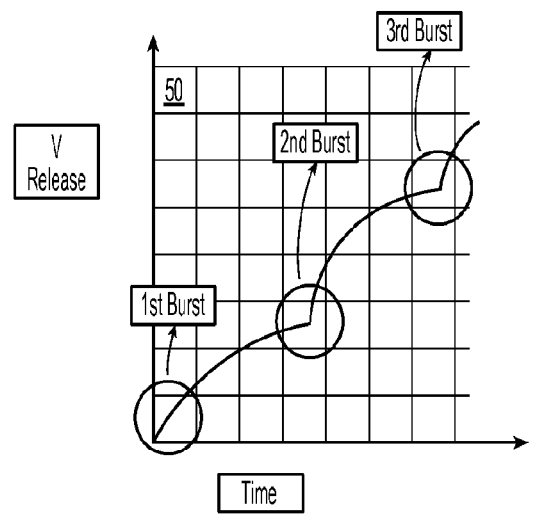
FIG. 5 is a plot of a release profile of a multi-encapsulated microsphere including a single bioactive agent in accordance with the present disclosure.

Multiple encapsulating microspheres offer several therapeutic advantages such as, for example, sequential release of multiple bioactive agents as illustrated in plots 40 and 50 of FIGS. 4 and 5. The plot 40 illustrate a release profile of a multi-encapsulated microsphere, e.g., microsphere 30, having three unique bioactive agents A, B, and C encapsulated within each of the microspheres 30, 32, 34, respectively. As the microsphere 30 degrades, the bioactive agent A is released, with the release profile decaying over time corresponding to the degradation of the microsphere 30. Thereafter, first encapsulated microsphere 32 begins to degrade, thereby releasing the bioactive agent B. Finally, the third bioactive agent C is released once the microsphere 34 commences degradation. Release profiles of each of the bioactive agents A, B, and C may be tailored by adjusting the amount of the encapsulation material (e.g., oxidized cellulose and/or biodegradable polymers). In embodiments, the release profiles may overlap such that one bioactive agent (e.g., A) is released concurrently with another bioactive agent (e.g., B). In further embodiments, the release profiles of each of the bioactive agents may be discrete (e.g., not overlapping) based on desired use and therapy requirements.

The plot 50 illustrates a release profile of a multi-encapsulated microsphere, e.g., microsphere 30, having the same bioactive agent A encapsulated within each of the microspheres 30, 32, 34. Unlike multiple release profiles of distinct bioactive agents A, B, C, encapsulating a single bioactive agent A provides a burst-like release profile, namely, increased dosages of the bioactive agent A are supplied as each of the microspheres 30, 32, 34 degrades. In addition, multiple layers provide an effective method to further slow-down in the release rate of the bioactive agent.

Multi-encapsulated microspheres provide unique advantages over conventional microspheres that encapsulate one or more bioactive agents in a single biodegradable microsphere. Encapsulating multiple bioactive agents in a single-layered microsphere formulation simply provides for simultaneous release of multiple bioactive agents, rather than for a staggered release profile as illustrated in FIG. 4. With respect to a single bioactive agent, a single-layered microsphere formulation is challenging in terms of providing burst and/or pulsatile release of bioactive agents during its degradation as illustrated in FIG. 5.

Multi-encapsulated microspheres provide for more effective bioactive agent loading. In embodiments, when a water-soluble hydrophilic bioactive agent is encapsulated in oxidized cellulose as the first layer of encapsulation using an oil-in-oil (o/o) emulsion solvent-evaporation method, the water-soluble hydrophilic bioactive agent is not lost in the oil-rich, hydrophobic surroundings and can therefore be effectively encapsulated in oxidized cellulose. During the second round of microencapsulation, e.g., with an oil in water o/w method, the water-soluble hydrophilic bioactive agent already has a protective layer, which again results in lower bioactive agent loss to the aqueous media, resulting in higher bioactive agent loading, following double encapsulation. The advantage of more effective bioactive agent loading is useful for encapsulating highly hydrophilic bioactive agent molecules. This is challenging to achieve with more conventional methods that employ single-layered encapsulation or those that employ polymers other than oxidized cellulose.

Multi-encapsulated microspheres further provide for additional protection of fragile, i.e. more vulnerable to environmental conditions, bioactive agents (e.g. biologics or protein therapeutics). Multi-encapsulation offers a significant advantage in controlling their release while keeping them active and protected from denaturation. This is possible for example when a first layer of encapsulation is put in place with oxidized cellulose, thus providing a protective barrier against any harsh conditions in the second (or subsequent) rounds of microencapsulation. This advantage opens up the possibility of effective encapsulation and controlled release of some very fragile biological therapeutics (e.g. protein therapeutics).

With respect to FIG. 2, multi-encapsulation also offers the ability for simultaneous release of multiple bioactive agents. Bioactive agents A, B, and C may be encapsulated individually in the microspheres 22, which are then encapsulated in the microsphere 20. This allows the bioactive agents A, B, and C to release simultaneously, while at the same time ensuring that these molecules do not interact with each other prior to release. Further, an outer encapsulation may be free of any bioactive agents and may act as a buffer, preventing release of bioactive agents until the outer encapsulation has biodegraded. Thus, multi-layered encapsulation using oxidized cellulose can facilitate more control over the timing release of the therapeutic payload.

Microspheres (e.g., single or multi-encapsulated microspheres) according to the present disclosure may also incorporate one or more visualization agents in presence or absence of the bioactive agents. Visualization agents may be encapsulated into single or multi-encapsulated microspheres using the methods and techniques described above with respect to bioactive agents. Suitable visualization agents may be selected from among any of the various non-toxic colored dyes suitable for use in tissue, such as FD&C Blue #1, FD&C Blue #2, FD&C Blue #3, D&C Green #6, methylene blue, indocyanine green, combinations thereof, and the like. In embodiments, additional visualization agents may be used, agents which are green or yellow fluorescent under visible light (e.g., fluorescein or eosin), x-ray contrast agents (e.g., iodinated compounds), ultrasonic contrast agents, MRI contrast agents (e.g., gadolinium containing compounds), CAT or CT scan contract agents (e.g., barium, barium sulphate, iodine, diatrizoic acid, available as GASTROGRAFIN®, etc.), radionucleotides (e.g., isotopes of technetium, iodine, indium, fluorine), combinations thereof, and the like. In further embodiments, the visualization agents may be magnetic materials suitable for tagging various compounds (e.g., cancer proteins) during assays. Suitable magnetic materials are described in further detail below.

With reference to FIG. 2, the microsphere 20 includes a shell encapsulating one or more smaller microspheres 22 therein. The microsphere 20 may include a first visualization agent while the microsphere 22 may include a second visualization agent, respectively, incorporated thereinto. The first and second visualization agents may be the same or different. In embodiments, the first and second visualization agents are different such that as the microspheres 20 are degraded after implantation, the first visualization agent is initially dispersed through the tissue in which the microsphere 20 is introduced, followed by the release of the second visualization agent due to the degradation of the microspheres 22. Sequential release of the first and second visualization agents occurs due to the degradation of the microsphere 20 prior to the degradation of the microsphere 22.

In addition to the first and second visualization agents, the microsphere 20 and the microspheres 22 may include first and second bioactive agents. The combination of the first and second visualization and first and second bioactive agents allows the healthcare professional to visualize/monitor progression, such as, track release rate, release sequence absorption, and other properties of the first and second bioactive agents. Further, this also allows for the monitoring of patient progress and the effectiveness of the bioactive agents.

Figure 6:
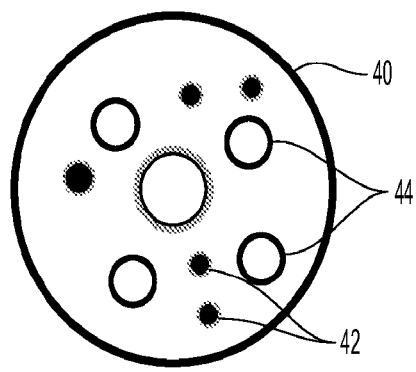
FIG. 6 is a schematic diagram of a multi-encapsulated microsphere including two types of microspheres in accordance with the present disclosure.

With reference to FIG. 6, another embodiment a multi-encapsulating microsphere 40 is shown. The microsphere 40 includes a shell encapsulating one or more smaller first microspheres 42 and one or more smaller second microspheres 44. The first and second microspheres 42 include first and second visualization agents and first and second bioactive agents, respectively. The first and second microspheres 42 and 44 may be formed separately prior to encapsulation within the microsphere 40. In embodiments, the microsphere 40 may include third visualization agent and third bioactive agent. Since the first and second microspheres 42 and 44 are encapsulated in the microsphere 40, the microspheres 42 and 44 begin to degrade concurrently. This allows for evaluation of the progress of the release of the first and second bioactive agents, by measuring the ratio of the first visualization agent to the second visualization agent. In embodiments, the microspheres 42 may include a first visualization agent and a first bioactive agent, while the microspheres 44 may include a second visualization agent and a second bioactive agent. Thus, the release of the first visualization agent corresponds to the release of the first bioactive agent and the release of the second visualization agent corresponds to the release of the second bioactive agent. In embodiments, the microspheres 42 and 44 may be prepared from the same or different materials to tailor absorption rate of the first and second visualization and/or bioactive agents.

In other embodiments, with reference to FIG. 3, a doubly-encapsulating microsphere 30 includes a microsphere 32, which further encapsulates microsphere 34 as described in more detail above. In one embodiment, the microsphere 30 and the microsphere 34 may include first and second bioactive agents, respectively. The microsphere 32 includes a first visualization agent. In this configuration, the first visualization may be used as a demarcation marker to indicate when the first bioactive agent of microsphere 30 has been released completely or mostly, prior to the release of the second bioactive agent from microsphere 34. Sequential release of the first and second bioactive agents occurs due to the degradation of the microsphere 30 prior to the degradation of the microsphere 32, followed by the degradation of the microsphere 34.

Figure 7:
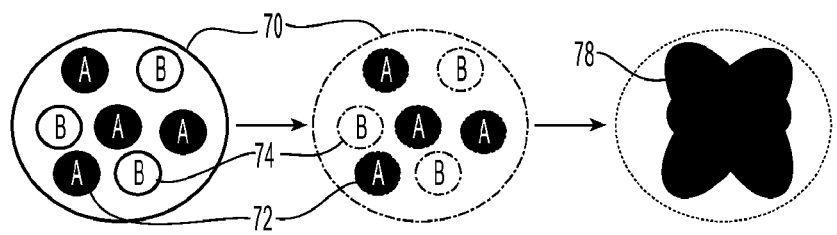
FIG. 7 is a schematic process diagram of multi-encapsulated microsphere including encapsulated first and second precursors in accordance with the present disclosure.

Microspheres (e.g., single or multi-encapsulated microspheres) according to the present disclosure may also incorporate one or more precursors (e.g., hydrogel or adhesive precursors) for forming compositions (e.g., hydrogels or adhesives) in situ. The hydrogel precursors may be in the presence or absence of the bioactive agents as described above. Hydrogel precursors may be encapsulated into single or multi-encapsulated microspheres using the methods and techniques described above with respect to bioactive agents. With reference to FIG. 7, a multi-encapsulating microsphere 70 is shown, having one or more first microspheres 72 including a first hydrogel precursor and one or more second microspheres 74 including a second hydrogel precursor. After implantation, the microsphere 70 prevents immediate polymerization or reaction of the first and second hydrogel precursors. After degradation of the microsphere 70, the microspheres 72 and 74 degrade, thereby releasing the first and second hydrogel precursors, which then react to form a hydrogel 78. In embodiments, the microsphere 70 may also include one or more initiators. Encapsulation of the first and second precursors allows for formation of a gel that is needed after a predetermined period of time, rather than immediately after introduction in vivo. The timing of the polymerization and/or activation may be controlled by adjusting the loading of the first and second precursors and/or the thickness of the microspheres, as well as other formulation characteristics.

Figure 8:
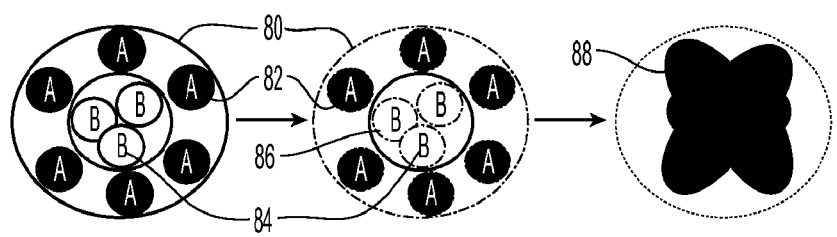
FIG. 8 is a schematic process diagram of multi-encapsulated microsphere including encapsulated first precursors and double-encapsulated second precursors in accordance with the present disclosure.

With reference to FIG. 8, a first multi-encapsulating microsphere 80 is shown, having one or more first microspheres 82 including a first hydrogel precursor and a second multi-encapsulating microsphere 86 including a third microsphere 84 having a second hydrogel precursor. After implantation, the microsphere 80 prevents immediate polymerization of the first and second hydrogel precursors. After degradation of the microsphere 80, the first microspheres 82 degrade, thereby releasing the first hydrogel precursors. The second multi-encapsulating microsphere 86 degrades concurrently with the first microspheres 82, delaying the release of the second hydrogel precursor contained within the second microspheres 84. In embodiments, the microspheres 80 and/or 86 may also include one or more initiators. This configuration delays the release of the second precursor, which also delays cross-linking of the precursors to form a hydrogel 88, which occurs only after the microspheres 84 have also degraded.

The above-described hydrogels may be formed from crosslinking the first and second precursors. The precursor may be a monomer or a macromer. As used herein the terms "hydrogel precursor(s)", "first hydrogel precursor", and "second hydrogel precursor" may be used to refer to components that may be combined to form a hydrogel, either with or without the use of an initiator. Thus, these precursors may, in embodiments, include combinations of reactive precursors and initiated precursors. As used herein the terms "reactive precursor(s)", "first reactive hydrogel precursor(s)", and "second reactive hydrogel precursor(s)" include precursors that may crosslink upon exposure to each other to form a hydrogel. As used herein the term "initiated precursor(s)", "first initiated hydrogel precursor(s)" and "second initiated hydrogel precursor(s)" may be used to describe first and second precursors that crosslink upon exposure to an external source, sometimes referred to herein as an "initiator". Initiators include, for example, ions, UV light, redox-reaction components, combinations thereof, as well as other initiators within the purview of those skilled in the art.

The first and second precursors, whether reactive precursors or initiated precursors, may have biologically inert and water soluble cores. When the core is a polymeric region that is water soluble, suitable polymers that may be used include: polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"), poly(vinyl pyrrolidinone) ("PVP"), poly (amino acids), poly(saccharides), such as dextran, chitosan, alginates, carboxymethylcellulose, oxidized cellulose, hydroxyethylcellulose and/or hydroxymethylcellulose, hyaluronic acid, and proteins such as albumin, collagen, casein, and gelatin. In embodiments, combinations of the foregoing polymeric materials may be utilized to form a core. The polyethers, and more particularly poly(oxyalkylenes) or poly(ethylene glycol) or polyethylene glycol ("PEG"), may be utilized in some embodiments.

When the core is small in molecular nature, any of a variety of hydrophilic functionalities may be used to make the first and second precursors water soluble. In embodiments, functional groups like hydroxyl, amine, sulfonate and carboxylate, may contribute to the water-solubility of a precursor. For example, the N-hydroxysuccinimide ("NHS") ester of subaric acid is insoluble in water, but by adding a sulfonate group to the succinimide ring, the NHS ester of subaric acid may be made water soluble, without affecting its ability to be used as a reactive group due to its reactivity towards amine groups.

In embodiments, a hydrogel may be formed from reactive precursors through covalent, ionic, or hydrophobic bonds. Physical (non-covalent) crosslinks may result from complexation, hydrogen bonding, desolvation, Van der Waals interactions, ionic bonding, combinations thereof, and the like, and may be initiated by mixing two precursors that are physically separated until combined in situ or as a consequence of a prevalent condition in the physiological environment, including temperature, pH, ionic strength, combinations thereof, and the like. Chemical (covalent) crosslinking may be accomplished by any of a number of mechanisms including, but not limited to, free radical polymerization, condensation polymerization, anionic or cationic polymerization, step growth polymerization, electrophile-nucleophile reactions, combinations thereof, and the like.

In embodiments, the reactive precursor portion of the hydrogel may be formed from a single type of reactive precursor or multiple types of reactive precursors. In other embodiments, where the hydrogel is formed from multiple types of reactive precursors, for example two reactive precursors, the reactive precursors may be referred to as a first and second reactive precursor. Where more than one reactive precursor is utilized, in embodiments, at least one of the first and second precursors may be a crosslinker, and at least one other reactive hydrogel precursor may be a macromolecule, and may be referred to herein as a "functional polymer".

In some embodiments, reactive precursors may include biocompatible multi-precursor systems that spontaneously crosslink when the precursors are mixed, but wherein the two or more precursors are individually stable for the duration of the deposition process. When the reactive precursors are mixed in an environment that permits reaction (e.g., as relating to pH or solvent), the functional groups react with each other to form covalent bonds. Reactive precursors become crosslinked when at least some of the reactive precursors can react with more than one other precursor. For instance, a precursor with two functional groups of a first type may be reacted with a crosslinking precursor that has at least three functional groups of a second type capable of reacting with the first type of functional groups.

Such reactive components include, for example, first reactive precursors possessing electrophilic groups and second reactive precursors possessing nucleophilic groups. Electrophiles react with nucleophiles to form covalent bonds. Covalent crosslinks or bonds refer to chemical groups formed by reaction of functional groups on different polymers that serve to covalently bind the different polymers to each other. In certain embodiments, a first set of electrophilic functional groups on a first reactive precursor may react with a second set of nucleophilic functional groups on a second reactive precursor. In embodiments, such systems include a first reactive precursor including di- or multifunctional alkylene oxide containing moieties, and a second reactive precursor including macromers that are di- or multifunctional amines.

In embodiments the first and second precursors may be multifunctional, meaning that they may include two or more electrophilic or nucleophilic functional groups, such that, for example, an electrophilic functional group on the first reactive hydrogel precursor may react with a nucleophilic functional group on the second reactive hydrogel precursor to form a covalent bond. At least one of the first or second precursors includes more than two functional groups, so that, as a result of electrophilic-nucleophilic reactions, the precursors combine to form crosslinked polymeric products.

In embodiments, each of the first and second precursors include only one category of functional groups, either only nucleophilic groups or only electrophilic functional groups, so long as both nucleophilic and electrophilic reactive precursors are used in the crosslinking reaction. Thus, for example, if the first reactive hydrogel precursor has electrophilic functional groups such as N-hydroxysuccinimides, the second reactive hydrogel precursor may have nucleophilic functional groups such as amines. On the other hand, if the first reactive hydrogel precursor has electrophilic functional groups such as sulfosuccinimides, then the second reactive hydrogel precursor may have nucleophilic functional groups such as amines or thiols.

In embodiments, a multifunctional electrophilic polymer such as a multi-arm PEG functionalized with multiple NHS groups may be used as a first reactive hydrogel precursor and a multifunctional nucleophilic polymer such as trilysine may be used as a second reactive hydrogel precursor. The multi-arm PEG functionalized with multiple NHS groups may, for example, have four, six or eight arms and a molecular weight of from about 5,000 to about 25,000. Other examples of suitable first and second precursors are described in U.S. Pat. Nos. 6,152,943, 6,165,201, 6,179,862, 6,514,534, 6,566,406, 6,605,294, 6,673,093, 6,703,047, 6,818,018, 7,009,034, and 7,347,850, the entire disclosures of each of which are incorporated by reference herein.

Synthetic materials that are readily sterilized and avoid the dangers of disease transmission that may accompany the use of natural materials may thus be used. Indeed, certain polymerizable hydrogels made using synthetic precursors are within the purview of those skilled in the art, e.g., as used in commercially available products such as FOCALSEAL® (Genzyme, Inc.), COSEAL® (Angiotech Pharmaceuticals), and DURASEAL® (Confluent Surgical, Inc). Other known hydrogels include, for example, those disclosed in U.S. Pat. Nos. 6,656,200, 5,874,500, 5,543,441, 5,514,379, 5,410,016, 5,162,430, 5,324,775, 5,752,974, and 5,550,187.

The reaction conditions for forming crosslinked polymeric hydrogels from first and second precursors may depend on the nature of the reactive precursor used as well as the surrounding environment. The first and second precursors may be stable and/or non-reactive at a given pH as they are encased within oxidized cellulose and/or another biodegradable polymer, but become reactive upon exposure the pH of the tissue pH. In embodiments, reactions may be conducted in buffered aqueous solutions at a pH of about 5 to about 12. Buffers include, for example, sodium borate buffer (pH 10) and triethanol amine buffer (pH 7). In some embodiments, organic solvents such as ethanol or isopropanol may be added to improve the reaction speed of the first and second precursors.

In embodiments, the multi-encapsulated microspheres may incorporate any other in situ polymerizable monomers suitable for forming biocompatible tissue implants, hydrogels and/or adhesives, such as α-cyanoacrylate monomers, 1,1-disubstituted ethylene monomers, combinations thereof, and the like.

Microspheres (e.g., single or multi-encapsulated microspheres) according to the present disclosure may also incorporate one or more magnetic materials allowing for guidance of the encapsulated microspheres through a patient's body. Magnetic materials may be encapsulated into single or multi-encapsulated microspheres using the methods and techniques described above with respect to bioactive agents. Multi-encapsulated microspheres may include magnetic materials encapsulated therein along with bioactive agents, visualization agents, cross-linking precursors, radioactive materials, and combinations thereof, as discussed in more detail below with respect to FIGS. 2, 3, 6, and 9. Multi-encapsulated microspheres permit sequestration of magnetic materials from other substances (e.g., bioactive agents, visualization agents, etc.) contained in the microspheres, thereby allowing for magnetic guidance of the microspheres to the tissue site of interest as described in further detail below.

Multi-encapsulated microspheres may be guided to a treatment site by injecting or otherwise delivering the microspheres into the patient (e.g., intravenously, orally, etc.). After delivery of the microspheres, the treatment site is subjected to one or more magnetic fields, which may be generated by any suitable permanent or temporary magnets (e.g., electromagnets). The magnetic fields retain the microspheres circulating through the patient within the treatment site, i.e., the area to which magnetic field is applied. The microspheres thereafter begin to biodegrade, delivering the materials encapsulated therein to the treatment site. Magnetic guidance allows for the concentration of bioactive agents at a predetermined target site, and away from other sites of the patient within healthy tissue.

Magnetic guidance provides for delivery of microspheres to specific locations in the body which are hard to reach using conventional delivery mechanisms (e.g., catheters). Magnetic guidance is possible with more than one layer of encapsulation containing a magnetic payload, thus allowing for more than one occasion of magnetic guidance as the layers erode and/or diffuse. The use of oxidized cellulose also lowers the possibility of rusting of the magnetic payload (e.g., iron containing payload) since the process of encapsulation in oxidized cellulose is an oil-in-oil process, i.e., a non-aqueous process. Magnetic Resonance Imaging (MRI) may also be facilitated with the magnetic materials. Complementary properties of more than one MRI agent could be combined in the same formulation because of the multiple layers of encapsulation.

With reference to FIG. 2, the multi-encapsulating microsphere 20 encapsulates a plurality of microspheres 22 therein. The microspheres 22 include one or more bioactive agents, visualization agents, and/or cross-linking precursors described above. The multi-encapsulating microsphere 20 further includes one or more magnetic materials.

With reference to FIG. 3, a doubly-encapsulating microsphere 30 includes a microsphere 32, which further encapsulates microsphere 34 as described in more detail above. In one embodiment, the microsphere 30 may include a first bioactive agent, visualization agent, and/or cross-linking precursor described above. The microsphere 32 includes a second bioactive agent, visualization agent, and/or cross-linking precursor. The microsphere 34 includes one or more magnetic materials. Encapsulation of the magnetic materials in the furthest encapsulated microsphere 34, allows for the magnetic materials to remain at the treatment site while doubly-encapsulating microsphere 30 degrades thereby releasing the first bioactive agent, visualization agent, and/or cross-linking precursor followed by the degradation of the single-encapsulating microsphere 34 thereby releasing the second bioactive agent, visualization agent, and/or cross-linking precursor.

With reference to FIG. 6, multi-encapsulating microsphere 40 is shown. The microsphere 40 includes one or more first microspheres 42 and one or more second microspheres 44. The first microspheres 42 may possess one or more bioactive agents, visualization agents, and/or cross-linking precursors described above. and the second microspheres 44 include one or more magnetic materials. Microspheres 42 and 44 may be encapsulated in the same layer or in multiple layers, which may be the same or different.

In embodiments, the microsphere 44 may also include magnetic materials, which allows for multiple opportunities of magnetic guidance. In particular, the microspheres 40 may be guided to a first treatment site, where the microsphere 40 degrades, thereby releasing the microspheres 42 and 44. The microspheres 42 remain in place, thereby releasing payload, while the microspheres 44, which include magnetic materials may be guided to a second treatment site. The microspheres 44 may optionally include a second bioactive agent, visualization agent, and/or cross-linking precursor described above. Once at the second treatment site, the microspheres 44 degrade thereby releasing its own payload.

Figure 9:
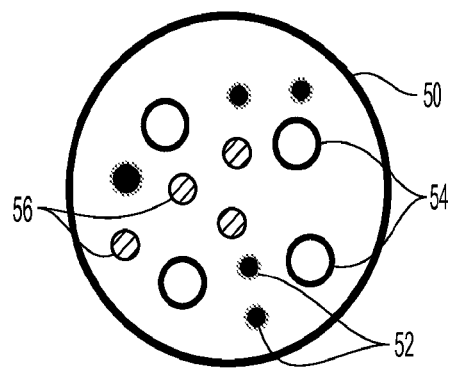
FIG. 9 is a schematic diagram of a multi-encapsulated microsphere including three types of microspheres in accordance with the present disclosure.

With reference to FIG. 9, another embodiment a multi-encapsulating microsphere 50 is shown. The microsphere 50 includes one or more first microspheres 52, one or more second microspheres 54, and one or more third microspheres 56. The first microspheres 52 may include one or more bioactive agents, the second microspheres 54 may include one or more magnetic materials, and the third microspheres 56 may include a visualization agent, or any other suitable material. The first microsphere 52, second microsphere 54, and third microsphere 56 may be formed separately prior to encapsulation within the microsphere 50. Microspheres 52, 54, 56 may be encapsulated in the same layer or in multiple layers, which may be the same or different.

Where utilized, suitable magnetic materials may be in particle form having a size from about 10 angstroms (Å) to about 1000 Å, in embodiments from about 25 Å to about 500 Å. Suitable magnetic materials may be temporary magnetic materials or permanent magnetic materials, ceramic, crystalline, or flexible magnetic materials (e.g., a polymeric substance such as thermoplastics or rubber) combined with magnetic ferrite (e.g., heat-treated mixtures of oxides of iron and one or more other metals having complex crystals with magnetic properties). Suitable magnetic materials include, but are not limited to, ferrite, strontium ferrous oxide, neodymium (NdFeB, optionally including dysprosium), samarium, cobalt, aluminum, nickel, copper, iron, titanium, and combinations thereof. In embodiments, the microspheres 22 may include magnetotactic bacteria having magnetosomes allowing the bacteria to orient within a magnetic field. In further embodiments, the magnetic material may be an alloy of a radioactive material such as yttrium-90, which is a β-emitter, making it suitable for radiation therapy treatment of various cancers as described in further detail below.

Microspheres (e.g., single or multi-encapsulated microspheres) according to the present disclosure may also incorporate one or more radioactive materials allowing the microspheres to be used in interventional oncology (e.g., radiotherapy). Radioactive materials may be encapsulated into single or multi-encapsulated microspheres using the methods and techniques described above with respect to bioactive agents. Suitable radioactive materials include, but are not limited to, yttrium (e.g., $^{90}Y$), iodine (e.g., $^{131}I$) holmium (e.g., $^{166}Ho$), combinations thereof, and the like. Microspheres containing radioactive materials may be formed by encapsulating the materials as described above. In embodiments, radioactive materials may be encapsulated in oxidized cellulose to form singly-encapsulated microspheres. In embodiments, the oxidized cellulose microspheres including radioactive materials may be further encapsulated in successive oxidized cellulose microspheres.

Once microspheres are formed, they are subjected to neutron bombardment prior to implantation within the patient to convert stable isotopes of the materials into radioactive materials suitable for radiotherapy (e.g., converting inert $^{89}Y$ into $^{90}Y$). The microspheres may be guided to the treatment site using any suitable methods (e.g., magnetic guidance as described above if magnetic materials are present). The microspheres may then deliver radiation therapy to the treatment site.

Neutron bombardment and/or other treatments may heat the microspheres up to 200° C., which causes degradation of many biodegradable polymers used to create microspheres, such as polylactide. Accordingly, conventional microspheres for delivering radioactive materials have been formed from non-biodegradable materials, such as glass. The present disclosure provides for single or multi-encapsulated microspheres formed from oxidized cellulose, which is a polymer capable of withstanding temperatures up to 200° C. Unlike glass microspheres, the microspheres of the present disclosure provide for delivery of the radioactive materials using biodegradable microspheres that degrade over time. Glass microspheres including radioactive materials are disclosed in S. Ho et al., "Clinical Evaluation Of The Partition Model For Estimating Radiation Doses From Yttrium-90 Microspheres In The Treatment Of Hepatic Cancer Evaluation Of The Partition Model For Estimating Radiation Doses From Yttrium-90 Micro Spheres In The Treatment Of Hepatic Cancer," European Journal of Nuclear Medicine, Vol. 24, No. 3, (March 1997), pp. 293-298.

Microspheres made with oxidized cellulose are lower in density than glass microspheres, which is an advantage for interventional oncology applications because high density microspheres result in intravascular settling. With respect to conventional encapsulation materials, multiple encapsulation of radioactive materials using oxidized cellulose as described herein prevents seepage and leakage of radioactive materials from the microspheres.

Microspheres (e.g., single or multi-encapsulated microspheres) according to the present disclosure may also incorporate one or more endothermic or exothermic agents. Endothermic or exothermic agents may be encapsulated into single or multi-encapsulated microspheres using the methods and techniques described above with respect to bioactive agents. Endothermic and/or exothermic agents may be used in treatments where exothermic and endothermic reactions (e.g., oncology) are desired, especially in an in situ setting, where the timing and anatomical location of such heat-producing or heat-absorbing reactions can be controlled and manipulated to heat and/or cool tissue, respectively. Multi-encapsulated microspheres allow for control over timing and anatomical location of endothermic and/or exothermic reactions. In other words, the use of the multi-encapsulated oxidized cellulose formulations allows control over the use of heat-produce or heat-removing reactions, as the reactants are compartmentalized. The actual production or removal of heat occurs only upon a breakdown of the encapsulating polymer, thus bringing the reactive components into contact as described in further detail below.

Exothermic agents include a first exothermic reactant and a second exothermic reactant. When the first and second reactants react heat is generated by the reaction into the surrounding tissue. Suitable first and second exothermic reactants include, but are not limited to, acids, salts, water, calcium oxide, and combinations thereof.

Endothermic agents include a first endothermic reactant and a second endothermic reactant. When the first and second reactants react heat is withdrawn by the reaction from the surrounding tissue. Suitable first and second endothermic reactants include, but are not limited to, ethanoic acid, sodium carbonate, calcium carbonate, and combinations thereof.

Endothermic or exothermic reactants may be combined to produce an endothermic reaction, an exothermic reaction, or both, respectively. Suitable medical conditions for treatment with these endothermic and/or exothermic reactions include, for example, cancers (e.g., tumors), inflammation, infections, combinations, thereof, and the like. The use of oxidized cellulose for multiple-encapsulation of hydrophilic endothermic and/or exothermic reactants.

In embodiments, tumors may be treated by application of heat, which destroys cancer cells. There are two modes of heat application for cancer treatment: hyperthermia and thermoablation. Hyperthermia involves heating of certain organs or tissues to temperatures from about 41° C. to about 48° C. Thermoablation generally involves heating tissues to temperatures from about 48° C. to about 56° C. Thermoablation is characterized by acute necrosis, coagulation, and/or carbonization of the tumor tissue due to the relatively higher temperatures involved. Heat is conventionally delivered by electrosurgical energy, resistive heating, microwave energy, heated fluid, combinations thereof, and the like. To compensate for the heat supplied to the tissue (e.g., limit heat application to the tumor) and prevent damage to surrounding healthy tissue, heat sinks (e.g., circulated coolant) may be supplied to the surrounding tissue and/or the device (e.g., catheter) being used during ablation.

In embodiments, the present disclosure provides for in situ delivery of exothermic and/or endothermic reactants/ agents via oxidized cellulose microspheres (e.g., multi-encapsulated formulations) within and outside the tumor, respectively. In embodiments, either one or both of the exothermic and endothermic agents may be delivered while heating and/or cooling is supplied or removed by other suitable methods (e.g., energy ablation, coolant circulation, etc.).

With reference to FIG. 6, a multi-encapsulating microsphere 40 is shown, having one or more first microspheres 42 including a first endothermic or exothermic reactant and one or more second microspheres 44 including a second endothermic or exothermic reactant. After implantation, the microspheres 40, 42, and 44 prevent immediate reaction of the first and second endothermic or exothermic reactants. After degradation of the microsphere 40, the microspheres 42 and 44 subsequently degrade, thereby releasing the first and second endothermic or exothermic reactants, which then react in exothermic or endothermic fashion to heat or cool tissue as described above. In embodiments, the microsphere 40 may also include one or more initiators.

Figure 10:
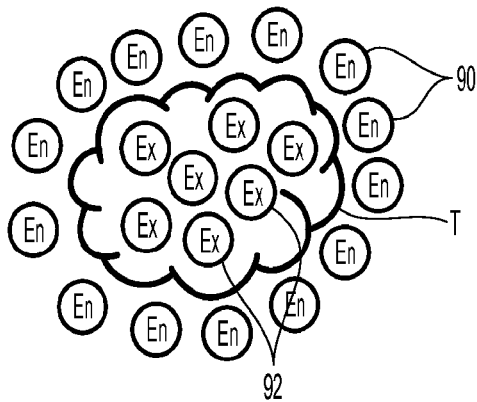
FIG. 10 is a schematic diagram of treatment of a tumor with multi-encapsulated microspheres including endothermic and exothermic reactants in accordance with the present disclosure.

With reference to FIG. 10, the microspheres 40 possessing microspheres 42 and 44 are implanted within and/or around the tissue region (e.g., tumor T). In embodiments, exothermic microspheres 92, for example, microspheres 40 possessing microspheres 42 and 44 including first and second exothermic reactants, respectively, are implanted within the tumor boundary of the tumor T. Endothermic microspheres 90, namely, microspheres 40 possessing microspheres 42 and 44 including first and second endothermic reactants, respectively, are implanted on the periphery of the tumor T with cooling of the surrounding tissue. This allows for enhanced heating within the tumor boundary and active cooling outside the tumor boundary.

In embodiments, in situ exothermic and endothermic reactions may be timed along with initiation of thermal ablation in the tumor, such that the exothermic reaction within the tumor enhances the effect of the thermal ablation, while the endothermic reaction outside the tumor protects the healthy tissue. In further embodiments, heating may be accomplished using conventional hyperthermia or ablation devices, with microspheres 40, 42, and 44 being used to deliver endothermic reactants around the tissue to cool tissue. In further embodiments, cooling may be accomplished using conventional cooling techniques, with microspheres 40 being used to deliver exothermic reactants into the tissue to heat tissue.

Microspheres (e.g., single or multi-encapsulated microspheres) according to the present disclosure may also incorporate one or more magnetic materials allowing for guidance of the encapsulated microspheres containing endothermic and/or exothermic reactants through a patient's body. Multi-encapsulated microspheres may be guided to a treatment site by injecting or otherwise delivering the microspheres into the patient (e.g., intravenously, orally, etc.). After delivery of the microspheres, the treatment site is subjected to one or more magnetic fields, which may be generated by any suitable permanent or temporary magnets (e.g., electromagnets). The magnetic fields retain the microspheres circulating through the patient within the treatment site, i.e., the area to which magnetic field is applied. The microspheres thereafter begin to biodegrade, delivering the materials encapsulated therein to the treatment site. Magnetic guidance allows for the concentration of endothermic or exothermic agents at a predetermined target site, and away from other sites of the patient (e.g., reticular endothelial system).

It should be appreciated that the above-described embodiments of the multi-encapsulated microspheres are merely illustrative and various additional combinations of multi-encapsulated microspheres, bioactive agents, visualization agents, cross-linking precursors, magnetic materials, radioactive materials, and the like may be used in combination and/or interchangeably therewith.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" or "ambient temperature" refers to a temperature from about 20° C. to about 25° C.

EXAMPLES

Comparative Example 1

Incomplete Dissolution of Oxidized Cellulose Having a Degree of Oxidation of 0.6 in a Solution Including 8% by Weight Lithium Chloride (LiCl) and N-Methyl-2-N,N-Dimethylacetamide (DMAc).

About 1.6 grams (g) of LiCl was first dissolved in about 20 milliliters (mL) DMAc to form an 8% LiCl in DMAc solution. About 20 milliliters (mL) of the 8% LiCl in DMAc solution was added to a reactor vessel, and was heated to about 160° C. under argon. About 149 milligrams (mg) of oxidized cellulose having a degree of oxidation of 0.6 was added to the reactor vessel. The mixture was heated for about 1.17 hours, cooled to ambient temperature, and discharged from the reactor vessel. The sample did not fully dissolve, and was observed to discolor significantly, indicating that further oxidation of the oxidized cellulose had occurred.

Comparative Example 2

Incomplete Dissolution of Oxidized Cellulose Having a Degree of Oxidation of 0.6 in 8% by Weight of LiCl in DMAc Solution.

About 20 mL of the 8% LiCl in DMAc solution produced above in Comparative Example 1 and about 90 mg of oxidized cellulose having a degree of oxidation of 0.6 were added to a reactor vessel. The mixture was heated to about 150° C. under argon for about 5.3 hours, cooled to ambient temperature, and discharged from the reactor vessel. The sample did not fully dissolve, and was observed to discolor significantly, indicating further oxidation of the oxidized cellulose occurred.

Comparative Example 3

Pretreatment of Oxidized Cellulose Having a Degree of Oxidation of 0.6 in Water.

About 22 mg of oxidized cellulose having a degree of oxidation of 0.6 was placed in a reactor vessel and about 0.66 grams of deionized water was added thereto. The mixture was stirred for a period of time from about 2 minutes to about 3 minutes. The water was then removed in a vacuum, and about 20 mL of the 8% LiCl in DMAc solution from Comparative Example 1 was added to a reactor vessel. The mixture was heated to about 155° C. for about 4.6 hours. It was then cooled to ambient temperature, and discharged from the reactor vessel. The sample did not fully dissolve. Thus, pretreatment of the oxidized cellulose in water had no discernable effect on dissolution.

Comparative Example 4

Dissolution of Cellulose in a Solution Including 1% by Weight of LiCl in N-Methyl-2-Pyrrolidinone (NMP) Under Inert Atmosphere.

About 20 mL of the NMP and approximately 80 mg of non-modified cellulose were added to a reactor vessel. The mixture was heated to about 150° C. under argon for about 6 hours and then cooled to about 110° C. after which approximately 0.2 g of LiCl was added to the reactor vessel. The reactor vessel was maintained at about 110° C. for an additional hour before being cooled to about 80° C. The reactor vessel was maintained at about 80° C. for about 14.5 hours after which it was observed that the sample had not dissolved and that pieces of non-modified cellulose were observed in the reactor vessel indicating that 1% LiCl NMP solution did not completely dissolve cellulose.

Example 1

Dissolution of Oxidized Cellulose Having a Degree of Oxidation of 0.6 in a Solution Including 1% by Weight of LiCl in N-Methyl-2-Pyrrolidinone (NMP).

A 100 mL three-neck round-bottom flask was used as a reactor vessel and was fitted with a gas inlet, a mechanical stirrer, and a gas outlet, which was then connected to a flow rate monitor. The flask was purged with argon for about 5 minutes at a rate of approximately 0.4 liter per minute (L/min), which was measured as approximately 5 bubbles per second by the flow rate monitor.

About 20 mL of anhydrous NMP was pipetted into the flask, which was then again purged with argon. Argon flow was adjusted to a rate of approximately 0.2 L/min or from about 2 bubbles per second to about 3 bubbles per second, as observed on the flow rate monitor.

A helium line was attached to the flask and the argon flow was stopped. The helium line was inserted into the reactor and submerged below the liquid level, and the helium flow was set at approximately 0.2 L/min to sparge the NMP. After about 45 minutes of sparging, the helium line was removed and the argon flow was reinitiated at a rate of about 0.2 L/min.

About 80 mg of oxidized cellulose having a degree of oxidation of 0.6 was cut into approximately 0.5 cm×0.5 cm square pieces. Argon flow was temporarily increased to about 0.4 L/min and the oxidized cellulose was added to the flask, after which the argon flow was restored to about 0.2 L/min.

The mixture was stirred at about 200 revolutions per minute (rpm). The flask was heated from about 130° C. to about 135° C. using a temperature-controlled heating mantle. The temperature was maintained for about 2 hours under argon as the mixture was stirred. Thereafter, the mixture was cooled to a temperature from about 100° C. to about 110° C.

A scintillation vial was purged with argon in preparation for addition of LiCl. About 0.2 grams of anhydrous LiCl was weighed in the vial. Stirring was temporarily suspended and argon flow was increased to about 0.4 L/min while the LiCl was added to the reactor vessel. After addition of the LiCl, the argon flow was restored to about 0.2 L/min. Stirring was resumed at about 450 rpm for about 5 minutes and then reduced to about 200 rpm.

Temperature was maintained from about 100° C. to about 110° C. The mixture was visually inspected approximately 5 minutes after addition of the LiCl and about every 15 minutes thereafter to determine whether oxidized cellulose was dissolved. The oxidized cellulose was observed to have undergone complete dissolution. Heating was terminated and the solution was cooled to ambient temperature and stirred at about 200 rpm. The solution was then transferred into a scintillation vial under argon and sealed. The solution was stored at ambient conditions.

Example 2

Dissolution of Oxidized Cellulose Having a Degree of Oxidation of 0.6 in a Solution Including 1% by Weight of LiCl in NMP Under Ambient Atmosphere.

The same process was followed as set forth in Example 1 above, except the dissolution was carried out under ambient atmosphere. Oxidized cellulose was observed to have undergone complete dissolution.

Example 3

Dissolution of Oxidized Cellulose Having a Degree of Oxidation of 0.6 in a Solution Including 1% by Weight of LiCl in NMP Under Ambient Atmosphere without Helium Sparging.

The same process was followed as set forth in Example 1 above, except the dissolution was carried out under ambient atmosphere and without helium sparging. Oxidized cellulose was observed to have undergone complete dissolution.

Molecular weight was determined for the dissolved oxidized cellulose of Examples 1-3 as summarized in Table 1 below.

TABLE 1

| Example | Mn (g/mol) |
|---------|------------|
| 1 | $2.7 \times 10^5$ |
| 2 | $1.4 \times 10^5$ |
| 3 | $1.8 \times 10^5$ |

As illustrated in Table 1, dissolved oxidized cellulose of Example 1 had the highest molecular weight, whereas the dissolved oxidized cellulose of Examples 2 and 3 had a much lower molecular weight. Without being bound by any particular theory, it is believed that conducting dissolution under ambient atmosphere degrades the oxidized cellulose, resulting in lower molecular weight.

Example 4

Dissolution of Non-Modified Cellulose in 8% by Weight on LiCl in NMP Solution.

The same process was followed as set forth in Example 1 above, except about 80 mg of non-modified cellulose was dissolved, the mixture of the non-modified cellulose and the solvent was heated from about 145° C. to about 155° C., and about 1.6 grams of anhydrous LiCl was added to the mixture to achieve 8% by weight LiCl in NMP solution since 1% LiCl solution was ineffective as illustrated in Comparative Example 4. Further, after addition of LiCl, the temperature was maintained from about 100° C. to about 110° C. for at least one hour. The non-modified cellulose was observed to have undergone complete dissolution.

Preparation of a Mobile Phase of 1% by Weight of LiCl in NMP Solution for Gel Permeation Chromatography (GPC).

About 1.5 liters (L) of NMP was added to a 2 L volumetric flask, which was then loosely capped with a glass stopper. NMP was stirred. About 20 grams of LiCl was added to the NMP and was stirred for about 60 minutes until it was dissolved. About 0.5 L of NMP was added to the 2 liter mark and stirring was stopped. Additional NMP was added to the mark and the solution was mixed by hand-inverting. A 1 micron polytetrafluoroethylene (PTFE) filter membrane was placed in a filtration apparatus and a vacuum was applied, which enabled the LiCl in NMP solution to flow through the membrane, thereby filtering the solution. The mobile phase solution was stored at ambient conditions.

Analysis of Dissolved Oxidized Cellulose of Example 1, Non-Modified Cellulose of Example 4, and a Standard Sample.

Samples of the dissolved oxidized cellulose of Example 1, the non-modified cellulose of Example 4, and a pullalan standard sample were separately filtered through a 1 micron PTFE filter membrane into 3 separate high-performance liquid chromatography (HPLC) vials. In addition, a combined sample was also prepared by combining about 500 microliters (μL) of the dissolved oxidized cellulose of Example 1 and about 500 μL of the pullalan standard sample (at a concentration of about 2 mg/mL) in a single HPLC vial.

All of the samples were subjected to GPC analysis performed using a gel permeation chromatography system with two 300 millimeter (mm)×7.5 mm columns of Polymer Laboratories' PLGEL™ in a series configuration. A DAWN® HELEOS™ II multi-angle laser light scattering system from (Wyatt Technology of Santa Barbara, Calif.) was used for absolute molecular weight determination. A refractive index model number OPTILAB® rEX in conjunction with the light scattering detector supplied by Wyatt Technology was also used during molecular weight analysis.

Figure 11:
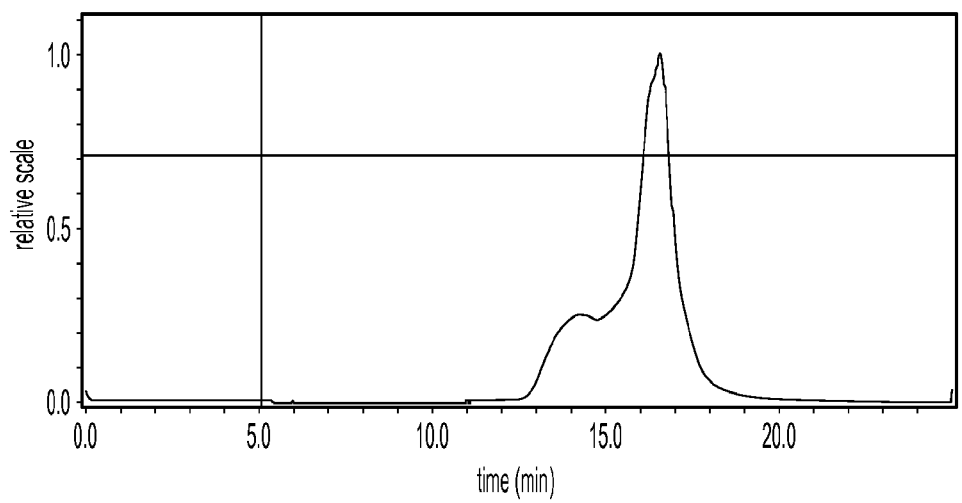
FIG. 11 is a graph of a chromatogram of oxidized cellulose dissolved in accordance with the present disclosure.
Figure 12:
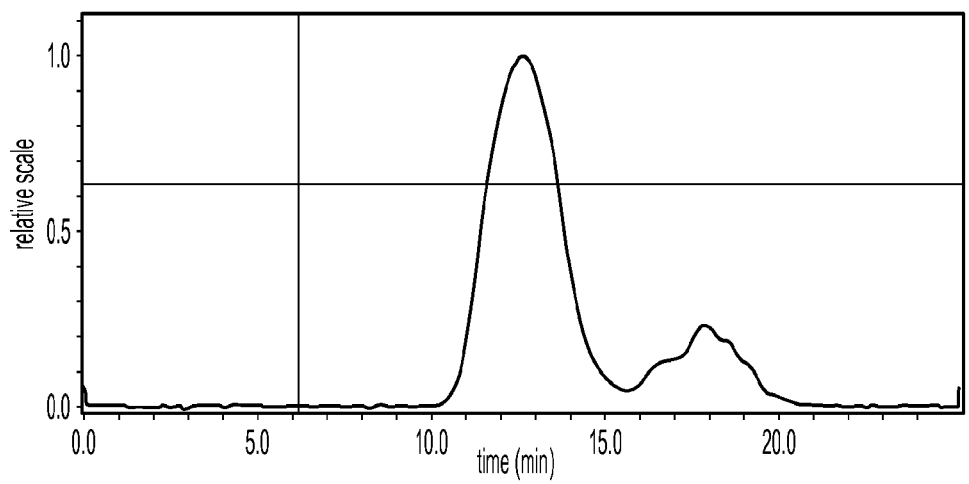
FIG. 12 is a graph of a chromatogram of non-modified cellulose dissolved in accordance with the present disclosure.

GPC was performed at a flow rate of about 1 mL per minute, at a temperature of about 50° C., with an injection volume of about 100 μL. GPC chromatograms of the oxidized cellulose of Example 1 and the non-modified cellulose of Example 4 are shown in FIGS. 11 and 12, respectively.

Example 5

Dissolution of Oxidized Cellulose Having a Degree of Oxidation of 0.39 in 8% by Weight of LiCl in DMAc Solution.

About 20 mL of DMAc was added to a reactor vessel under argon, followed by sparging thereof for approximately 10 minutes with helium. About 19 mg of oxidized cellulose having a degree of oxidation of 0.39 was added to the reactor vessel, which was initially heated to about 144° C. After addition of the oxidized cellulose, the temperature was increased to about 152° C. for approximately 3.2 hours. The reactor vessel was then cooled to about 95° C. and about 1.6 grams of LiCl was added to the mixture to form an 8% LiCl in DMAc solution. The mixture was then heated to about 95° C. for about 45 minutes, then cooled to ambient temperature. The solution was stirred at ambient temperature for approximately 64 hours, and discharged from the reactor vessel. The oxidized cellulose was observed to have undergone complete dissolution.

Example 6

Dissolution of Oxidized Cellulose Having a Degree of Oxidation of 0.39 in a Solution Including 8.8% by Weight of LiCl in NMP.

About 20 mL of NMP was added to the reactor vessel under argon followed by sparging thereof for approximately 1 hour with helium. About 10.2 mg of oxidized cellulose having a degree of oxidation of about 0.39 was added to the reactor vessel, which was initially heated to a temperature from about 148° C. to about 154° C. for approximately 2.5 hours. The reactor vessel was then cooled to about 103° C. and about 1.77 grams of LiCl was added to the mixture to form an 8.8% LiCl in NMP solution. The mixture was then heated to a temperature from about 103° C. to about 105° C. for about 1 hour, then cooled to ambient temperature. The solution was stirred at ambient temperature for approximately 24 hours, and discharged from the reactor vessel. The oxidized cellulose was observed to have undergone complete dissolution.

Example 7

Dissolution of Oxidized Cellulose Having a Degree of Oxidation of 0.39 in a Solution Including 1% by Weight of LiCl in NMP.

About 20 mL of NMP was added to the reactor vessel under argon followed by sparging thereof for approximately 1 hour with helium. About 11 mg of oxidized cellulose having a degree of oxidation of about 0.39 was added to the reactor vessel, which was initially heated to a temperature from about 143° C. to about 148° C. for approximately 2 hours. The reactor vessel was then cooled to about 100° C. and about 0.20 grams of LiCl was added to the mixture to form a 1% LiCl in NMP solution. The mixture was then heated to about 93° C. for about 8 minutes, then cooled to ambient temperature. The solution was stirred at ambient temperature for approximately 24 hours, and discharged from the reactor vessel. The oxidized cellulose was observed to have undergone complete dissolution.

Example 8

Formation of Oxidized Cellulose Microspheres from an Oxidized Cellulose Solution Including 1% by Weight of LiCl in N-Methyl-2-Pyrrolidinone (NMP).

A 600 mL glass beaker was set on a ring stand. A constant-torque mixer was fitted with a medium-shear impeller, which was inserted into the beaker. Approximately 200 mL of heavy white mineral oil was added to the beaker with the mixer set to rotate at approximately 1,500 rpm. About 1.7 grams of oxidized cellulose solution (about 15% by weight/volume of oxidized cellulose in NMP) was added drop-wise to the vortex of the stirring mineral oil for about 15 minutes until all of the solution was added to the oil to form an emulsion including a plurality of oxidized cellulose microspheres.

About 150 mL of isopropyl myristate was added to the emulsion and the mixer speed reduced to approximately 900 rpm and maintained for about 45 minutes. Thereafter, another 150 mL of isopropyl myristate was added to the emulsion such that isopropyl myristate was present at a ratio to the oil of about 3:2 and rotations were reduced to approximately 600 rpm.

Figure 13A:
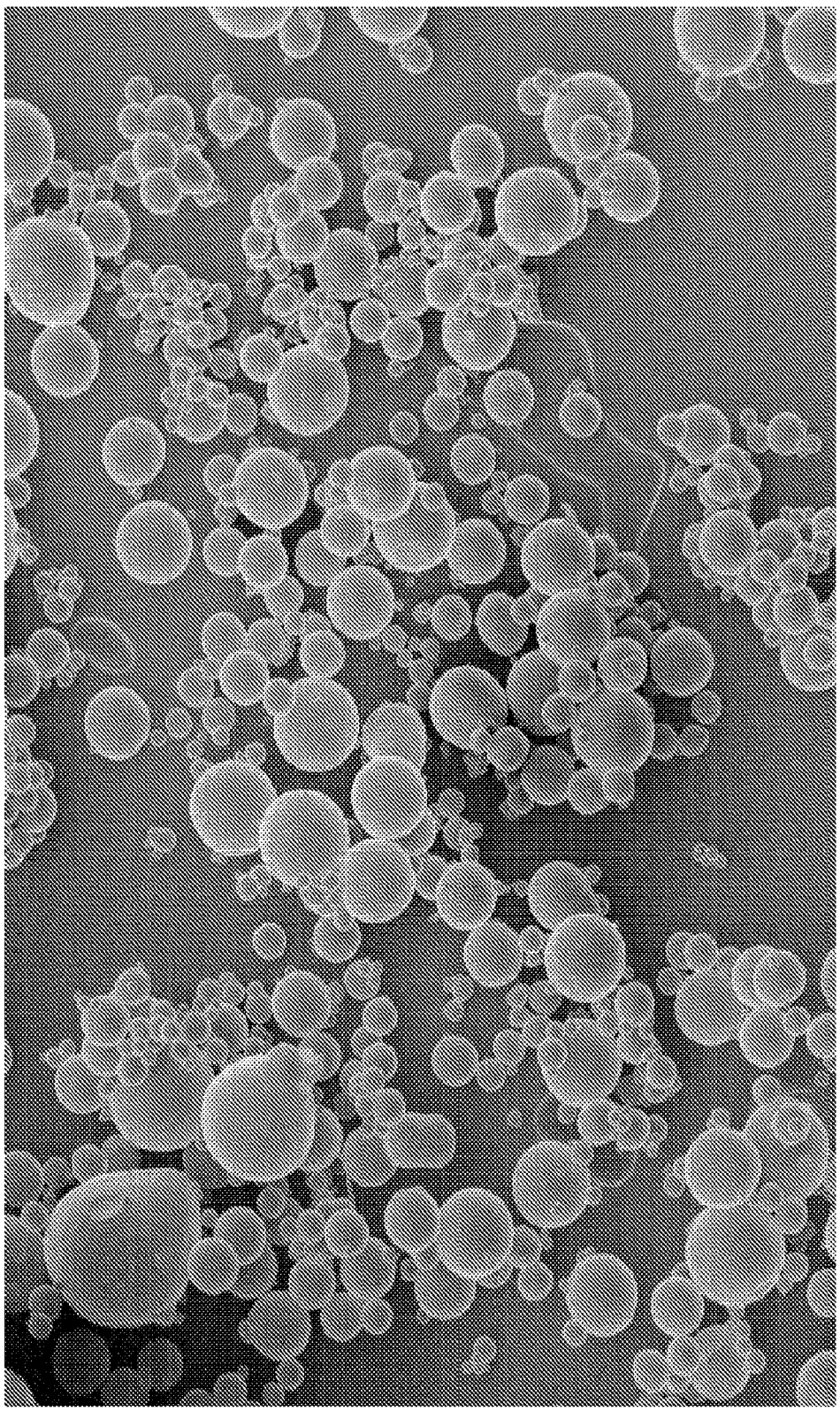
FIGS. 13A-B are scanning electron microscope images of oxidized cellulose microspheres in accordance with the present disclosure.
Figure 13B:
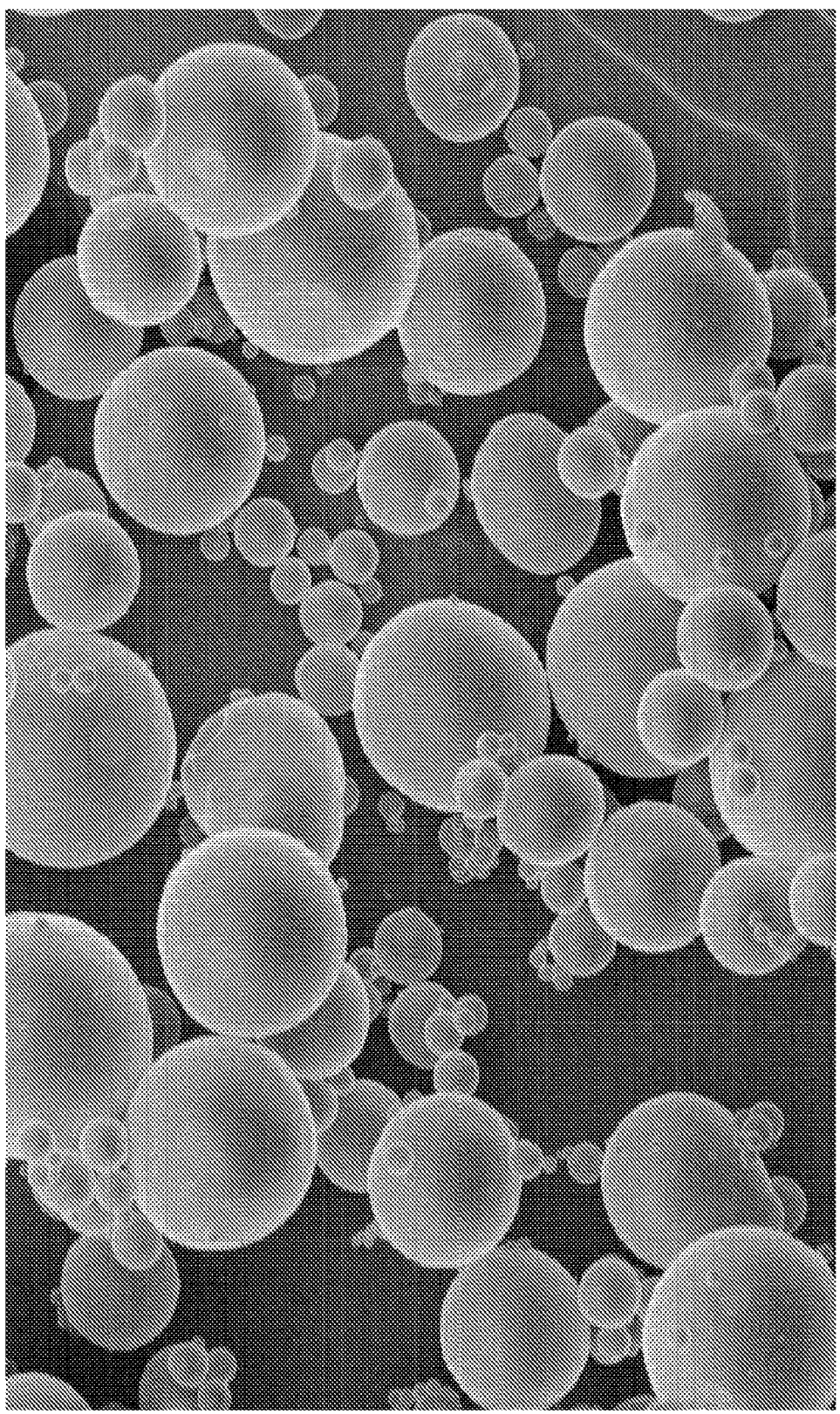

The emulsion was stirred from about 2 hours to about 3 hours to extract the NMP from the oxidized cellulose microspheres. After NMP was extracted, microspheres were collected by filtration. The microspheres were then washed with a sufficient volume of n-heptane to remove any trace of processing oils on the surface of the microspheres. The microspheres were dried for about 24 hours. Collected microspheres were imaged using a Zeiss Leo 435, scanning electron microscope (SEM), which are shown in FIGS. 13A-B at about 100×, and 250×, respectively. The SEM images show microspheres having a spherical shape and a smooth outer surface.

Example 9

Formation of 18% by Weight (Theoretical Loading) Vitamin B-12 Loaded Oxidized Cellulose Microparticles, from a 15% by Weight/Volume Oxidized Cellulose Solution Including 1% by Weight of LiCl in N-Methyl-2-Pyrrolidinone (NMP).

A discontinuous phase was prepared from the oxidized cellulose solution of Example 1. About 3 grams of the oxidized cellulose solution (about 15% by weight/volume of oxidized cellulose in NMP) was combined with approximately 100 milligrams of cyanocobalmin (vitamin B-12).

A 1 liter glass beaker was set on a ring stand. A constant-torque mixer was fitted with a medium-shear impeller, which was inserted into the beaker. Approximately 300 mL of heavy white mineral oil was added to the beaker with the mixer set to rotate at approximately 550 rpm. The solution of cyanocobalmin and oxidized cellulose was then added drop-wise to the vortex of the stirring mineral oil for about 15 minutes until all of the solution was added to the oil to form an emulsion.

About 300 mL of cottonseed oil was added to the emulsion. The emulsion was stirred at approximately 900 rpm for about 60 minutes. Thereafter, another 300 mL of cottonseed oil was added to the emulsion. The emulsion was again stirred at approximately 900 rpm for about 60 minutes. About 100 mL of n-heptane was added to the emulsion.

The emulsion was stirred for about 60 minutes to extract the NMP from the oxidized cellulose microparticles. After NMP was extracted, microparticles were collected by filtration. The microparticles were then washed with a sufficient volume of n-heptane to remove any trace of processing oils on the surface of the microparticles. The microparticles were dried for about 24 hours.

Figure 14A:
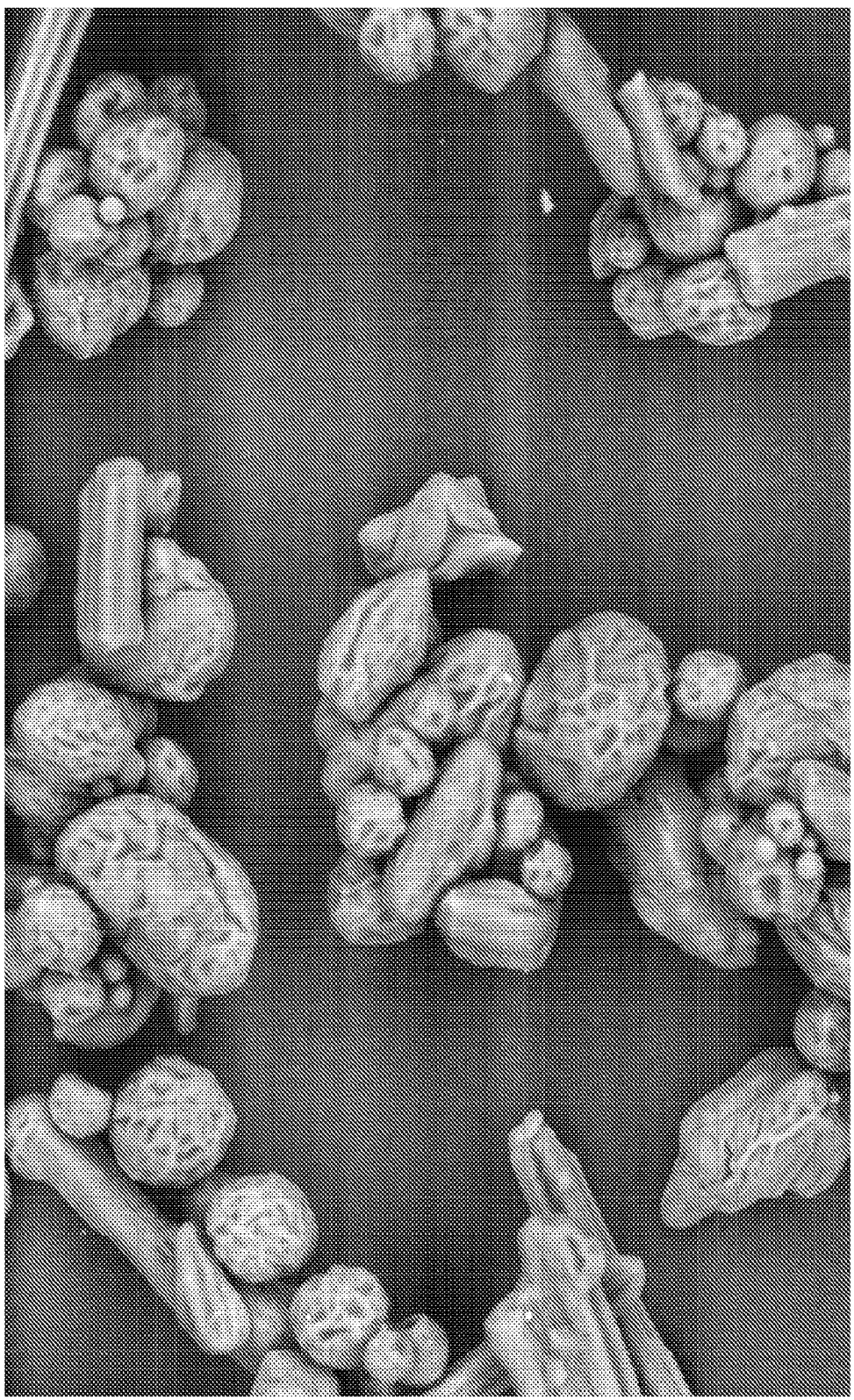
FIGS. 14A-B are scanning electron microscope image of oxidized cellulose microparticles including 18% loaded vitamin B-12 in accordance with the present disclosure.
Figure 14B:
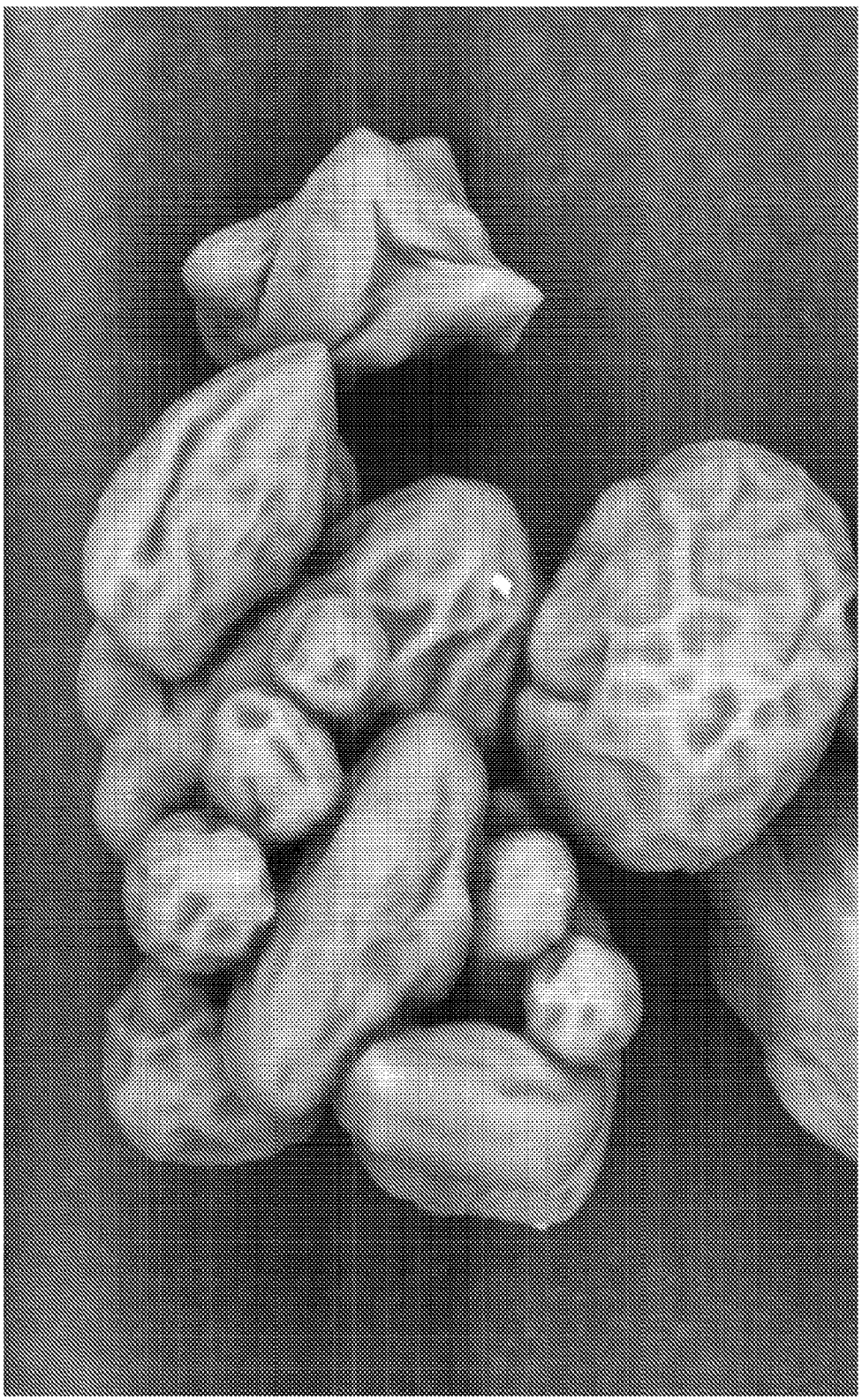

Collected microparticles were imaged using a Zeiss Leo 435 SEM, which are shown in FIGS. 14A-B at about 500×, and 1100×, respectively. The SEM images show microparticles having a textured surface with some microparticles having an elongated, rod-like shape and others having a sphere-like shape. Without being bound by any particular theory, it is believed that smooth, spherecal structure of the microparticles is caused by hydrophilic nature of B-12.

Example 10

Formation of 40% by Weight (Theoretical Loading) Bupivacaine Free Base Loaded Oxidized Cellulose Microparticles, from a 15% by Weight/Volume Oxidized Cellulose Solution Including 1% by Weight of LiCl in N-Methyl-2-Pyrrolidinone (NMP).

The same process was followed as set forth in Example 9 above, except about 253.5 milligrams of bupivacaine free base was added to the oxidized cellulose solution.

Figure 15A:
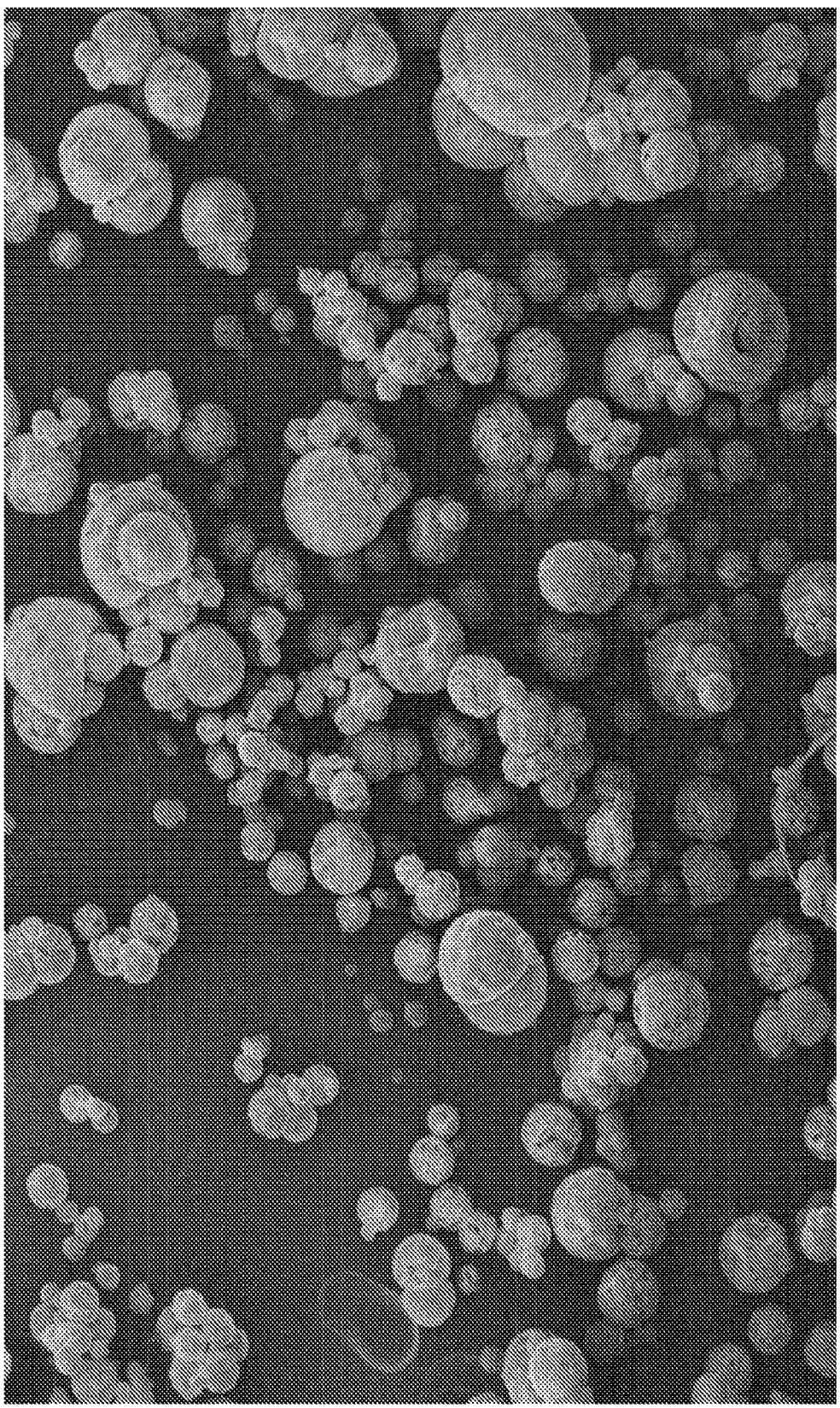
FIGS. 15A-B are scanning electron microscope images of oxidized cellulose microparticles including bupivacaine free base in accordance with the present disclosure.
Figure 15B:
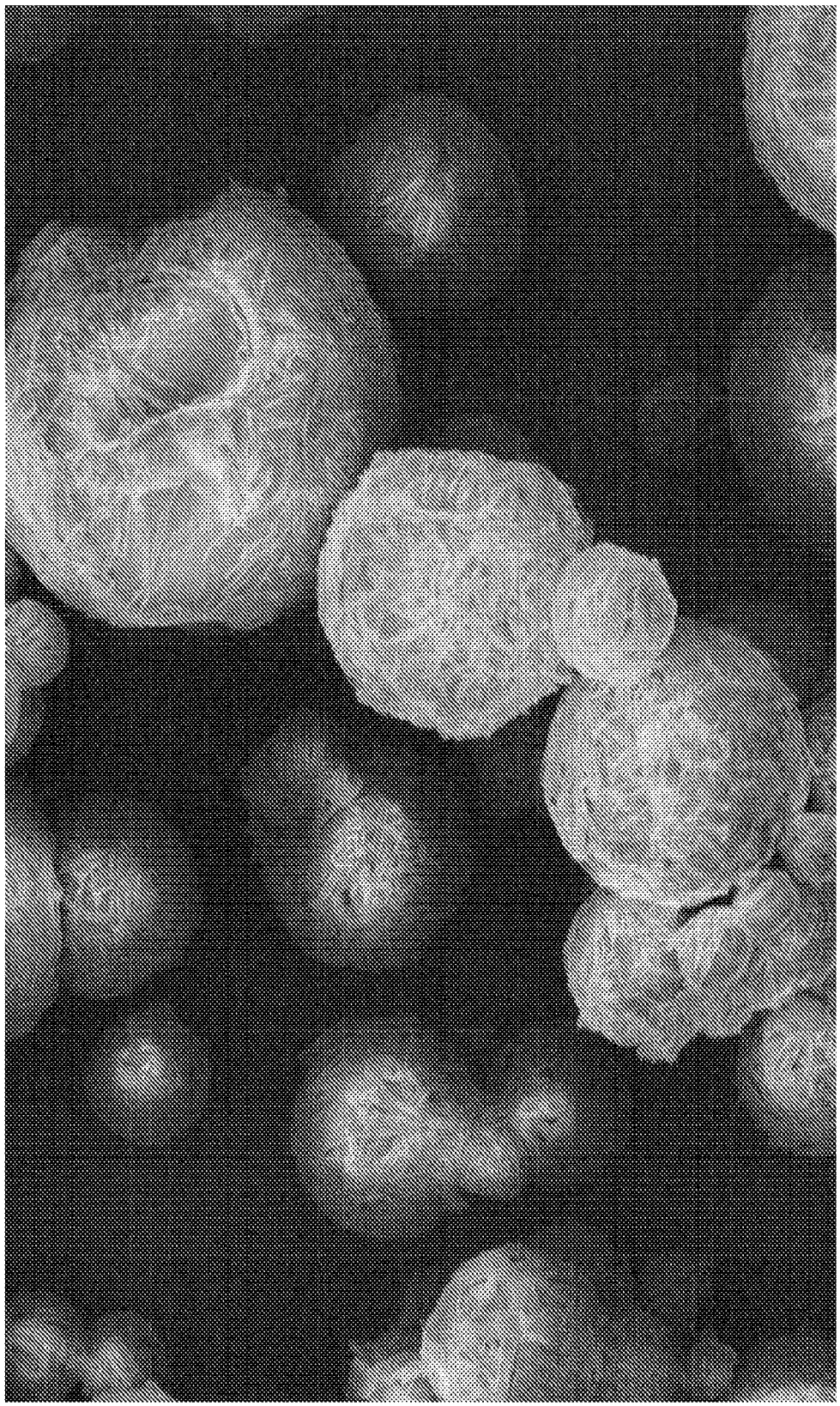

Collected microparticles were imaged using a Zeiss Leo 435 SEM, which are shown in FIGS. 15A-B at about 50× and 250×, respectively. The SEM images show microparticles having a spherical shape and a textured surface.

Without being bound by any particular theory, it is believed that the rougher surface is caused by the wrapping of the crystals of bupivacaine free base, which is hydrophobic, within the oxidized cellulose microparticles.

Example 11

Formation of 40% by Weight (Theoretical Loading) Bupivacaine HCl Loaded Oxidized Cellulose Microparticles, from a 15% by Weight/Volume Oxidized Cellulose Solution Including 1% by Weight of LiCl in N-Methyl-2-Pyrrolidinone (NMP).

The same process was followed as set forth in Example 9 above, except about 250.2 milligrams of bupivacaine HCl was added to the oxidized cellulose solution.

Figure 16A:
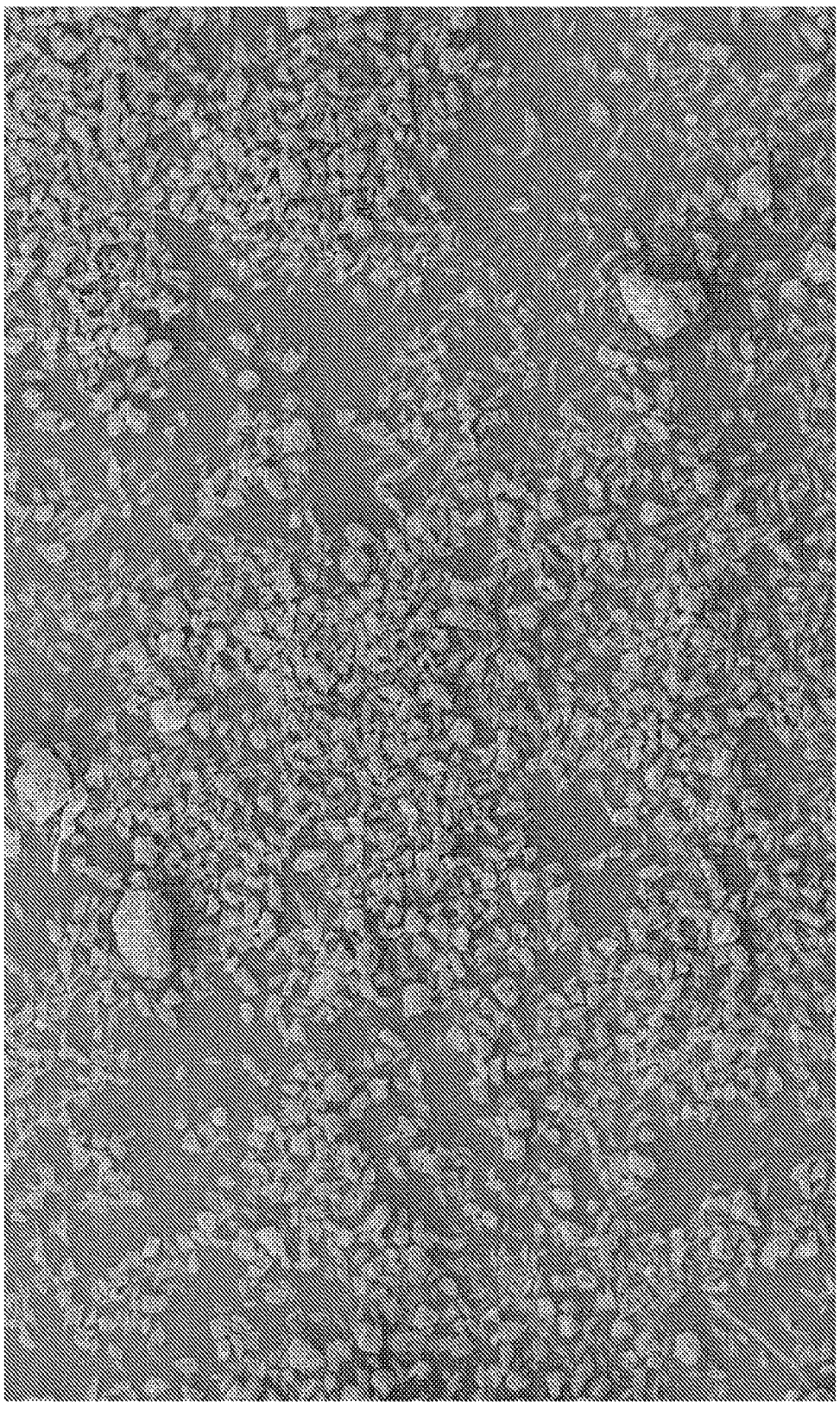
FIGS. 16A-B are scanning electron microscope images of oxidized cellulose microspheres including bupivacaine hydrochloride form in accordance with the present disclosure.
Figure 16B:
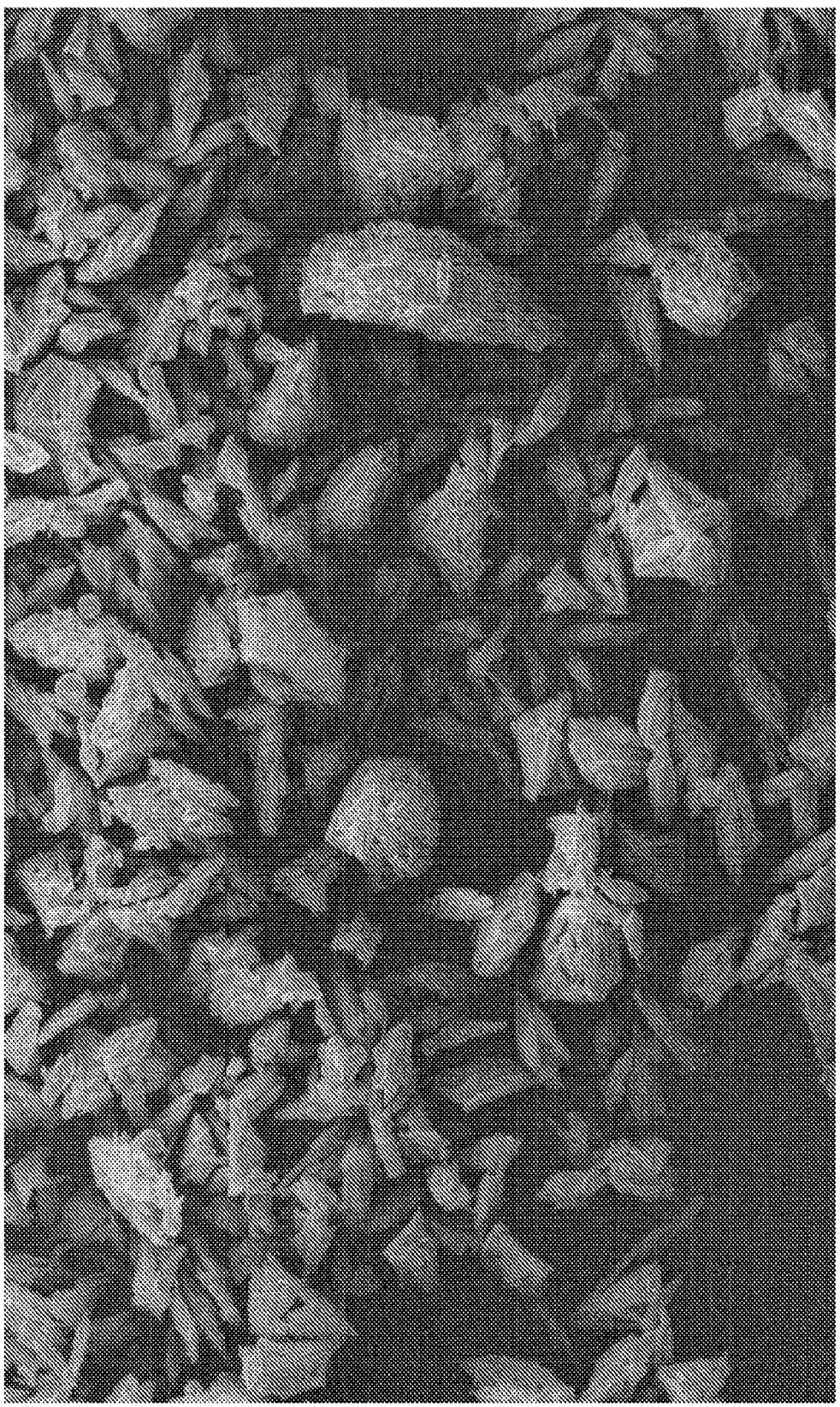

Collected microparticles were imaged using a Zeiss Leo 435 SEM, which are shown in FIGS. 16A-B at about 50× and 250×, respectively. The SEM images show microparticles having an irregular, crystalline shape and a textured surface. Without being bound by any particular theory, it is believed that structure of the microparticles is caused by the needle-like crystalline nature of bupivacaine HCl, which hydrophilic.

Example 12

Formation of 30% (Theoretical and Actual Measurement) by Weight Vitamin B-12 Loaded Oxidized Cellulose Microspheres, from a 15% by Weight/Volume Oxidized Cellulose Solution Including 1% by Weight of LiCl in N-Methyl-2-Pyrrolidinone (NMP).

The same process was followed as set forth in Example 9 above, except about 200 milligrams of cyanocobalmin (vitamin B-12) was added to the oxidized cellulose solution.

Figure 18A:
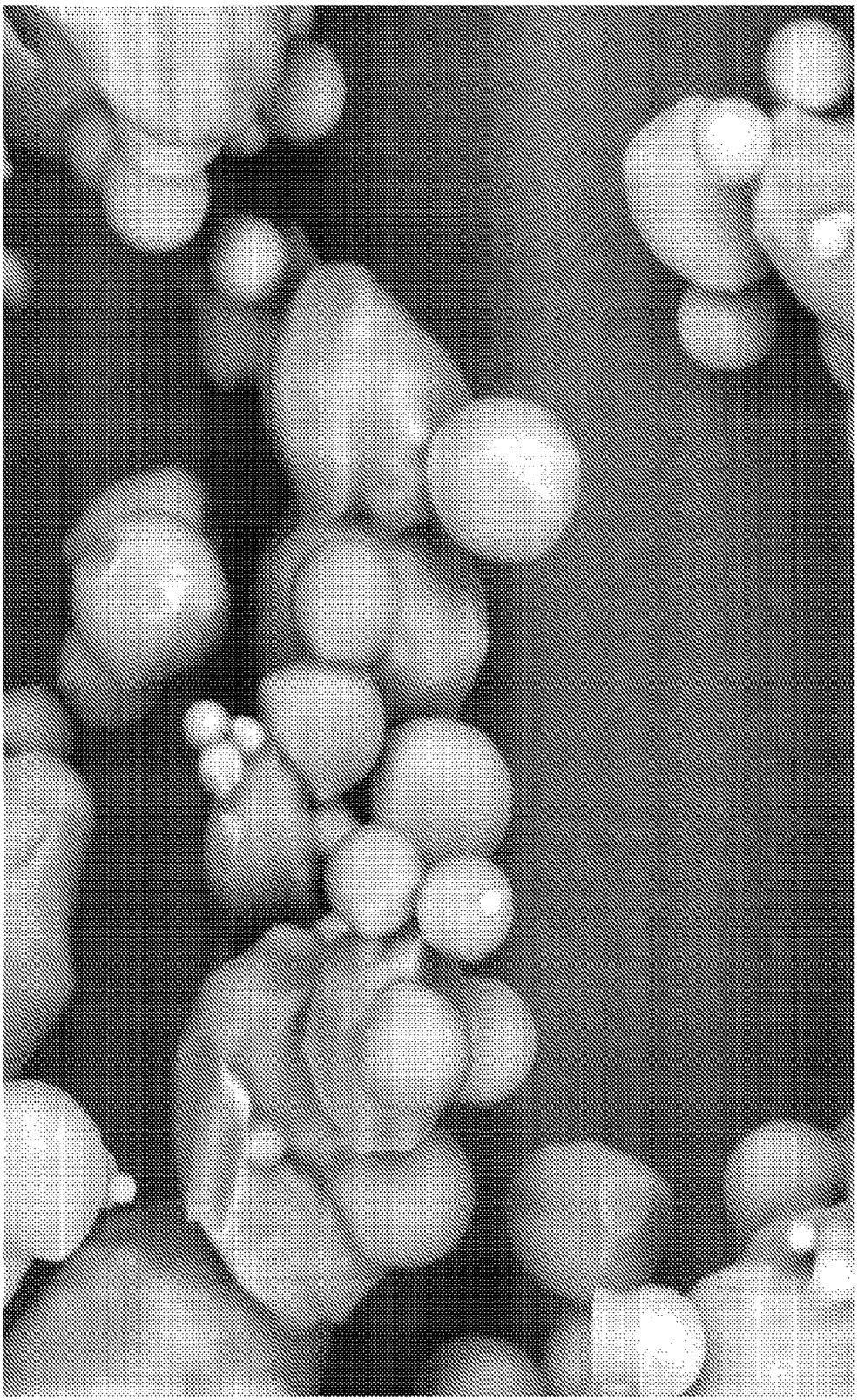
FIGS. 18A-B are scanning electron microscope image of oxidized cellulose microparticles including 30% loaded vitamin B-12 in accordance with the present disclosure.
Figure 18B:
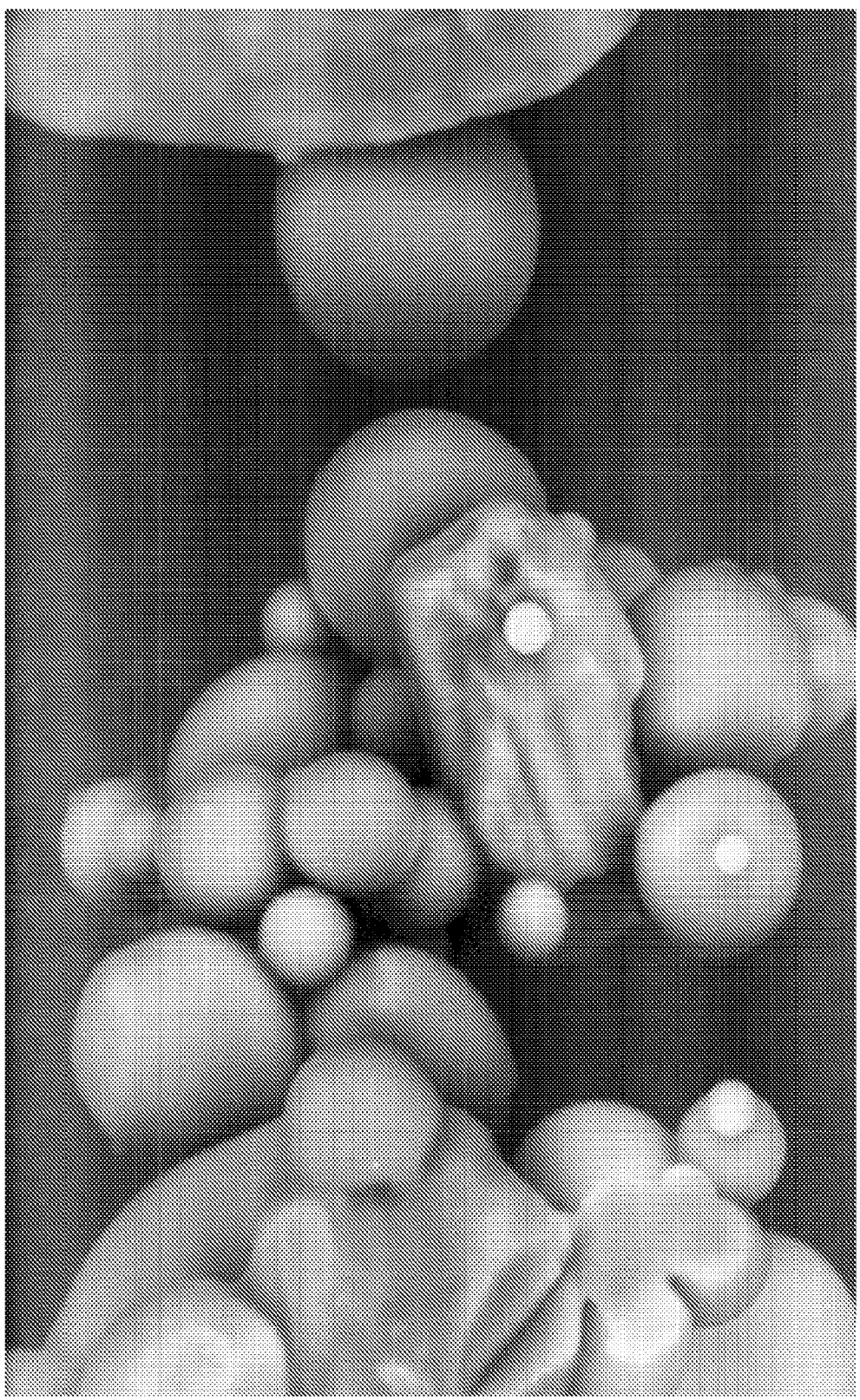

Collected microparticles were imaged using a Zeiss Leo 435 SEM, which are shown in FIGS. 18A-B at about 1,000× and 1,700×, respectively. The SEM images show microspheres having a substantially spherical shape and a smooth outer surface.

Figure 17:
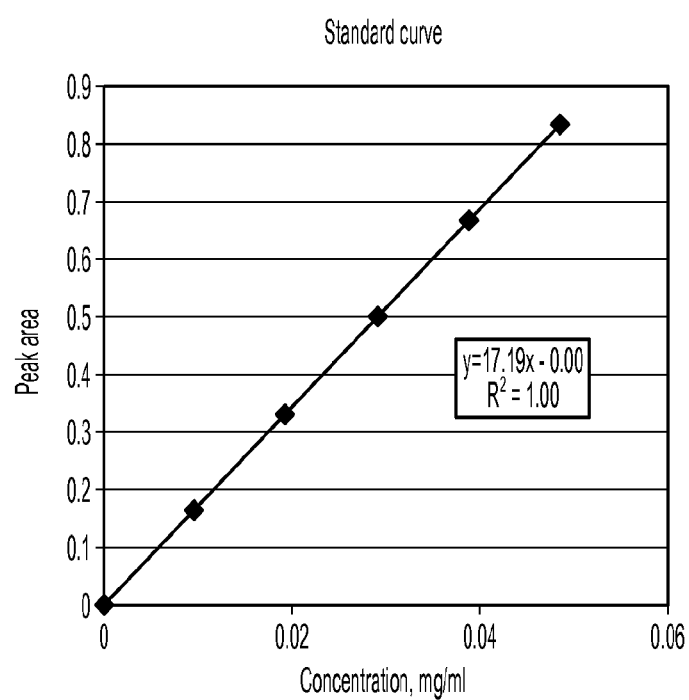
FIG. 17 is an ultraviolet-visible spectroscopy standard calibration curve for vitamin B-12 in accordance with the present disclosure.

Actual loading of the 30% B-12 loaded microspheres was determined using a SpectraMax M2, a UV-Vis spectrophotometer. Approximately 1 mg of B-12 was dissolved in about 10 mL of water and scanned from about 200 nm to about 800 nm in order to determine maximum absorbance. Maximum absorbance was measured at approximately 358 nm. A stock solution was made with about 10 mg B-12 in 200 mL of water. From this stock solution, serial dilutions were made and a five (5) point standard calibration curve was constructed as shown in FIG. 17. About 2.55 mg of the 30% B-12 loaded microspheres was dissolved in 10 mL water, then further diluted to achieve a ratio of microspheres to water of about 1:2. The diluted solution was analyzed and measured at an absorbance concentration of approximately 0.679 as shown in Table 2 below. Actual loading of vitamin B-12 was measured to be about 31%.

TABLE 2

|  | Absorbance | Conc, mg/mL | Total amt., mg | % API | Sample Weights, mg |
|---|---|---|---|---|---|
| Vitamin B12 oxidized cellulose microspheres | 0.679 | 0.04 | 0.79 | 31.0 | 2.55 |

Example 13

Formation of 25% by Weight (Theoretical Loading) Vitamin B-12 Loaded Oxidized Cellulose Microspheres from a 15% by Weight/Volume Oxidized Cellulose Solution Including 1% by Weight of LiCl in N-Methyl-2-Pyrrolidinone (NMP).

The same process was followed as set forth in Example 9 above, except about 150 milligrams of vitamin B-12 was added to the oxidized cellulose solution.

Figure 19A:
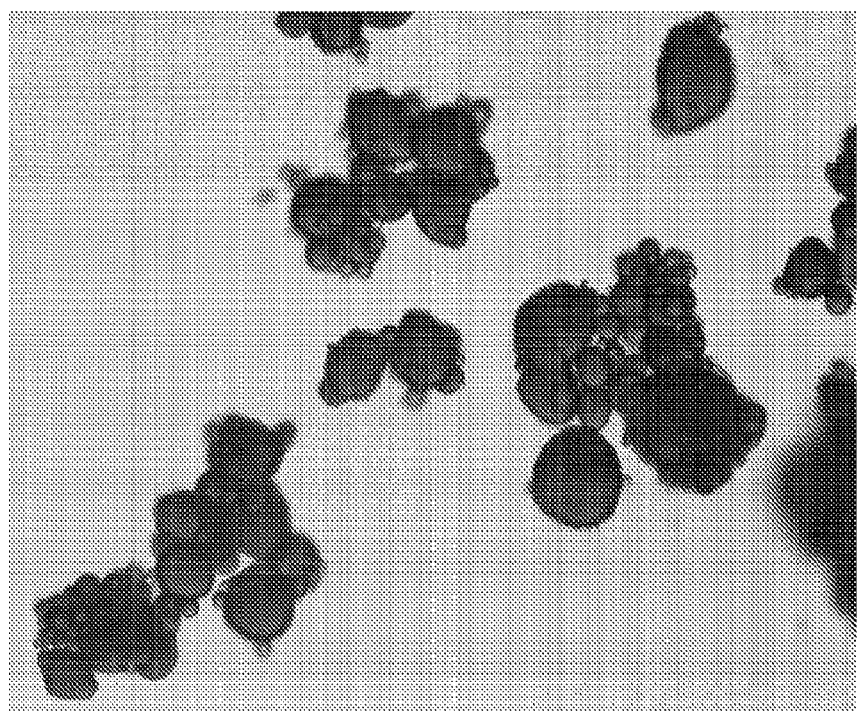
FIGS. 19A-B are scanning electron microscope image of oxidized cellulose microparticles including 25% loaded vitamin B-12 in accordance with the present disclosure.
Figure 19B:
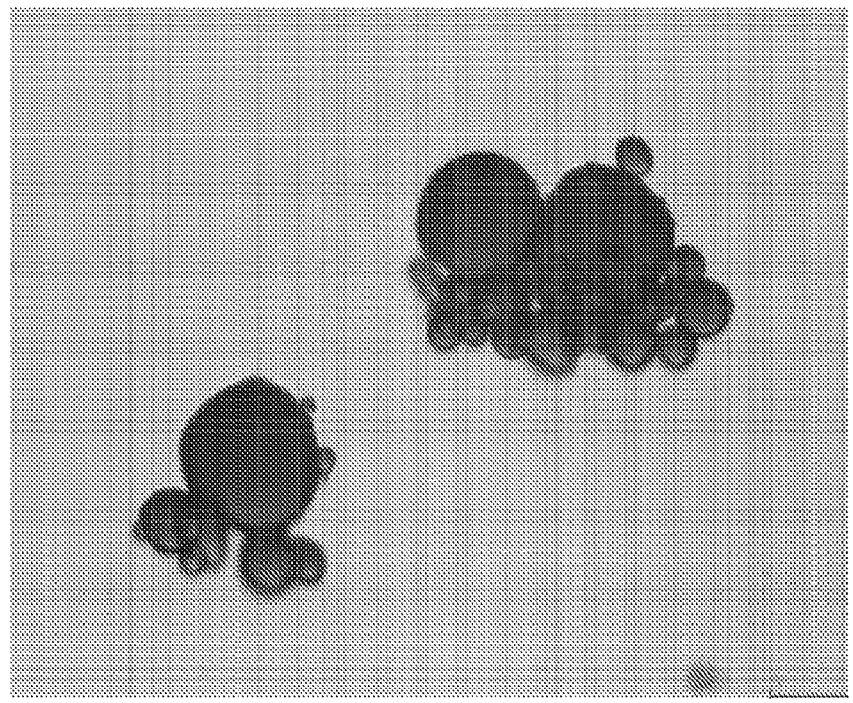

Collected microparticles were imaged using Keyence VHX-600, a light microscope, which are shown in FIGS. 19A-B at about 600× and 1,000×, respectively. The images show microspheres having a substantially spherical shape.

Example 14

Formation of Poly-D,L,-Lactide (PDLLA) Microspheres Encapsulating Cis-Diamminedichloroplatinum(II) (CDDP) Loaded Oxidized Cellulose Microspheres.

A 1 liter glass beaker was set on a ring stand. A constant-torque mixer was fitted with a medium-shear impeller, which was inserted into the beaker. Approximately 200 mL of heavy white mineral oil was added to the beaker with the mixer set to rotate at approximately 1,800 rpm.

About 300 milligrams of CDDP was added to about 3 grams of the oxidized cellulose solution having a concentration of about 15 mg/mL, which formed a gel. The gel was vortexed for about 30 seconds until a uniform consistency was achieved and no particles of CDDP were visible.

The gel of CDDP and oxidized cellulose was then added drop-wise to the vortex of the stirring cottonseed and mineral oils for about 15 minutes at about 1,800 rpm, until all of the solution was added to the oil to form an emulsion.

About 200 mL of cottonseed oil were added to the emulsion and the mixing speed was reduced to about 700 rpm after approximately 1 minute. After about 30 minutes, approximately 200 mL of cottonseed oil was added along with about 50 mL of n-heptane and the emulsion was mixed for approximately 2.5 hours to extract the NMP from the oxidized cellulose microspheres. After the NMP was extracted, microspheres were collected under vacuum by filtration through Whatman No. 4 filter paper. The microspheres were then washed with a sufficient volume of n-heptane to remove any trace of processing oils on the surface of the microspheres.

Figure 20:
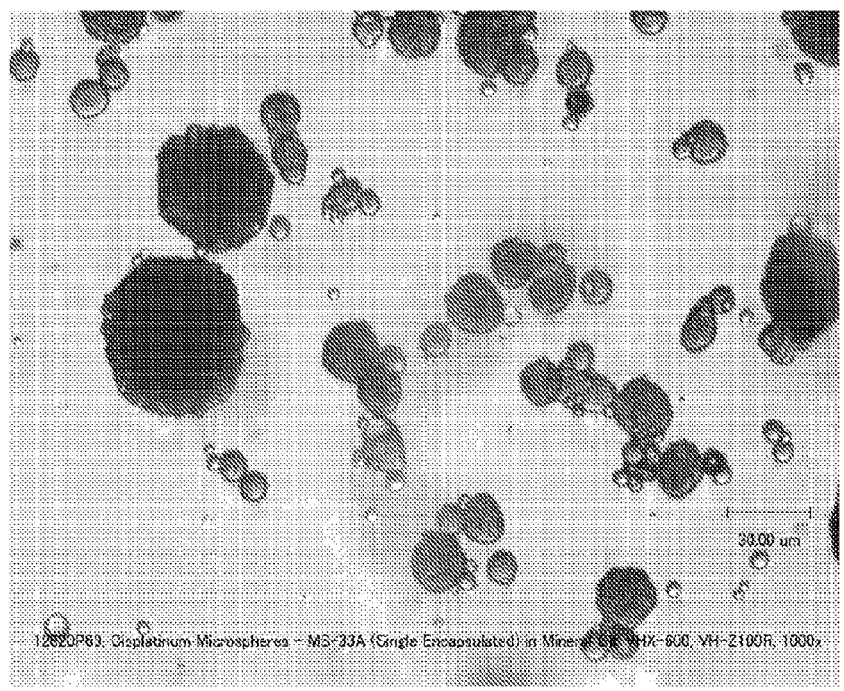
FIG. 20 is a light microscope image of cis-diamminedichloroplatinum(II) loaded oxidized cellulose microspheres in accordance with the present disclosure.

Collected microspheres were imaged using Keyence VHX-600, a light microscope, which are shown in FIG. 20 at about 1,000×. The light images show microspheres having a substantially spherical shape and a smooth surface. The microspheres were of yellow color showing CDDP encapsulation.

A 4 liter glass beaker was set on a ring stand and the mixer was fitted with a high-shear radial impeller above a medium-shear bottom impeller. About 2,500 mL of 1% polyvinyl alcohol (PVA) in water was added to the beaker and the mixing speed was set to about 1,800 rpm. A solution having a concentration of about 200 mg/mL of PDLLA was prepared by dissolving about 1 gram of PDLLA in about 5 mL of dichloromethane. The CDDP/oxidized cellulose microspheres were then added to the PDLLA solution and vortexed to ensure a uniform distribution of the microspheres in the PDLLA solution thereby forming a suspension.

The suspension was then added to the PVA solution. Mixing was maintained at about 1,810 rpm for about 5 minutes after which, the speed was reduced to about 1,150 rpm for about 60 minutes. About 500 mL of distilled water was then added to the emulsion to extract dichloromethane from the multi-encapsulated microspheres, namely, PDLLA microspheres encapsulating the CDDP/oxidized cellulose microsphere. The multi-encapsulated microspheres were harvested after about 2.5 hours of mixing. The microspheres were washed with distilled water to remove all traces of the PVA. They were then collected off each sieve by filtration. The collected microspheres were then air-dried for about 24 hours.

Figure 21:
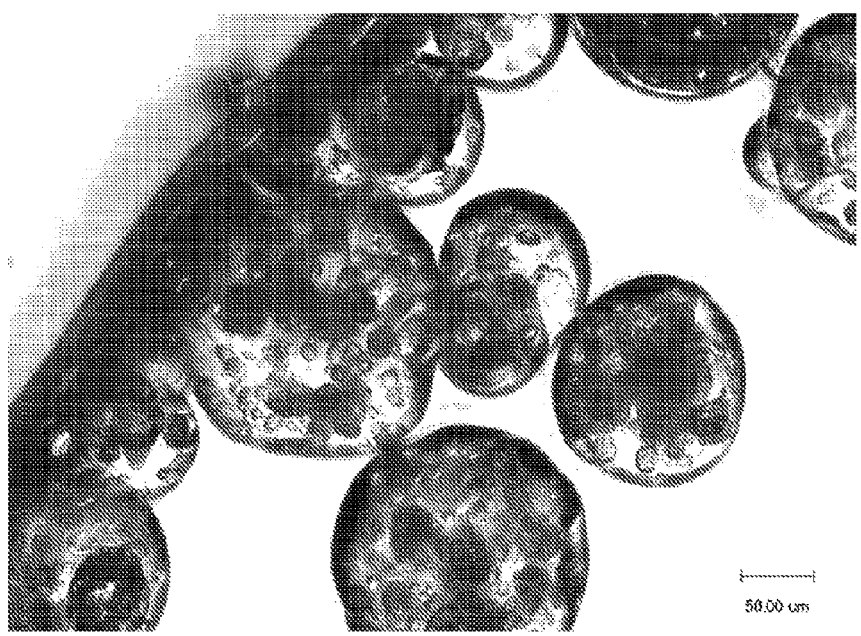
FIG. 21 is a light microscope image of poly-D,L,-lactide microspheres encapsulating cis-diamminedichloroplatinum (II) loaded oxidized cellulose microspheres of FIG. 19 in accordance with the present disclosure.
Figure 22:
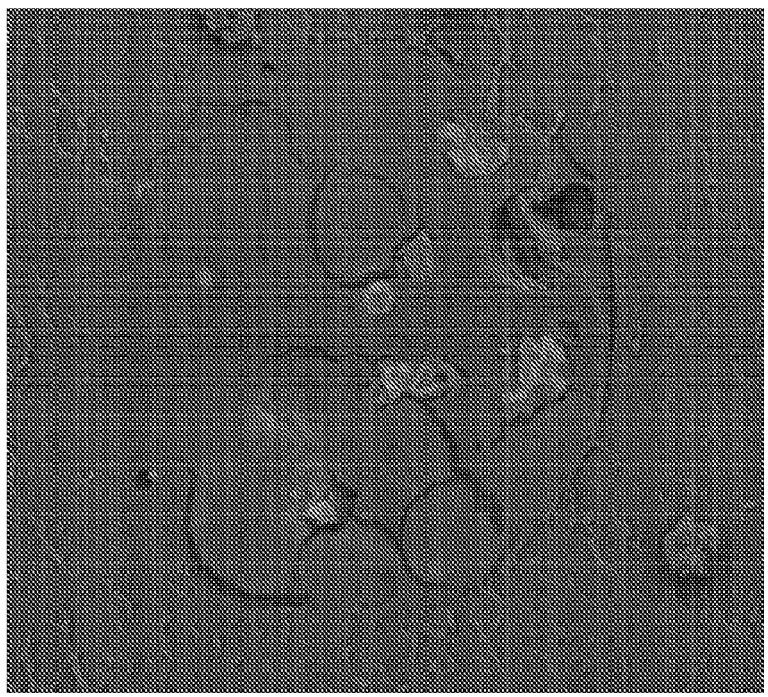
FIG. 22 is a scanning electron microscope image of a cross-section of the microsphere of FIG. 19 in accordance with the present disclosure.

Collected microspheres were imaged using Keyence VHX-600, a light microscope, which are shown in FIG. 21 at about 1,000×. Microspheres were also embedded in epoxy and a cross-sectional slice of thereof was obtained, which was then imaged using a FEI Quanta 600 FEG SEM, which is shown in FIG. 22 at about 1,475×. The images of FIGS. 21 and 22 show larger PDLLA microspheres encapsulating a plurality of oxidized cellulose microspheres, which were observed to be gold (FIG. 21), which in turn, encapsulate CDDP, which was observed to be red (FIG. 22).

CDDP, a water-soluble compound, was successfully encapsulated in microspheres formed from solubilized oxidized cellulose using an oil-in-oil (o/o), solvent extraction method. These microspheres were then encapsulated in polylactide microspheres, using a solid-in-oil-in-water modified emulsion, solvent extraction (MESE) method. The "microsphere(s)-in-a-microsphere" particles were free-flowing and easily handled, no fragility was observed. Since CDDP encapsulation was conducted without water, sodium chloride was not required, which is used when aqueous systems are employed in encapsulating CDDP to prevent transforming the cis form of CDDP into trans, which is has diminishing bioactive effect.

Example 15

Formation of 8.2% by Weight Ferrous Gluconate Loaded Oxidized Cellulose Microspheres from a 15% by Weight/Volume Oxidized Cellulose Solution Including 1% by Weight of LiCl in N-Methyl-2-Pyrrolidinone (NMP).

The same process was followed as set forth in Example 9 above, except about 100 milligrams of ferrous gluconate was added to the oxidized cellulose solution.

Figure 23:
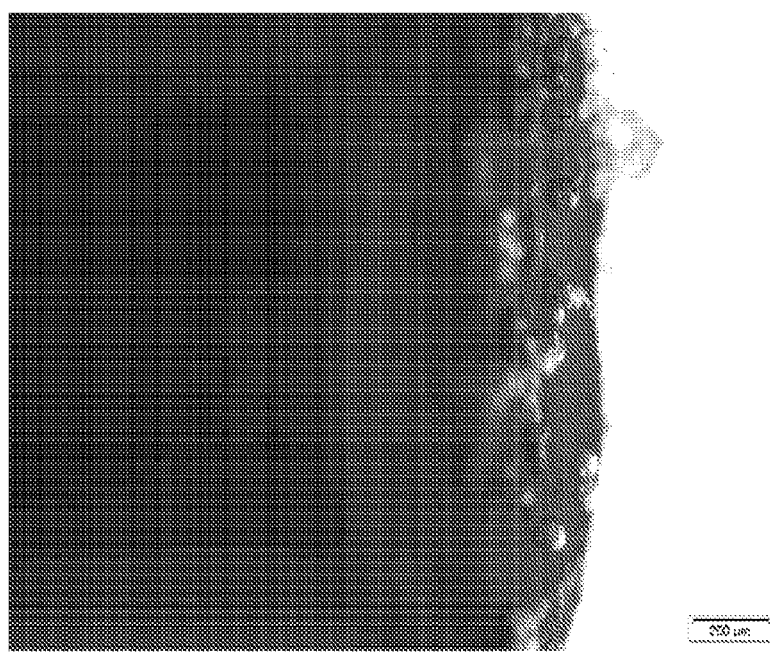
FIG. 23 is a scanning electron microscope image of a cross-section of the microsphere including a magnetic material in accordance with the present disclosure.

Collected microparticles were collected on a glass slide and imaged using an Olympus SZX16, a light microscope, which are shown in FIG. 23 at about 40×. The images show microspheres having a substantially spherical shape and measuring about 100 μm in diameter.

Example 15

Formation of 30% by Weight (Theoretical Loading) Vitamin B-12 Loaded Oxidized Cellulose Microspheres from a 17% by Weight/Volume Oxidized Cellulose Solution Including 1% by Weight of LiCl in NMP.

Approximately 4,000 mg of 17% by weight/volume oxidized cellulose solution was added into a glass scintillation vial to which approximately 300 mg of vitamin B-12 and about 1,000 mg of NMP were added and vortexed for about 30 seconds. The vitamin B-12 and oxidized cellulose solution was then added drop-wise to a 1 liter glass beaker containing about 200 mL heavy mineral oil and about 400 mL of cottonseed oil and mixed for about 2.5 hours. Subsequently, about 200 mL of cottonseed oil and about 50 mL of n-heptane were added and were mixed for about an additional 15 minutes. The contents were poured through a set of approximately 12-inch diameter stainless steel sieves, stacked in descending order, 250 μm, 150 μm, 105 μm, 75 μm, and 25 μm. Microspheres were harvested in each size range and were then washed with n-heptane to remove any residual oil from their surface.

The oxidized cellulose microspheres containing vitamin B-12 were collected on Whatman #4 filter paper under vacuum and air dried overnight before being bottled under an argon overlay.

Example 16

Formation of Cis-Diamminedichloroplatinum(II) (CDDP) Loaded Oxidized Cellulose Microspheres from a 17% by Weight/Volume Oxidized Cellulose Solution Including 1% by Weight of LiCl in NMP.

Approximately 4,000 mg of 17% by weight/volume oxidized cellulose solution was added into a glass scintillation vial to which approximately 330 milligrams of CDDP was added. The vial was then capped and vortexed for about 30 seconds to ensure a uniform suspension. The uniform suspension, was continuously shaken by hand since the oxidized cellulose solution is thixotropic and was then added drop-wise to a 1 liter glass beaker containing about 200 mL heavy mineral oil and about 400 mL of cottonseed oil and mixed for about 2.5 hours. Subsequently, about 200 mL of cottonseed oil and about 50 mL of n-heptane were added and were mixed for about an additional 15 minutes. The contents were poured through a set of approximately 12-inch diameter stainless steel sieves, stacked in descending order, 250 μm, 150 μm, 105 μm, 75 μm, and 25 μm. Microspheres were harvested in each size range and were then washed with n-heptane to remove any residual oil from their surface.

The oxidized cellulose microspheres containing CDDP were collected on Whatman #4 filter paper under vacuum and air dried overnight before being bottled under an argon overlay.

Example 17

Formation of Poly-L,-Lactide (PDLLA) Microspheres Encapsulating Cis-Diamminedichloroplatinum(II) (CDDP) Loaded Oxidized Cellulose Microspheres and Vitamin B-12 Loaded Oxidized Cellulose Microspheres.

About 800 mg of 100% PLLA was added to about 5 mL of dichloromethane in a glass scintillation vial, which was shaken to dissolve PLLA. Upon complete dissolution of the PLLA, about 600 mg of CDDP loaded microspheres sized from about 25 μm to about 75 μm and about 600 mg of vitamin-B12 loaded oxidized cellulose microspheres sized from about 25 μm to about 75 μm were added to the PLLA solution and the vial was securely capped and vortexed for about 20 seconds to ensure a uniform suspension.

The uniform suspension was poured, using a long neck glass funnel, into a 1% aqueous solution by weight/volume of polyvinyl alcohol (PVA) and mixed. The microspheres encapsulating CDDP loaded microspheres and vitamin-B12 loaded oxidized cellulose microspheres were formed and collected on stainless steel sieves set in descending size and washed with de-ionized water to remove any trace of PVA. Each size fraction was then collected on Whatman #4 filter paper under vacuum and allowed to air dry overnight. Each size fraction was transferred to a tared and labeled scintillation vial and weighed. An argon overlay was added to the vial and was then capped, parafilmed and stored at about 4° C. until needed.

Figure 24:
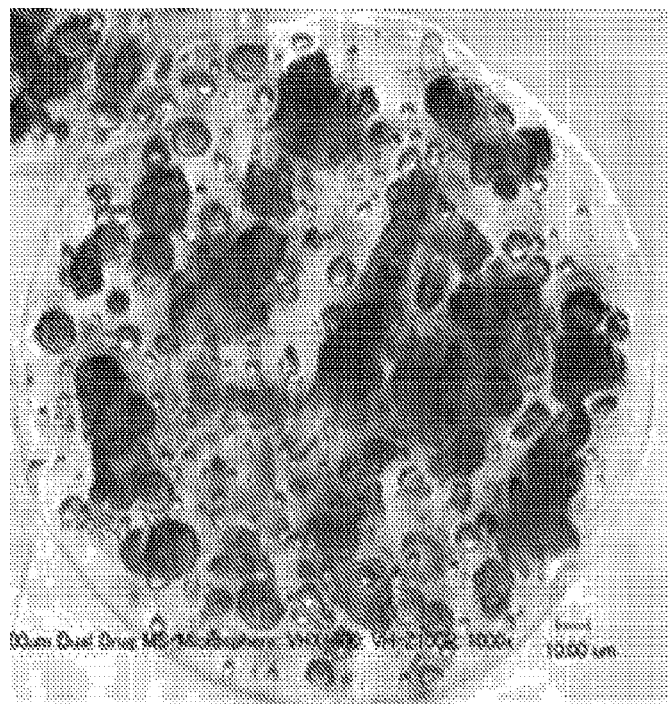
FIG. 24 is a light microscope image of poly-L,-lactide microspheres encapsulating cis-diamminedichloroplatinum (II) loaded oxidized cellulose microspheres and vitamin B-12 loaded oxidized cellulose microspheres in accordance with the present disclosure.

Collected microspheres were imaged using an Olympus SZX16, a light microscope, which are shown in FIG. 24 at about 1,000×. The image of FIG. 24 shows a larger PLLA microsphere encapsulating CDDP loaded oxidized cellulose microspheres, which were observed to be gold, and vitamin-B12 loaded oxidized cellulose microspheres, which were observed to be red.

Figure 25:
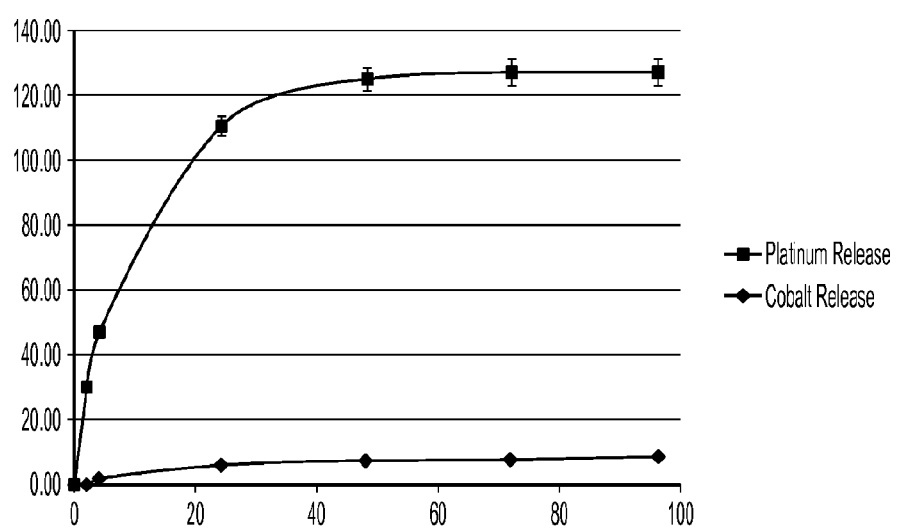
FIG. 25 is a plot of a release profile of cis-diamminedichloroplatinum(II) of the microspheres of FIG. 24 in accordance with the present disclosure.
Figure 26:
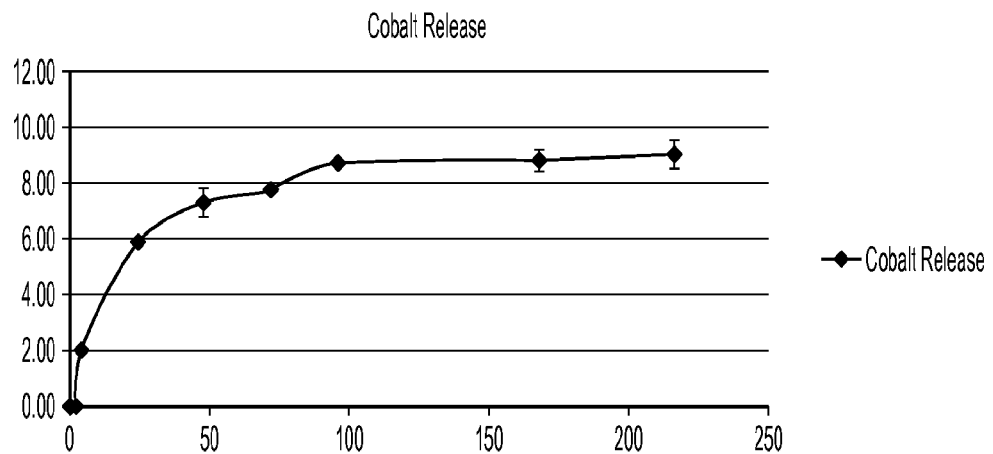
FIG. 26 is a plot of a release profile of vitamin B-12 of the microspheres of FIG. 24 in accordance with the present disclosure.

Release rates of the CDDP and vitamin B-12 encapsulated in the microspheres of microspheres of Example 17 were also measured and are shown in plots of FIGS. 25 and 26. FIG. 25 shows plots of a release rate of platinum, which is indicative of the release of CDDP and a release rate of cobalt, which is indicative of the release of vitamin B-12 over about 100 hours. FIG. 26 shows a plot of a release rate of cobalt, which is indicative of the release of vitamin B-12 over 250 hours.

Example 18

Analysis of Degree of Oxidation of Oxidized Cellulose of Example 1.

Degree of oxidation of dissolved oxidized cellulose was analyzed using conductimetric and pH metric titration and compared with undissolved oxidized cellulose.

Multiple samples from about 90 mg-700 mg of dissolved and undissolved oxidized cellulose were prepared. Each of the samples was dissolved in about 15 mL of a sodium hydroxide (NaOH) solution having molarity (M) from about 0.05 M to about 0.5 M. The solutions were titrated with a hydrogen chloride (HCl) solution from about 0.05 M to about 0.5 M on a TIM 845 titration apparatus, from Radiometer Analytical SAS, Villeurganne Cedex, France and conductimetric and pH-metric curves were obtained. A blank titration was done in the same conditions to determine the NaOH concentration.

Figure 27:
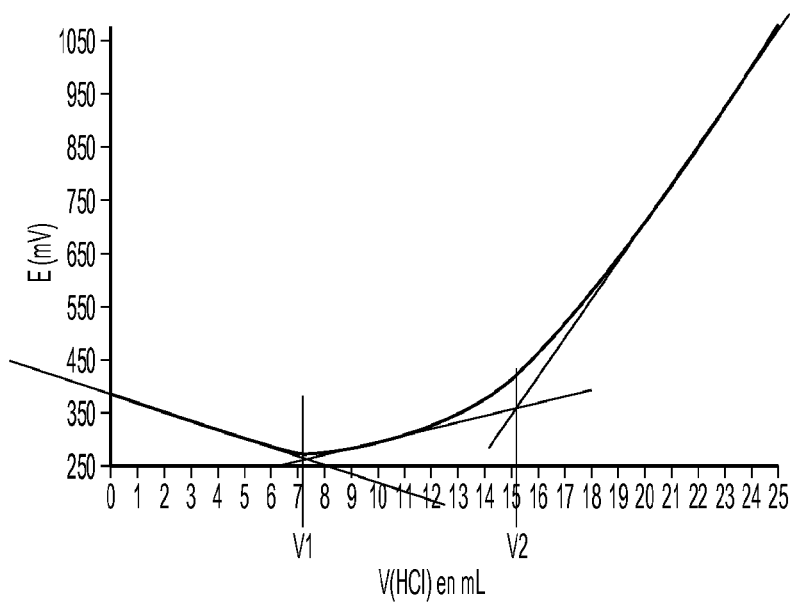
FIG. 27 is a plot of a conductometric titration curve of oxidized cellulose in accordance with the present disclosure.
Figure 28:
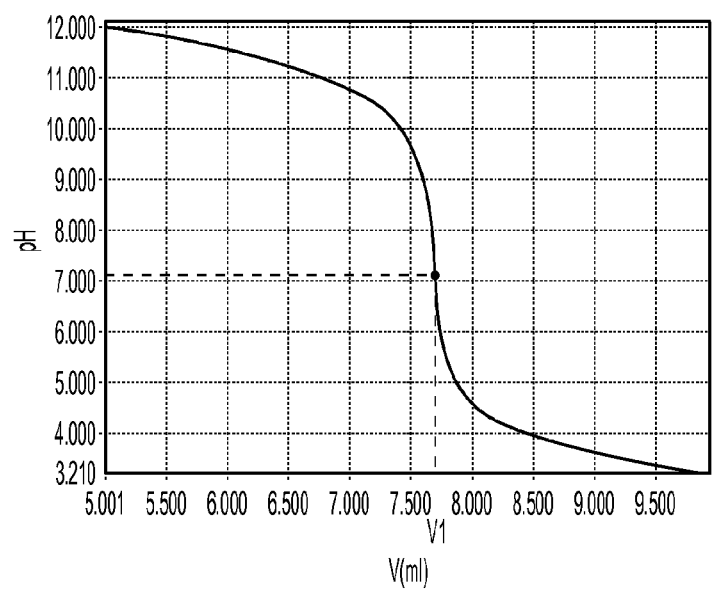
FIG. 28 is a plot of a pH-metric titration curve of oxidized cellulose in accordance with the present disclosure.

The conductometric titration curves showed the presence of strong alkali, corresponding to the excess of NaOH and a weak alkali corresponding to the carboxyl content, as shown in an illustrative conductometric curve of FIG. 27. The characteristic pH-metric curve is shown in the FIG. 28, in which the equivalence point corresponds to the residual NaOH in the samples.

The degree of oxidation for each sample was calculated using the following formulas (I) and (II):

$$DO = \frac{162 \times n(COOH)}{w - (14 \times n(COOH))} \quad (I)$$

$$n(COOH) = (V2 - V1) \times C(HCl) \quad (II)$$

In which V2 is the volume of HCl in liters obtained by the blank titration or from the conductometric curve as indicated in FIG. 27; V1 is the amount HCl in liters as shown in FIG. 27, or the equivalence point from the pH-metric titration of FIG. 28; C is HCl concentration in moles per liter (Mol/L) an w is the weight of oven-dried sample of undissolved oxidized cellulose in grams.

The degree of oxidation of non-dissolved oxidized cellulose and for dissolved oxidized cellulose of Example 1 samples are summarized in Table 3 below:

TABLE 3

| Undissolved Oxidized Cellulose | Dissolved Oxidized Cellulose |
|---|---|
| 0.6 | 0.53 |
| 0.56 | 0.52 |
| 0.57 | 0.52 |
| 0.6 | |

TABLE 3-continued

| | Undissolved Oxidized Cellulose | Dissolved Oxidized Cellulose |
|---|---|---|
| | 0.56 | |
| | 0.59 | |
| | 0.6 | |
| | 0.6 | |
| | 0.62 | |
| | 0.59 | |
| | 0.61 | 0.52 |
| | 0.57 | 0.006 |
| mean | 0.59 | 0.52 |
| std dev | 0.020 | 0.006 |

Example 19

Formation of Oxidized Cellulose Microspheres Encapsulating CDDP Loaded PLGA Microspheres and Doxorubicin Loaded PLGA Microspheres.

Approximately 2 grams of 15% by weight/volume oxidized cellulose solution was added into a glass scintillation vial to which approximately 150 mg of Vitamin E d-alpha tocopheryl polyethylene glycol 1000 succinate (TPGS) was added and vortexed for a minimum of about 30 seconds to ensure its complete dissolution. Approximately 50 mg of CDDP loaded microspheres containing about 16.65 mg of CDDP along with approximately 40 mg of doxorubicin loaded microspheres containing about 13.32 mg of doxorubicin were added to the solution. The vial was capped and vortexed from about 15 to about 20 seconds.

The oxidized cellulose solution containing CDDP loaded microspheres and doxorubicin loaded microspheres was added drop-wise to a 1 liter glass beaker containing about 500 mL heavy mineral oil and about 250 mL of cottonseed oil and mixed for about 90 minutes at about 450 RPM. Another 200 mL of heavy mineral oil was added to further extract the NMP solvent from the oxidized cellulose microspheres.

About 50 mL of n-heptane was added at approximately the 2.5 hour time point and allowed to mix for about 15 minutes and the entire contents were poured through a set of approximately 12-inch diameter stainless steel sieves, stacked in descending order, 300 μm, 200 μm, 105 μm, and 25 μm. Microspheres were harvested in each size range and were then washed with n-heptane to remove any residual oil from their surface.

The oxidized cellulose microspheres encapsulating CDDP loaded microspheres and of doxorubicin loaded microspheres were collected on Whatman #4 filter paper under vacuum and air-dried overnight before being bottled under an argon overlay.

Figure 29:
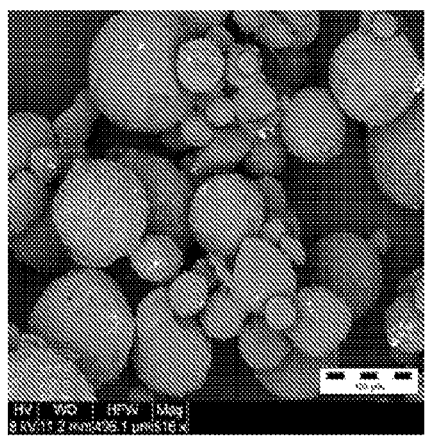
FIG. 29 is a scanning electron microscope image of oxidized cellulose microspheres encapsulating cis-diamminedichloroplatinum(II) loaded poly(lactic-co-glycolic acid) microspheres and doxorubicin loaded poly(lactic-co-glycolic acid) microspheres in accordance with the present disclosure.
Figure 30:
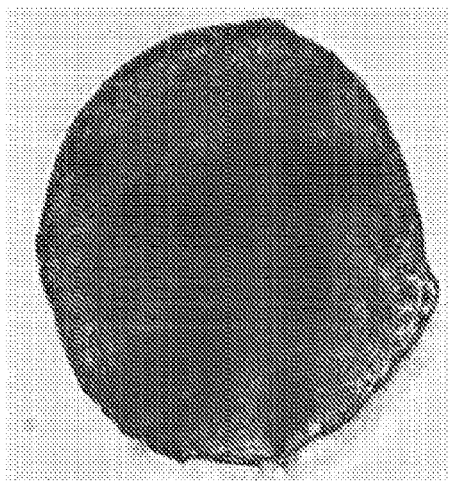
FIG. 30 is a light microscope image of microspheres of FIG. 29 in accordance with the present disclosure.

Collected microspheres were imaged using a FEI Quanta 600/650 FEG SEM, which are shown in FIG. 29 at about 516×. Intact microspheres were imaged in mineral oil, using transmitted light. The SEM images show microspheres having a spherical shape and a smooth outer surface. Collected microsphere was also imaged using a Keyence VHX-600 light microscope, which is shown in FIG. 30 at about 1,000×. The microsphere was imaged in low vacuum conditions using a backscatter electron detector. The image of FIG. 30 shows a larger oxidized cellulose microsphere encapsulating CDDP loaded PLGA microspheres, which were observed as dark spots, and doxorubicin loaded PLGA microspheres, which were observed to be red.

Figure 31:
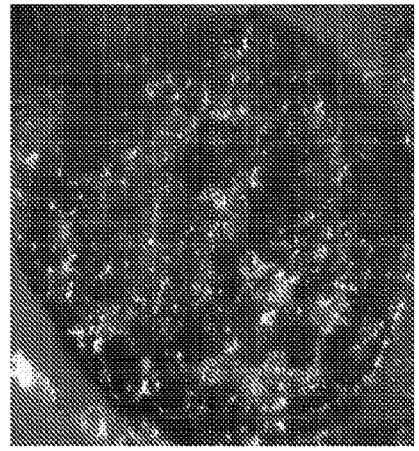
FIG. 31 is a light microscope image of a cross-section of the microsphere of FIG. 30 in accordance with the present disclosure.

The microsphere of FIG. 30 was imbedded in epoxy and a cross-section thereof was obtained. The cross-section of the microsphere was imaged using Keyence VHX-600 light microscope, which is shown in FIG. 31 at about 1,000×. The image of FIG. 31 shows that the oxidized cellulose microsphere encapsulating CDDP loaded PLGA microspheres, which were observed to be orange, and doxorubicin loaded PLGA microspheres, which were observed to be red.

Figure 32:
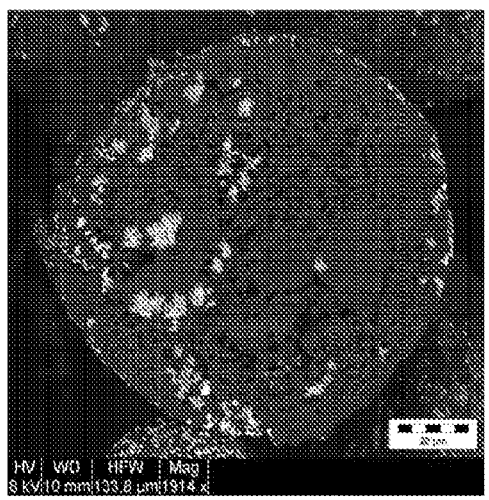
FIG. 32 is a scanning electron microscope image of a cross-section of the microsphere of FIG. 30 in accordance with the present disclosure.

The cross-section of the microsphere of FIG. 30 was also imaged using FEI Quanta 600/650 FEG SEM, which is shown in FIG. 32 at about 1914×. The image of FIG. 32 shows platinum crystals, which are indicative of the presence of CDDP.

Figure 33:
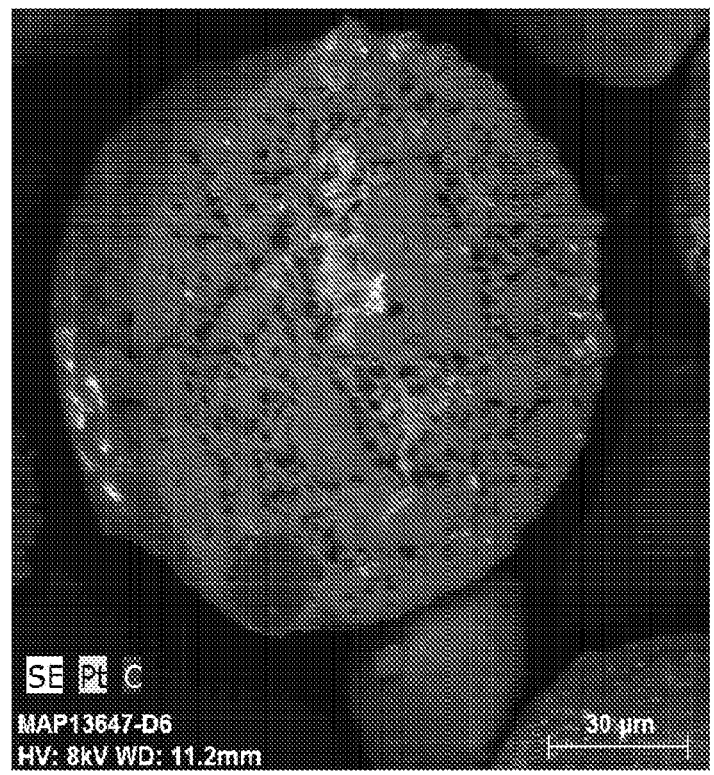
FIG. 33 is a scanning electron microscope image with color-coded energy dispersive spectra map of a cross-section of the microsphere of FIG. 30 in accordance with the present disclosure.

The cross-section of the microspheres of FIG. 30 was further imaged using FEI Quanta 600/650 FEG SEM with color-coded energy dispersive spectra (EDS) map, which is shown in FIG. 33. The EDS map suggests diffuse distribution of CDDP, observed as green in color, throughout the oxidized cellulose microsphere, with higher concentrations in some specific areas. The EDS map also shows areas of higher concentration of carbon, observed as blue in color, which is inferred as the inner microspheres loaded with doxorubicin.

Example 20

Covalent Crosslinking of Oxidized Cellulose Microspheres of Example 19.

A 5.0% solution by weight/volume of aziridine was prepared by adding about 5 mL of aziridine to a 100 mL Class A volumetric flask and filling to the 100 mL mark with n-heptane. Approximately 700 mg to about 1.5 grams of oxidized cellulose microspheres of Example 19 were carefully introduced into the mouth of a spheronizer and the speed of the unit was adjusted to ensure the particles were tumbling over each other without being ejected. About 10 mL of 5.0% aziridine solution was transferred into the chamber of the spheronizer containing the oxidized microspheres of Example 19 to be crosslinked and the speed of the rotation was set at approximately 50 rpm. Approximately 15 minutes after starting the rotation and allowing for crosslinking to occur, a stream of nitrogen was directed slightly into the open end of the spheronizer to facilitate the evaporation of the n-heptane until the microbeads were tumbling freely in the chamber. The microspheres were collected only after they tumbled freely in the chamber upon which time they were collected and bottled in 10 mL Wheaton vials under an argon overlay, labeled and stored at room temperature until needed.

Example 21

Triglyceride Overcoating of Oxidized Cellulose Microspheres of Example 19.

A 0.5% solution by weight/volume of triglyceride in n-heptane was prepared by weighing 500 mg of the triglyceride into a 100 mL Class A volumetric flask and filling to the 100 mL mark with n-heptane. The flask was capped and gently swirled until the triglyceride was completely dissolved.

Approximately 10 mL of the triglyceride solution was transferred into the open end of a spheronizer along with the oxidized cellulose microspheres of Example 19 to be overcoated and the speed of the rotation was set at about 50 rpm while a stream of nitrogen was directed slightly into the open end of the spheronizer to facilitate the evaporation of the n-heptane thereby depositing a thin overcoat of triglyceride onto the surface of the microspheres and forming overcoated oxidized cellulose microspheres. The overcoated microspheres were collected only after they tumbled freely in the chamber. They were bottled in 10 mL Wheaton vials under an argon overlay, labeled and stored at room temperature until needed.

It will be appreciated that of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, or material.

What is claimed is:

1. A method comprising:
    forming an oxidized cellulose solution by contacting an oxidized cellulose with a solvent under an inert atmosphere to form a swelled oxidized cellulose mixture;
    adjusting the swelled oxidized cellulose mixture to a first temperature;
    contacting the swelled oxidized cellulose mixture with a salt under the inert atmosphere to form an oxidized cellulose solution;
    adjusting the oxidized cellulose solution to a second temperature;
    contacting the oxidized cellulose solution with at least one visualization agent to form a discontinuous phase liquid;
    contacting the discontinuous phase liquid with a continuous phase liquid to form an emulsion; and
    contacting the emulsion with a third phase liquid to extract the solvent from the emulsion thereby forming a plurality of microspheres.

2. The method according to claim 1, wherein the third phase liquid is miscible with the continuous composition and the discontinuous composition.

3. The method according to claim 2, wherein the third phase liquid is selected from the group consisting of isopropyl myristate, hexane, triglycerides and combinations thereof.

4. The method according to claim 1, wherein the third phase liquid is present in an amount from about 300% by volume to about 200% by volume of the continuous phase liquid.

5. The method according to claim 1, wherein the first temperature is from about 115° C. to about 145° C. and the second temperature is from about 90° C. to about 120° C.

6. The method according to claim 1, wherein the solvent is selected from the group consisting of N,N-Dimethyl acetamide, N-methyl-2-pyrrolidinone, and combinations thereof.

7. The method according to claim 1, wherein the salt is selected from the group consisting of lithium halides, sodium halides, potassium halides, and combinations thereof.

8. A microsphere comprising:
    a shell comprising a first biodegradable polymer encapsulating at least one second microsphere, the at least one second microsphere comprising a second biodegradable polymer and at least one visualization agent.

9. The microsphere according to claim 8, wherein the first biodegradable polymer and the second biodegradable polymer are different and at least one of the first biodegradable polymer or the second biodegradable polymer is modified cellulose.

10. The microsphere according to claim 8, wherein at least one of the first biodegradable polymer or the second biodegradable polymer is an aliphatic polyester.

11. The microsphere according to claim 10, wherein the aliphatic polyester is selected from the group consisting of polylactide, polylactide-co-glycolide, polylactide-polycaprolactone, and combinations thereof.

12. The microsphere according to claim 8, further comprising at least one additional visualization agent different from the at least one visualization agent of the at least one second microsphere.

13. The microsphere according to claim 12, further comprising at least one first bioactive agent, wherein the at least one second microsphere comprises at least one second bioactive agent, the at least one first bioactive agent and the at least one second bioactive agent are different.

14. The microsphere according to claim 8, wherein the first biodegradable polymer encapsulates at least one third microsphere, the at least one third microsphere comprising at least one additional visualization agent different from the at least one visualization agent of the at least one second microsphere.

15. The microsphere according to claim 14, wherein the at least one second microsphere comprises at least one first bioactive agent and the at least one third microsphere comprises at least one second bioactive agent, the at least one first bioactive agent and the at least one second bioactive agent are different.

16. The microsphere according to claim 8, further comprising at least one first bioactive agent, wherein the at least one second microsphere comprises a second shell encapsulating at least one third microsphere comprising a third biodegradable polymer and at least one second bioactive agent.

17. The method according to claim 1, wherein the plurality of microspheres include oxidized cellulose having a degree of oxidation from about 80% to about 120% of a degree of oxidation of the oxidized cellulose prior to dissolution.

18. The method according to claim 1, wherein the plurality of microspheres include oxidized cellulose having a molecular weight from about 80% to about 120% of the molecular weight of the oxidized cellulose prior to dissolution.

19. The method according to claim 1, further comprising encapsulating one or more of the plurality of microspheres within a shell.

20. The method according to claim 1, wherein the at least one visualization agent is selected from the group consisting of dyes, fluorescent compounds, x-ray contrast agents, ultrasonic contrast agents, MRI contrast agents, CT scan contrast agents, radionucleotides, magnetic materials, and combinations thereof.

* * * * *